United States Patent [19]
Macfarlane et al.

[11] Patent Number: 6,157,445
[45] Date of Patent: *Dec. 5, 2000

[54] METHOD AND APPARATUS FOR DETECTING AND MEASURING CONDITIONS AFFECTING COLOR

[75] Inventors: Darby Simpson Macfarlane; David Kenneth Macfarlane, both of Hastings-on-Hudson; Fred W. Billmeyer, Jr., Schenectady, all of N.Y.

[73] Assignee: Chromatics Color Sciences International, Inc., New York, N.Y.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/939,232

[22] Filed: Sep. 29, 1997

Related U.S. Application Data

[63] Continuation-in-part of application No. 08/239,733, May 9, 1994, Pat. No. 5,671,735, and a continuation-in-part of application No. 08/481,174, Jun. 8, 1995, abandoned, and a continuation-in-part of application No. 08/657,590, Jun. 7, 1996, and a continuation-in-part of application No. 08/476,809, Jun. 8, 1995, which is a continuation-in-part of application No. 08/239,733, May 9, 1994, said application No. 08/481,174, Jun. 8, 1995, is a continuation-in-part of application No. 08/239,733, May 9, 1994, which is a continuation-in-part of application No. 08/021,657, Feb. 22, 1993, Pat. No. 5,313,267, which is a continuation of application No. 07/818,488, Jan. 7, 1992, abandoned, which is a continuation of application No. 07/402,815, Aug. 24, 1989, abandoned.

[51] Int. Cl.[7] ........................................ G01J 1/10
[52] U.S. Cl. .................. 356/243.5; 356/421; 600/310
[58] Field of Search .................. 600/310, 315, 600/322, 473, 476, 477; 356/402, 405, 421, 243.5; 73/1.01; 250/252.1

[56] References Cited

U.S. PATENT DOCUMENTS

Re. 31,815  1/1985  Alfano ..................................... 128/665

(List continued on next page.)

FOREIGN PATENT DOCUMENTS 0128442  12/1984  European Pat. Off. .
655221  5/1995  European Pat. Off. .

(List continued on next page.)

OTHER PUBLICATIONS

ASTM Standard Method of Specifying Color by the Munsell System (D 1535—69), pp. 1–22, Reapproved 1974.

(List continued on next page.)

*Primary Examiner*—Eric F. Winakur
*Attorney, Agent, or Firm*—Baker Botts L.L.P.

[57] ABSTRACT

A method and apparatus for determining the condition of a test subject based on color uses a color measuring instrument to detect change in a color factor indicative of a condition such as a disease, spoilage, ageing, etc. A medical condition such as bilirubinemia that affects skin color can be detected. One measures color factors such as Hunter b and L in the subjects' skin color. For predetermined ranges of one color factor, in particular L, changes in the other color factor, e.g. Hunter b, above predetermined levels are indicative of the medical condition. In many cases, a single measurement of the color factors can be utilized as a warning of the likelihood of the medical or contaminated condition, if the ordinary range of the color factor is known for healthy individuals with skin coloration like that of the test subject. Even if there has been no baseline measurement and the test subject's color is such that a single reading of one or two color factors will not warn of the possible presence of the medical condition or contamination, sequential readings can indicate the presence or absence of the condition based upon changes in the measured color factor, or lack of changes. The color measuring techniques apply to a wide range of biological test subjects (e.g. hair, teeth, tissue, excretions, foods, soil, animals, plants). Methods and apparatus for determining accurate hair color classifications and appropriate coloring agents to bring about a selected change of color include a table of hair color classifications, a color measuring instrument to arrive at Hunter L, a and b for use in identifying a particular classification from the table and a database that identifies appropriate coloring agents based on a selection of coloring actions from a menu and the classifications of hair color.

4 Claims, 9 Drawing Sheets

U.S. PATENT DOCUMENTS

| | | |
|---|---|---|
| 205,578 | 7/1878 | Rose et al. . |
| 1,496,374 | 6/1924 | Jones . |
| 1,582,122 | 4/1926 | Clapp . |
| 1,629,330 | 5/1927 | Adler . |
| 1,741,080 | 12/1929 | Stenz . |
| 1,802,007 | 4/1931 | Durfee . |
| 1,979,119 | 10/1934 | Radzinsky . |
| 2,221,774 | 11/1940 | Bowser . |
| 2,809,552 | 10/1957 | Ciavola . |
| 3,003,388 | 10/1961 | Hunter et al. . |
| 3,176,577 | 4/1965 | Frank . |
| 3,520,626 | 7/1970 | Hach . |
| 3,533,399 | 10/1970 | Goldberg et al. . |
| 3,627,431 | 12/1971 | Komarniski . |
| 3,736,064 | 5/1973 | Kent et al. . |
| 3,773,425 | 11/1973 | Bentley . |
| 3,922,095 | 11/1975 | Lee . |
| 3,935,436 | 1/1976 | Halschlag et al. . |
| 3,942,899 | 3/1976 | Longhenry . |
| 3,973,129 | 8/1976 | Blumberg et al. . |
| 3,999,866 | 12/1976 | Mathisen . |
| 4,029,085 | 6/1977 | Dewitt et al. . |
| 4,093,991 | 6/1978 | Christie, Jr. et al. ............... 364/525 |
| 4,135,497 | 1/1979 | Meyers et al. . |
| 4,241,738 | 12/1980 | Lübbers et al. .................. 128/666 |
| 4,267,844 | 5/1981 | Yamanishi ....................... 128/633 |
| 4,302,971 | 12/1981 | Luk ................................... 73/356 |
| 4,357,106 | 11/1982 | Tschirren et al. ................ 356/44 |
| 4,423,736 | 1/1984 | Dewitt et al. .................... 128/633 |
| 4,434,467 | 2/1984 | Scott ................................ 364/400 |
| 4,479,499 | 10/1984 | Alfano et al. .................... 128/665 |
| 4,561,850 | 12/1985 | Fabbri et al. ..................... 434/98 |
| 4,648,051 | 3/1987 | Wandell et al. . |
| 4,654,794 | 3/1987 | O'Brien ............................ 364/413 |
| 4,681,546 | 7/1987 | Hart .................................. 434/99 |
| 4,723,554 | 2/1988 | Oman et al. ..................... 128/664 |
| 4,795,254 | 1/1989 | Kravetz . |
| 4,813,000 | 3/1989 | Wyman et al. .................. 364/526 |
| 4,842,523 | 6/1989 | Bourdier et al. ................. 434/371 |
| 4,857,071 | 8/1989 | Anderson ......................... 8/414 |
| 4,877,034 | 10/1989 | Atkins et al. ..................... 128/664 |
| 4,894,547 | 1/1990 | Leffell et al. .................... 250/461.2 |
| 4,909,632 | 3/1990 | Macfarlane ....................... 356/402 |
| 4,964,874 | 10/1990 | Saphakkul ........................ 8/429 |
| 4,981,361 | 1/1991 | Kobayashi et al. . |
| 4,989,983 | 2/1991 | Terada et al. . |
| 5,127,406 | 7/1992 | Yamaguchi ...................... 128/633 |
| 5,161,553 | 11/1992 | Cohen et al. ..................... 132/205 |
| 5,259,382 | 11/1993 | Kronberg ......................... 128/633 |
| 5,311,293 | 5/1994 | Macfarlane et al. ............. 356/421 |
| 5,313,267 | 5/1994 | Macfarlane et al. ............. 356/405 |
| 5,337,745 | 8/1994 | Benaron et al. .................. 128/633 |
| 5,344,463 | 9/1994 | Chan et al. ....................... 8/408 |
| 5,353,790 | 10/1994 | Jacques et al. ................... 128/633 |
| 5,387,977 | 2/1995 | Berg et al. ........................ 356/407 |
| 5,416,613 | 5/1995 | Rolleston et al. ................ 356/243.5 |
| 5,424,545 | 6/1995 | Block et al. ...................... 356/405 |
| 5,642,189 | 6/1997 | Alguard . |
| 5,671,735 | 9/1997 | Macfarlane et al. ............. 356/405 |

FOREIGN PATENT DOCUMENTS

| | | |
|---|---|---|
| 1347400 | 11/1963 | France . |
| 1468339 | 12/1966 | France . |
| 2587181 | 3/1987 | France . |
| 1236984 | 3/1967 | Germany . |
| 2916061 | 11/1979 | Germany . |
| 3827457 | 6/1989 | Germany . |
| 59-020824 | 2/1984 | Japan . |
| 0037896 | 8/1985 | Japan . |
| 0257328 | 12/1985 | Japan . |
| 63 -206655 | 8/1988 | Japan . |
| 8401665 | 12/1985 | Netherlands . |
| 2001595 | 10/1993 | Russian Federation . |

OTHER PUBLICATIONS

C. Jackson, *Color Me Beautiful*, New York, Ballantine Books, Apr. 1981, pp. 25, 26, Color Palettes, 37–39, 41–59, 61–74, 143–147.

G. Pickney et al., *Your New Image Through Color & Line*, California Fashion Image/Crown Summit Books, Sep. 1981, pp. 1–3, 17, 21–29, 97–105, 111, 112, 120–127.

R. Evans, *An Introduction to Color*, Wiley, New York, 1948, pp. 26–27 and 87–90.

C.S. McCamy et al., *A Color–Rendition Chart*, J. Appl. Photogr. Eng. vol. 2, pp. 95–99 (1976).

C.A. Pearson, *Face Colour As a Sign Of Tuberculosis*, Color Res. Appl. vol. 7, pp. 31–33, (1982).

P.A. Lovett et al., *Measurement of the Skin Color of Babies in Hospital*, Proc. of CIBS Lighting Conference, 1986, HMSO, London, 1986, pp. 140–154.

G. Wyszecki et al., *Color Science*, 2nd Edition (1982) Table of Contents, p. 63–72.

Advertisement for digital photometer by Photo Research in *Optical Spectra*, Nov., 1973.

Advertisement for light meters sold by Minolta Corporation in *Studio Photography*, Nov. 1981, vol. 17, No. 11.

F. Billmeyer & M. Saltzman, "Principles of Color Technology," 2nd ed., John Wiley & Sons, New York, NY 1981 pp. 18–19, 59–61, 92.

M. Kenny et al. "Transcutaneous Bilirubin Monitoring of Newborns", *Annals of the New York Academy of Sciences*, vol. 428, pp. 251–262 (1984).

R.E. Hannemann et al., "Neonatal Serum Bilirubin from Skin Reflectance", *Pediatric Research*, vol. 12, pp. 207–210 (1978).

F. Billmeyer, Jr., "Quantifying Color Appearance Visually and Instrumentally", *Color Research and Application*, vol. 13, pp. 140–145 (1988).

T. Hegyi, M.D., "Transcutaneous Bilirubinometry In The Newborn Infant: State of the Art", *Journal of Clinical Monitoring*, vol. 2, pp. 53–59 (1986).

R.E. Hanneman et al., "Evaluation of Minolta Bilirubin Meter as a Screening Device", *Pediatrics*, vol. 69, pp. 107–109 (1982).

D. Onks et al., "Effect of Melanin, Oxyhemoglobin and Bilirubin on Transcutaneous Bilirubinometry", *Acta. Peadiatrica*, vol. 82, pp. 19–21 (1993).

F.D. Ortega et al., "Bilirrubinometria Transcutanea: Correlacion del Area de Medida Con La Espectropometria y Colorimetria Por Diazorreaccion", Am. Exp. Pediarr., vol. 39, pp. 438–440 (1993).

R.E. Schumacher, "Noninvasive Measurement of Bilirubin in the Newborn", *Clinics in Perinatology*, vol. 17, pp. 417–435 (1990).

I. Yamanouchi et al., "Transcutaneous Bilirubinometry: Preliminary Studies of Noninvasive Transcutaneous Bilirubin Meters in the Okayama National Hospital", *Pediatrics*, vol. 65, pp. 195–202 (1980).

Advertisement for portable photometer by Photo Research in *Optica Spectra*, Nov., 1973.

D. Tudehope et al., "Non–invasive method of measuring bilirubin levels in newborn infants", *The Medical Journal of Australia*, vol. 1, pp. 165–168 (1982).

W.A. Gerrard et al., the Measurement of Hair Colour, International Journal of Cosmetic Science, vol. 11, pp. 97–101 (1989).

METHOD AND APPARATUS FOR DETECTING AND MEASURING CONDITIONS AFFECTING COLOR

CROSS REFERENCE TO RELATED APPLICATIONS

This is a continuation-in-part of U.S. patent application Ser. No. 08/239,733 ('733 application), filed May 9, 1994, now U.S. Pat. No. 5,671,735, and is a continuation-in-part of U.S. patent application Ser. No. 08/481,174 ('174 application), filed Jun. 8, 1995, now abandoned. This is a continuation-in-part of U.S. patent application Ser. No. 08/657,590, filed Jun. 7, 1996 and of U.S. patent application Ser. No. 08/476,809, filed Jun. 8, 1995. The '809 and '174 applications are each a continuation-in-part of the '733 application, which is a continuation-in-part of U.S. patent application Ser. No. 08/021,657, filed Feb. 22, 1993, now U.S. Pat. No. 5,313,267. Ser. No. 08/021,657 is a continuation of Ser. No. 07/818,488, filed Jan. 7, 1992, which is a continuation of Ser. No. 07/402,815, filed Aug. 24, 1989 abandoned. No right of priority is claimed based upon any application filed earlier than Aug. 24, 1989.

TECHNICAL FIELD OF THE INVENTION

This invention relates to a method and apparatus for the detection and/or measurement of a condition that affects the color of a test subject, and more particularly to a process and instrument for measuring at least one color characteristic or factor of a test subject indicative of the condition of interest such as biological condition or hair coloration.

BACKGROUND OF THE INVENTION

Visual observation of a subject for changes in coloration indicative of a particular condition has often occurred. The subject may be a person or animal being observed to determine the presence or absence of a medical condition. The color characteristics or a single color characteristic of other test subjects such as biopsy specimens or excretions have diagnostic value.

An individual person's skin color is often assessed by her or his doctor. Hypertension, tuberculosis, sclerosis of the liver, to name just a few, are examples of ailments with symptomatic skin color changes among at least a sizeable population segment. Hair color evaluation and dental coloration evaluation are valuable. These may bear on the health of the individual, or on the health of the individual's hair and teeth, or these may permit accurate cosmetic activities, for example, to counteract graying or to accurately match new dental work to existing teeth.

Likewise, the condition of plants and agricultural products is visually inspected for color as an indication of condition. Contamination of soil is likewise apparent from visual inspection. Such visual inspections are subjective. Measuring by instrument the color characteristics that are key to the visual inspection has the benefit of objectivity and consistency.

In the past, hyperbilirubinemia in newborns has been detected by visually observing an individual for jaundice or by routinely taking and testing a blood sample. Upon detection, hyperbilirubinemia has been treated by phototherapy. During the course of phototherapy, blood samples have been taken and tested at regular intervals until it was determined that the level of serum bilirubin had decreased to an acceptable level.

In infants, there is little blood available for use in the blood testing for hyperbilirubinemia. So much blood is drawn that transfusions are often necessary to replace the drawn blood. The newborn is thereby exposed to all of the risks that transfusions bring. Blood sampling and transfusions are, of course, painful to the newborn, and as with any invasive procedure, both present medical risks, such as for example, risk of infection. There is a need, therefore, for a reliable, noninvasive technique for detecting and measuring a skin color affecting medical condition such as hyperbilirubinemia.

This is one example of a wider need for procedures and instruments to objectively and consistently determine a color characteristic or factor indicative of the condition of a test subject or indicative of a particular ailment or condition. The methods and apparatus of this invention can be employed where previously visual inspection, of which examples are given above, have been carried out at least in part on the basis of observable color characteristics.

This invention also relates to a method and apparatus for the categorizing of hair color and hair color treatment agents for their interrelationship, and more particularly to a process and instrument for measuring three color characteristics of hair color and categorizing it and determining the effect of a wide variety of hair coloring agents thereon.

Hair coloring agent choices are often made by a consumer based on relatively vague indications of the color to be expected as a result of the use of the agent on an individual person's hair. This approach does not take into consideration the color of the hair that is to be treated and how interaction of that particular individual's hair color with the coloring agent will affect the resultant color.

No reliable source of information has been available to a private consumer regarding what the actual color of her or his hair is and what hair coloring agent will provide the hair color alteration that consumer seeks.

Consequently it can be seen there exists a need for procedures and apparatus that will accurately characterize an individual's hair color to enable selection of appropriate coloring agents for a desired color result. Likewise there exists a need for a reliable process and instrumentation to permit the use of the accurate color characterization of an individual's hair color in the selection of hair coloring agents to effect hair color alterations of a type desired by the individual.

BRIEF SUMMARY OF THE INVENTION

According to this invention there is provided a method and apparatus for detecting and quantitatively measuring a condition affecting the color of a test subject. The method includes measuring at least one color characteristic of the subject.

In one exemplary procedure according to this invention at least one skin color characteristic is measured at least at first and second points in time. To test for hyperbilirubinemia, the two measurements are then compared for change. In the preferred procedure a second skin color characteristic is also measured on the basis of which the subject can be assigned to one of plural categories among which varying amounts of change in the first-mentioned skin color characteristic are indicative of the presence of a medical condition. The first characteristic is then observed for a change of measured value sufficient to indicate the medical condition for a subject in that category. Preferably, a base reading of at least the first color characteristic is first made at a time the subject is without characteristic skin coloration indicative of the medical condition for which he or she is to be tested.

In the case of hyperbilirubinemia detection, the first skin color characteristic is Hunter b, which is a color factor dependent on the relative content, in a color, of two opponent colors, yellow and blue. Hunter b is a factor comprising a first function (Y) weighted in a first portion of the spectrum, the yellower portion, a second function (Z) weighted in a second portion of the spectrum, the bluer portion, and a weighting term ($1/Y^{1/2}$) that is a function of the lightness of a color and that decreases the value of the color factor as lightness increases. Y and Z are part of the three tristimulus values X, Y and Z known to the color scientist for the purpose of defining a color. They are measurable by commercially available instruments such as colorimeters.

In the case of testing newborns for hyperbilirubinemia, readings of Hunter b and the Hunter lightness measure L are made shortly after birth. These can provide the base reading since hyperbilirubinemia does not manifest itself immediately after birth. The first reading is preferably made within five hours, but as soon as possible after birth. Subsequent readings are then made during the next few days. The subsequent readings of Hunter b are compared with the first, baseline reading of Hunter b to determine whether Hunter b has increased to an extent that indicates a degree of jaundice characteristic of hyperbilirubinemia for a person having the range of the subject's particular skin lightness L. L is measured during each subsequent test to be sure that it remains close to the original reading. This gives a degree of confidence that the test procedures are being conducted appropriately.

In the event that the medical condition affecting skin color is detected in a procedure like that described above for hyperbilirubinemia, then the measuring of skin color characteristics continues at regular intervals until the symptomatic color characteristic abates sufficiently to indicate the individual's recovery from the medical condition. In the case of hyperbilirubinemia, phototherapy is administered once a sufficient change in Hunter b is observed to indicate the jaundice of hyperbilirubinemia. Throughout the course of phototherapy, then, the Hunter b and L characteristics are continually monitored until the jaundice has been eliminated. This is valuable in removing the newborn from under the phototherapy lamps, since there is the danger of damage to the newborn's eyes in the event eye protection is prematurely removed or accidentally dislodged.

The apparatus used in accordance with this invention includes a color measuring device such as a colorimeter and computational means for storing and comparing the characteristic or characteristics that are measured when testing for the medical condition. Where Hunter b is measured for the purpose of detecting hyperbilirubinemia, a colorimeter capable of calculating Hunter b and L can be used. This can be a commercially available colorimeter with this capability. The computational means preferably has sufficient memory to store one or more previous readings and should be programmed to compare previous and current readings to detect changes in Hunter b and L. Preferably the colorimeter and the computational means are integrated in a single instrument, but the commercial colorimeter can be utilized in cooperation with, for example, a personal computer, which stores and can compare Hunter b and L values from measurements taken at timed intervals. Likewise, the computational means, whether an integrated part of the instrument or a separate computer, can be used to store ranges of lightness L and the increases in Hunter b that, for the various lightness ranges, indicate an unacceptable increase in serum bilirubin.

In one embodiment Hunter a is also measured. The ordinary range of Hunter a for individuals is known. If Hunter a lies outside the ordinary range the reason for this should be determined. If it is because the infant is flushed from crying or has just been washed and rubbed dry the Hunter a is not an indication of a medical problem. If Hunter a is above the ordinary range, but the infant has not been crying, or recently washed or some other non-medical reason, a circulatory problem could be the reason and bears watching to observe if a medical condition is present or phototherapy is in progress. Also, Hunter a sometimes increases just before the jaundice due to hyperbilirubinemia increasing Hunter b. Hunter a, then, may be a warning for closer observation to observe if a medical condition is present or phototherapy is in progress. A decrease in Hunter a along with an increase in both Hunter L and Hunter b such that the ratio of Hunter L to Hunter b remains essentially constant can mean that the infant is anemic and therefore pale, in which case the increase in Hunter b (with a simultaneous increase in Hunter L) would not be indicative of hyperbilirubinemia. The observation of Hunter a then may suggest various medical conditions and it allows one to understand the Hunter L and b readings better and to be more certain whether they are or are not indicative of hyperbilirubinemia.

Preferably, each skin color characteristic measurement used to assess the presence or absence of the condition for which testing is carried out is actually an average of multiple tests. For example, when newborns are tested for the jaundice that signals hyperbilirubinemia, multiple readings are made at multiple sites. Five or six Hunter value readings are made at, for example, each of several locations which may include some or all of a forehead location, at least one chest location, a cheek location and two back locations. Out of range Hunter L, a and b values are discarded. At each site, the Hunter readings that have the highest and lowest values of L, a and b are discarded, then all of the readings of each Hunter characteristic are averaged for each site. Subsequent readings are made in the same manner at exactly the same sites and compared. As used herein, the terms "Hunter a," "Hunter b," and "Hunter L" include such average values, but are not limited to just the values arrived at by the averaging technique unless expressly so-limited. The discarding and averaging is readily accomplished by the computational provisions of the test equipment. The averaging technique may improve the testing of other than skin color where the testing steps of this invention are used, for example in the evaluation of hair by color measurement.

In skin color testing, it is important to cleanse the site utilizing a cleansing agent that does not contribute any coloration. Likewise, when testing is carried out on test subjects other than an individual's skin, the test subject should be free of any color altering contaminant. In skin color testing, the site on the test subject should be dry, and in all cases the instrument should have the capability of being applied to the site in such a manner that ambient light does not enter the instrument.

In one method according to the invention Hunter L and b are used. Hunter L is monitored for consistency each time measurements are made. The change in Hunter b is monitored for a warning of hyperbilirubinemia. In another method according to the invention Hunter L, a and b are used. Hunter L is monitored for consistency, Hunter b is monitored for a warning of hyperbilirubinemia, and Hunter a is observed for additional information as to the infant's condition.

Determination of the first and second skin color characteristics, Hunter L and b, at just one point in time can indicate or strongly suggest a medical condition affecting skin color if the first characteristic measurement is observed to lie outside a range of values for that characteristic known by experience to be normal for a subject having the particular measured value of the second characteristic. Again the value of Hunter a should be observed and if abnormal the reason should be sought. For example, in many individuals hyperbilirubinemia is strongly suggested if Hunter b and L are measured and it is determined that, based on skin color categories previously observed, Hunter b is above any ordinary value for a subject with skin having the L value measured. Also, even if baseline readings of Hunter b and L (and preferably a) are not made, changes in the value of Hunter b can nevertheless signal the presence of hyperbilirubinemia if measurements of the Hunter values are made at timed intervals in the foregoing fashion. Out of the ordinary increases in Hunter b, of for example two or more points, can be an indication of hyperbilirubinemia when the measured L value remains in a constant range from one measurement to the next. Similarly, large decreases in Hunter b, of for example two or more points, can be an indication of hyperbilirubinemia from which the infant is recovering, again if L remains relatively constant. If Hunter a changes due to a medical condition such as anemia and the ratio of Hunter L and Hunter b changes, then it is likely necessary to take the anemia into account, for example by using a different change in Hunter b to indicate hyperbilirubinemia or by multiplying Hunter b by a compensatory factor.

Significant testing has established the value of the foregoing techniques in detecting hyperbilirubinemia. The same techniques will indicate other jaundice-producing medical conditions in human and animal subjects. Hepatitis or liver disorders are examples of such medical conditions susceptible to diagnosis with the methods and apparatus of this invention.

Tuberculosis has been observed to affect skin color in dark skinned individuals such as many persons of African descent. Appropriate color measurement in accordance with this invention may provide a valuable diagnostic tool.

Biopsy specimens, body fluids, excretions, etc. are visually inspected for color. The techniques and instrumentation according to this invention can provide objectivity and consistency to such inspections.

According to this invention there is also provided a method and apparatus for accurately characterizing the hair color of individuals to enable identification of the hair color and products suitable to achieve a desired change in hair color, and more particularly to a method and apparatus for measuring color factors in an individual's hair color to assign that hair color to a classification previously determined to interact with identified hair coloring agents to bring about predictable color changes.

Through experimentation over a prolonged period, the applicants were able to compile a vast amount of information relating to coloration of virtually every imaginable hair color. Thousands of individual hair samples were treated with many various coloring agents. The hair color before and after such treatment was accurately, scientifically measured and characterized using known, reliable color measurement. Hair color was then assembled into a large number of categories based on ranges of the measured color factors. A database was assembled comprising the desired changes available through various hair coloring agents and the particular agents that would effect those changes in human hair to the various categories.

Instrumentation was implemented to measure from an individual's hair the color factors that operate to place the hair color in one of the numerous hair color classifications and to identify that classification to the individual or the individual's hair specialist. In addition, the instrumentation was arranged to allow for selection of a desired alteration in hair color, and on the basis of the gathered empirical data, hair coloring agents capable of effecting the desired change were located from within a database.

In an embodiment of the invention, the process for hair color analysis is carried out by measuring with a measuring instrument the value of a number of color factors in the color of an individual's hair at various sites, and then providing an indicator or table having a large number of hair color classifications defining ranges of those same color factors, and finally comparing the color factors of the indicator or table to the measured color factors to arrive at a classification of the individual's hair color.

In a preferred embodiment of the invention just described the color factors were Hunter L, a and b.

In an instrumentation implementing the process just described, a colorimeter was used to measure the color factors. The indicator or table having a large number of color classifications was retained in computer memory, and the comparison was made electronically between the memory retained classifications and the measured color factors.

To use the process just described a list or menu of possible choices for varying hair color was presented. Upon selection of that choice, along with the hair color classification as previously determined, is used together with a database of hair color classifications and associated product identifications empirically determined to effect the presented choices of color changes to locate in that database previously tested hair coloring agents capable of effecting the chosen action.

In one further embodiment of the process described, the color factors measured in an individual's hair color were Hunter L, a and b. Classifications of hair color provided in the indicator or table were percentages of grey in the hair of the individual. This embodiment enables the coloring of grey hair or partially grey hair to obtain an individual's natural hair coloring or another preferred hair color. This procedure required the selection of one of a number of categories of hair colors such as "light brown," "darkest blond," "light red," etc. The indicator or table that identified various hair color classifications was divided among broad hair color families or groups of categories, and for an individual the particular hair family division of the indicator associated with that individual's broad family of hair color was found. The ranges of color factors in that division were then compared with the factors measured in the individual's hair to arrive at a classification.

In another embodiment of the invention, to arrive at a hair color treatment agent, a database of hair color treatment agents and classifications of color characteristics of individuals was compiled and an individual's color characteristics were determined by measurement of color factors, followed by comparison of those color factors with ranges contained in the database. In one embodiment the color characteristic of the individual that provided the basis for comparison was skin color.

The above and further advantages of this invention will be better understood with reference to the following detailed description of the preferred embodiments taken in combination with the attached drawings.

DETAILED DESCRIPTION OF THE PREFERRED EMBODIMENT

Figures 1, 1A:
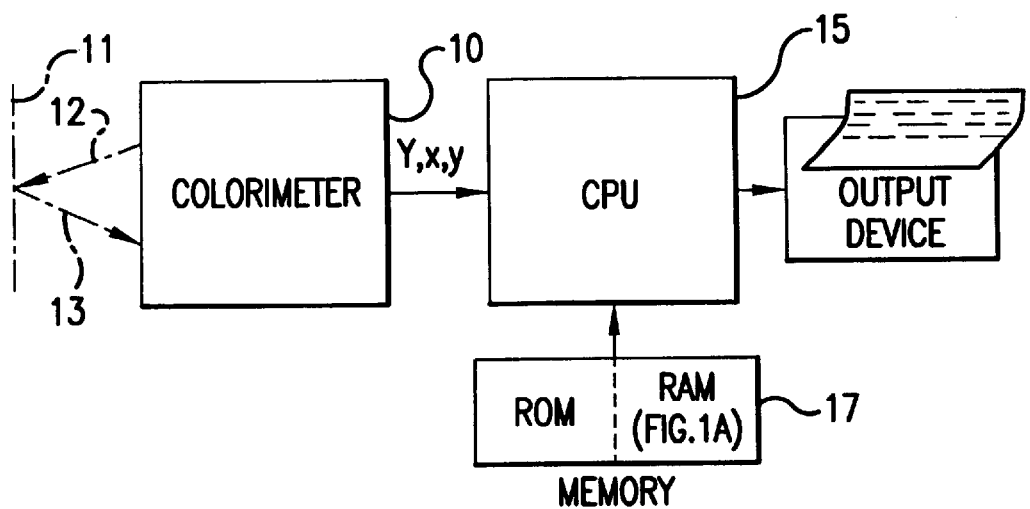
FIG. 1 is a block diagram illustration of an instrument for determining Hunter L, a and b values and for comparing changes in Hunter b to Hunter b changes predetermined to be indicative of bilirubinemia.
FIG. 1A is a diagrammatic illustration of exemplary memory content in an instrument like that of FIG. 1.
Figure 4:
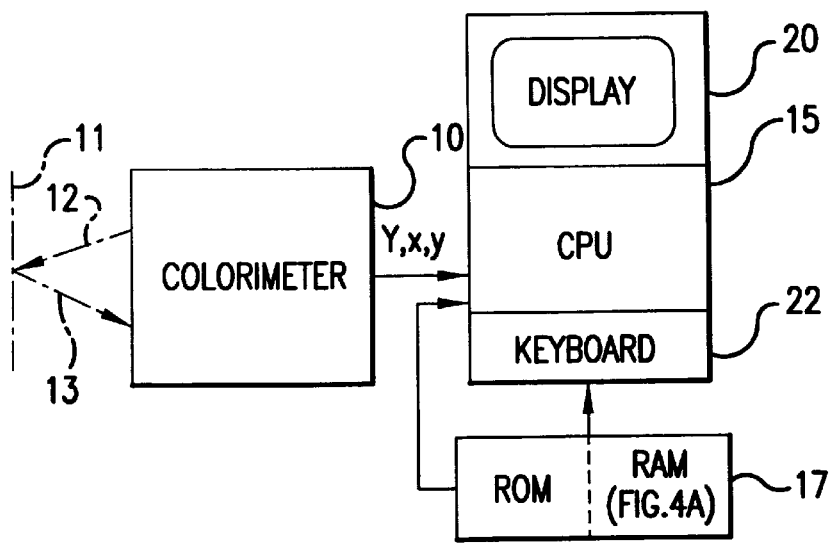
FIG. 4 is a block diagram illustration of an instrument for determining hair color Hunter L, a and b values and for those with hair color classifications previously determined and stored in memory.

Any modern version of two general types of color-measuring instruments, colorimeters and spectrophotometers, is an example of instruments suitable for the skin color measurement or hair color measurement according to preferred embodiments of this invention. The basic components of either type of instrument are a light source, a sample illumination and viewing arrangement, a means of selecting certain wavelengths of light for the measurement, a detector of the light reflected from the sample, and some relatively simple computing capacity. In commercially available instruments the main purposes of the computing capacity are to store and apply calibration information and to calculate various color coordinates for later use. In FIGS. 1 and 4, such color measuring instruments 10 are illustrated. An individual person's skin or hair 11 is illuminated by the instrument as generally indicated by the broken line arrow 12 and the instrument receives illumination reflected from the skin or hair 11 as generally indicated by the broken line arrow 13. Based on the illumination received by reflection from the skin or hair, the instrument 10 develops the coordinates Y, x and y. In FIGS. 1 and 4, the instrument 10 is a colorimeter, commercially available and suitable for development of the values Y, x and y. The instrument of FIG. 1 is particularly well suited for biological testing, such as in testing newborns for hyperbilirubinemia. The instrument of FIG. 4 is particularly well suited for methods associated with measuring hair coloration.

Another type of instrument that can be used in the skin color categorization methods according to this invention is the spectrophotometer that measures the reflectance at discrete wavelengths and from these data derives tristimulus values, from which can be computed the Hunter color values used to measure the color of a specimen (i.e., hair or skin) for diagnostic purposes as discussed below.

Important to the use of a commercial colorimeter of the kind employed for the color measurement instrument 10 of FIGS. 1 and 4 is the calibration of the instrument using a standard. In the early use of an instrument of this kind by the inventors, the "Light Skin" sample from the Macbeth Color Checker, described in the publication of C. S. McCamy, H. Marcus, and J. G. Davidson, "A Color-Rendition Chart," J. Appl. Photogr. Eng. 2, 95–99 (1976) was used. A tile of this approximate color was selected for its greater durability as an instrument standard. It was found, however, that the use of the "Light Skin" painted paper as the primary standard did not adequately avoid the phenomenon known as metamerism, by which objects that look alike (have the same perceived color) under some kinds of light sources, or to some observers, do not match under other types of light sources, or to other observers. By this phenomenon colorimeters may not read their colors the same as the average human observer would under the daylight type light source usually employed for visual observation, hence leading to an error in colorimeter calibration.

As an improved primary standard, the skin of a subject whose skin color measurements were highly reproducible, and in the approximate center of the range of skin colors of the human population was selected. The spectral reflectance factors of the skin of this subject were carefully measured on a Macbeth 1500 Plus spectrophotometer (Macbeth, New Windsor, N.Y.); these data are given in column 2 (second from left) of Table I at the wavelengths listed in column 1 (the leftmost column). By using well-established techniques of computer color matching, carried out on an ACS 1800 system equipped with an ACS SpectroSensor II color measuring instrument (Datacolor International, Lawrenceville, N.J.), a colorant formulation matching this skin color was developed. The spectral reflectance factors for this match are given in column 3 of Table I. It may be seen that the data closely match those of column 2, indicating the absence of metamerism. Calculations according to the CIE 1976 CIELAB system showed that the two data sets match to within 0.27–0.36 units, less than can be perceived by human color vision, for daylight, incandescent light, and cool white fluorescent light, the three most commonly used light sources for the proposed applications.

The above-mentioned formulation was made up in a stable, durable material, and tiles were prepared as instrument standards. The spectral reflectance factors of one of these tiles are given in column 4 of Table I. It was found, however, that the improvement in calibration resulted in color coordinates that were significantly different from those obtained in the many studies made with the earlier system. A decision was made to adjust the calibration values of the new tiles in order to achieve consistent results between the new and old methods of calibration. Column 5 of Table I gives the adjusted set of spectral reflectance factors for the tile of column 4. The CIE and Hunter color coordinates, for measurement with the specular component excluded and calculated for CIE standard illuminant C and the 1931 2° CIE standard observer, are also tabulated for each of the samples in the table.

TABLE I

| Wavelengths, nm. | Skin Standard | Formulation | Tile, correct | Tile, adjusted |
|---|---|---|---|---|
| 400 | 19.03 | 20.70 | 21.51 | 16.67 |
| 420 | 18.96 | 20.69 | 21.10 | 16.93 |
| 440 | 21.53 | 21.68 | 20.99 | 17.65 |
| 460 | 25.36 | 24.43 | 23.27 | 20.56 |
| 480 | 28.06 | 28.30 | 27.82 | 25.67 |
| 500 | 30.13 | 30.77 | 29.03 | 27.94 |
| 520 | 31.19 | 31.31 | 29.38 | 28.24 |
| 540 | 30.01 | 30.84 | 28.48 | 27.59 |
| 560 | 31.41 | 30.76 | 28.22 | 27.33 |
| 580 | 32.85 | 34.01 | 31.49 | 30.12 |
| 600 | 44.37 | 43.54 | 42.58 | 40.52 |
| 620 | 51.24 | 51.57 | 51.27 | 47.93 |
| 640 | 54.56 | 55.09 | 55.56 | 51.10 |
| 660 | 57.09 | 57.60 | 59.22 | 53.82 |
| 680 | 58.67 | 60.41 | 61.82 | 56.55 |
| 700 | 59.95 | 62.69 | 63.93 | 58.87 |
| X | 37.14 | 37.28 | 36.14 | 33.76 |
| Y | 34.66 | 34.89 | 33.07 | 31.53 |
| Z | 28.50 | 28.54 | 27.63 | 24.20 |
| x | 0.3703 | 0.3702 | 0.3732 | 0.3772 |
| y | 0.3456 | 0.3464 | 0.3415 | 0.3523 |
| L | 58.87 | 59.07 | 57.51 | 56.15 |
| a | 9.58 | 9.29 | 11.54 | 9.05 |
| b | 12.51 | 12.70 | 11.77 | 13.75 |

With a suitable standard, basically, calibration is carried out by forcing the colorimeter 10 to give the desired color coordinates Y, x and y mentioned above, while utilizing the colorimeter with the standard tile chosen. The method of calibration is known for particular instruments and follows a series of steps prescribed by the manufacturer that need not be detailed here.

In skin color testing, prior to each test of a subject, each test site is cleansed. A cleansing agent, such as isopropyl alcohol, which leaves behind no coloration, is suitable. In hair color analysis, prior to each test of a subject the subject's hair should be free of dirt. The site is well dried to avoid any wetness which may interfere with the reflection of light from the skin or hair 11 to the instrument 10. In all cases of testing, with the instrument correctly calibrated, the measuring head or instrument orifice is placed against the test site to be measured. Care is taken to avoid the admission of ambient light to the instrument. Pressing the instrument head firmly against the measurement site prevents the entry of ambient light. Additionally, it was determined that best results are obtained if one removes the instrument from the test site briefly, between illuminations. This can be provided for in software by a conventional delaying routine and, if desired, with an appropriate display instructing the user to remove the instrument briefly well away from the skin or hair.

In a colorimeter of the type shown in FIGS. 1 and 4, at block 10 the instrument has an internal microprocessor or other computing capability so that it is able to develop the color coordinates Y, x and y from the measured values X, Y and Z (Y being the same in each case). Certain colorimeters develop the Hunter color coordinates L, a, and b. Since the degree of computation that the color measuring device 10 (i.e. colorimeter or spectrophotometer) internally performs varies, the manner of calculating the Hunter values from the tristimulus coordinates is useful to an understanding and practice of the invention and will enable correct use of a CPU by appropriate calculation to perform the invention with any commercially available colorimeter or spectrophotometer. Most modern color measuring instruments begin with measurement of the tristimulus values X, Y, and Z. From these can be derived the CIE chromaticity coordinates x and y:

$$x = X/(X+Y+Z) \tag{1}$$

$$y = Y/(X+Y+Z) \tag{2}$$

The instrument 10 of FIG. 1 or 4 outputs the triplet of values x, y and Y as the starting point for further calculations by a central processing unit which can be dedicated microprocessor circuitry or personal computer 15. The remaining two tristimulus values X and Z are available by computation as follows:

$$X = xY/y, \text{ and} \tag{3}$$

$$Z = (1-x-y)Y/y \tag{4}$$

In one preferred embodiment for measurement of biological samples, the CPU according to FIG. 1 develops the Hunter value b discovered in accordance with this invention to be capable of use to detect and monitor hyperbilirubinemia. In another preferred embodiment for hair measurement, the CPU according to FIG. 4 develops the Hunter values L, a, and b. The Hunter L, b and a values are the three values derived by Richard S. Hunter in 1958. Richard S. Hunter, "Photoelectric Color Difference Meter," J. Opt. Soc. Am. 48, 985–995 (1958). The equations for these are:

$$L = 10(Y)^{1/2} \tag{5}$$

$$a = 17.5(1.02X - Y)/Y^{1/2} \tag{6}$$

$$b = 7.0(Y - 0.847Z)/Y^{1/2} \tag{7}$$

where L is a lightness coordinate whose values correlate better with the visual perceptions of the lightness of object colors than do values of Y; a is a coordinate denoting redness or greenness, for which positive values denote that the color is red rather than its opponent color green, and negative values of a denote the opposite; and b is a yellowness-blueness coordinate, for which positive values denote that the color is yellow rather than the opponent color blue, and negative values of b denote the opposite. For yellow colors, starting with a=b=0 and an appropriate high value of L, which would be a light grey, increasing positive values of b result in a series of colors that may be described as light yellowish grey, pale yellow, light yellow, brilliant yellow and vivid yellow, in turn. Thus b is a measure of the "intensity" of the yellow color.

Historically, all three Hunter values, a, b and L, have been utilized to describe a color. The inventors have determined that one can use the Hunter skin lightness measure L and comparative determinations of the Hunter value b developed at time intervals to measure the jaundice that is symptomatic of hyperbilirubinemia and by that measurement of jaundice detect the presence or absence of the ailment. The coordinate b provides a reliable measure of the yellow undertone of the color of human skin. This does not mean that Hunter a and Hunter L should be ignored, but they are not used in the usual way to define a color. In the particular arrangement of FIGS. 1 and 4, wherein the colorimeter 10 produces the values Y, x, y, the computer 15 derives the Hunter values L and b. The Hunter lightness skin color characteristic L affects the amount of increase in the yellow measure Hunter b that indicates hyperbilirubinemia. Following the procedure represented in FIG. 2, steps 1 to 4 and preferably using an averaging technique described below, a newborn is measured, preferably within 2–5 hours of birth, to establish the initial, baseline values of Hunter L and b, $L_0$ and $b_0$. The values are recorded, step 5, for example by placement in machine memory 17. (A baseline Hunter a, $a_0$, may be calculated at this time, too, for the purposes explained below and out of range values are discarded, i.e. 20>L>80, 2>a>50 and 2>b>40. Thereafter, again preferably using the averaging technique described below, throughout the next several days, Hunter L and b are measured at intervals as represented by step 6 of FIG. 2. L is compared to the value originally measured as indicated at step 7. It should not vary more than 3 to 5 points (depending on the range of L being measured) or the test is discontinued as at step 8. Otherwise, Hunter b is compared at step 9 to the baseline value established shortly after birth. As determined at step 10, if Hunter L remains consistent, if at any time Hunter b increases two points or more for skins with L values at or below approximately 51 or three points or more for skins with L values above approximately 51, then hyperbilirubinemia is indicated, a confirming blood test should be conducted, and phototherapy, the usual treatment for this condition, may be prescribed. Hunter b increases of one to two points for L values at or below approximately 51 and Hunter b increases of two to three points for L values above approximately 51 can be used as red flags or warning signs requiring closer monitoring.

When the measured value of Hunter L at any time is found to have varied more than 3–5 points the test procedure is suspect and the test may be discontinued. Hunter L variations of this magnitude do not ordinarily occur in skin color measurement. Unless this change can be explained by a change in the condition of the subject (such as anemia or phototherapy treatment, which would lighten the subjects entire skin color measurement and range, but in direct ratio of L and b) the test would be suspect and in which case an adjustment factor would be used to calculate L and b.

During phototherapy too, the testing procedure according to this invention can be used with an adjustment factor for the lightening of the skin color while under the phototherapy lights.

Figure 3:
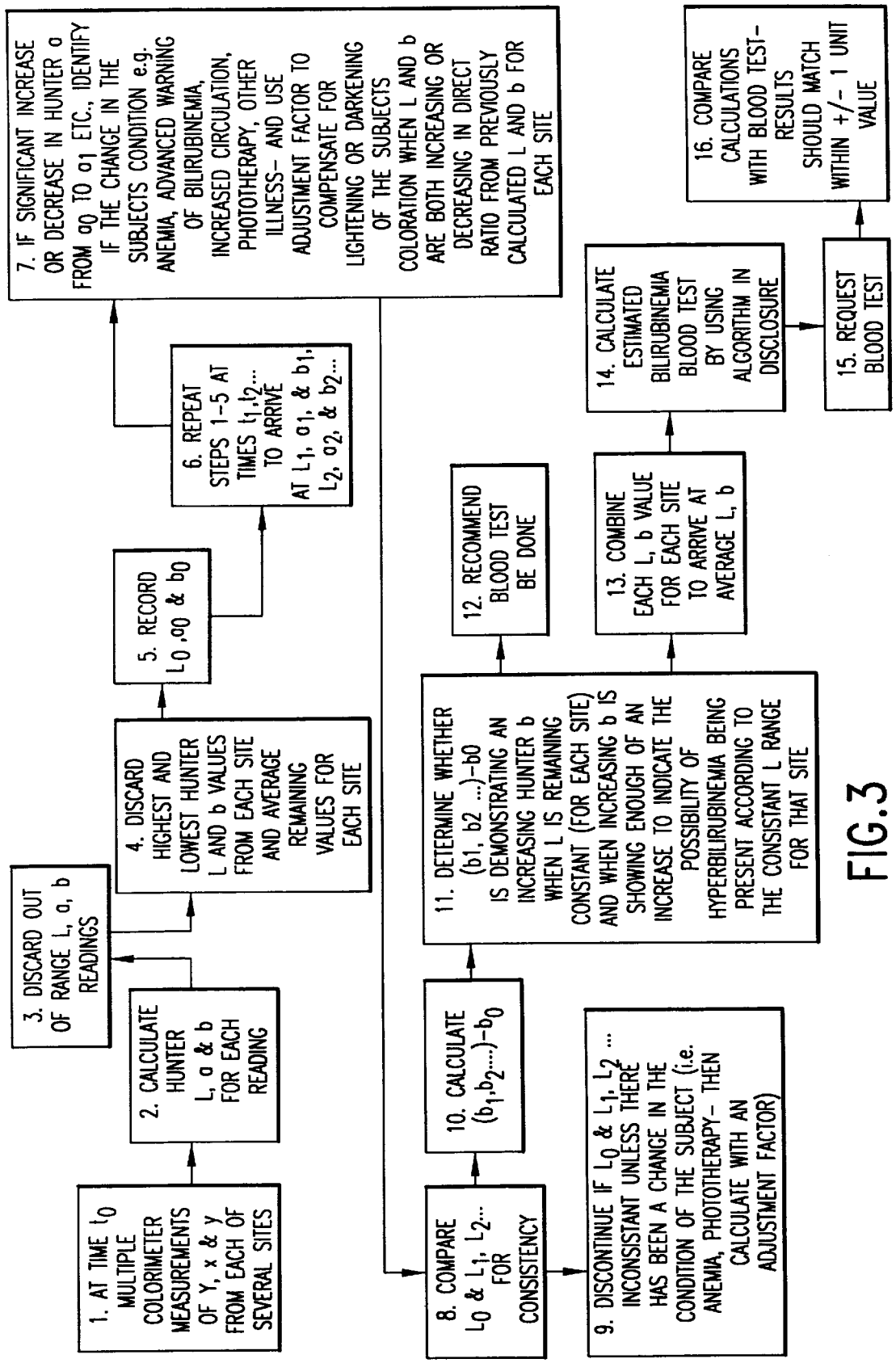
FIG. 3 is a schematic illustration in block diagram form illustrating the steps in the process of monitoring an infant for hyperbilirubinemia based on Hunter b including measuring and reviewing Hunter a as well as Hunter b and L.

As indicated, it has been the inventors' practice to require the additional measurement of Hunter a at each testing. This is illustrated in FIG. 3. Again the averaging technique is preferably used as described below. Based upon the testing of the skin color of several million individuals, the inventors have identified some 210 broad categories of skin coloration. That is to say, 210 broad ranges of Hunter L, a and b have been identified. Hunter L and b values for each of these categories are shown in Table II, set forth below. Table III, below, provides the ranges of Hunter a reasonably to be expected. For certain values of L, Hunter a above a particular value has not typically been observed. Should the test indicate a Hunter a outside any previously observed range for a particular L and b, this would be taken as at least a further indication of some disorder in a condition of the subject if the Hunter a value cannot otherwise be accounted for, e.g. from crying or drying after bathing. This occurrence is represented at step 7 of FIG. 3, which drawing figure represents the steps in the hyperbilirubinemia test that includes the measurement and comparison of Hunter a.

The measurement of Hunter a can have the further value of a warning that the jaundice associated with hyperbilirubinemia may shortly occur since, at times Hunter a will increase in value just before Hunter b increases.

If, then, an infant has not been crying (which boosts Hunter a), and an increase in Hunter a is observed, Hunter b bears watching for signs of hyperbilirubinemia.

TABLE II

| No. | Hunter L | Hunter b |
|---|---|---|
| 1. | <27 | −5* |
| 2. | <27 | 6 |
| 3. | <27 | 7 |
| 4. | <27 | 8 |
| 5. | <27 | 9 |
| 6. | <27 | 10 |
| 7. | <27 | 11 |
| 8. | <27 | 12+** |
| 9. | 27 to <30 | −5 |
| 10. | 27 to <30 | 6 |
| 11. | 27 to <30 | 7 |
| 12. | 27 to <30 | 8 |
| 13. | 27 to <30 | 9 |
| 14. | 27 to <30 | 10 |
| 15. | 27 to <30 | 11 |
| 16. | 27 to <30 | 12+ |
| 17. | 30 to <33 | −5 |
| 18. | 30 to <33 | 6 |
| 19. | 30 to <33 | 7 |
| 20. | 30 to <33 | 8 |
| 21. | 30 to <33 | 9 |
| 22. | 30 to <33 | 10 |
| 23. | 30 to <33 | 11 |
| 24. | 30 to <33 | 12+ |
| 25. | 33 to <36 | −5 |
| 26. | 33 to <36 | 6 |
| 27. | 33 to <36 | 7 |
| 28. | 33 to <36 | 8 |
| 29. | 33 to <36 | 9 |
| 30. | 33 to <36 | 10 |
| 31. | 33 to <36 | 11 |
| 32. | 33 to <36 | 12+ |
| 33. | 36 to <39 | −5 |
| 34. | 36 to <39 | 6 |
| 35. | 36 to <39 | 7 |
| 36. | 36 to <39 | 8 |
| 37. | 36 to <39 | 9 |
| 38. | 36 to <39 | 10 |
| 39. | 36 to <39 | 11 |
| 40. | 36 to <39 | 12 |
| 41. | 36 to <39 | 13 |
| 42. | 36 to <39 | 14 |
| 43. | 36 to <39 | 15+ |
| 44. | 39 to <42 | −5 |
| 45. | 39 to <42 | 6 |
| 46. | 39 to <42 | 7 |
| 47. | 39 to <42 | 8 |
| 48. | 39 to <42 | 9 |
| 49. | 39 to <42 | 10 |
| 50. | 39 to <42 | 11 |
| 51. | 39 to <42 | 12 |
| 52. | 39 to <42 | 13 |
| 53. | 39 to <42 | 14 |
| 54. | 39 to <42 | 15+ |
| 55. | 42 to <45 | −5 |
| 56. | 42 to <45 | 6 |
| 57. | 42 to <45 | 7 |
| 58. | 42 to <45 | 8 |
| 59. | 42 to <45 | 9 |
| 60. | 42 to <45 | 10 |
| 61. | 42 to <45 | 11 |
| 62. | 42 to <45 | 12 |
| 63. | 42 to <45 | 13 |
| 64 | 42 to <45 | 14 |
| 65. | 42 to <45 | 15 |
| 66. | 42 to <45 | 16 |
| 67. | 42 to <45 | 17 |
| 68. | 42 to <45 | 18+ |
| 69. | 45 to <48 | −5 |
| 70. | 45 to <48 | 6 |
| 71. | 45 to <48 | 7 |
| 72. | 45 to <48 | 8 |
| 73. | 45 to <48 | 9 |
| 74. | 45 to <48 | 10 |
| 75. | 45 to <48 | 11 |
| 76. | 45 to <48 | 12 |
| 77. | 45 to <48 | 13 |

TABLE II-continued

| No. | Hunter L | Hunter b |
|---|---|---|
| 78. | 45 to <48 | 14 |
| 79. | 45 to <48 | 15 |
| 80. | 45 to <48 | 16 |
| 81. | 45 to <48 | 17 |
| 82. | 45 to <48 | 18+ |
| 83. | 48 to <51 | −5 |
| 84. | 48 to <51 | 6 |
| 85. | 48 to <51 | 7 |
| 86. | 48 to <51 | 8 |
| 87. | 48 to <51 | 9 |
| 88. | 48 to <51 | 10 |
| 89. | 48 to <51 | 11 |
| 90. | 48 to <51 | 12 |
| 91. | 48 to <51 | 13 |
| 92. | 48 to <51 | 14 |
| 93. | 48 to <51 | 15 |
| 94. | 48 to <51 | 16 |
| 95. | 48 to <51 | 17 |
| 96. | 48 to <51 | 18 |
| 97. | 48 to <51 | 19 |
| 98. | 48 to <51 | 20+ |
| 99. | 51 to <54 | −5 |
| 100. | 51 to <54 | 6 |
| 101. | 51 to <54 | 7 |
| 102. | 51 to <54 | 8 |
| 103. | 51 to <54 | 9 |
| 104. | 51 to <54 | 10 |
| 105. | 51 to <54 | 11 |
| 106. | 51 to <54 | 12 |
| 107. | 51 to <54 | 13 |
| 108. | 51 to <54 | 14 |
| 109. | 51 to <54 | 15 |
| 110. | 51 to <54 | 16 |
| 111. | 51 to <54 | 17 |
| 112. | 51 to <54 | 18 |
| 113. | 51 to <54 | 19 |
| 114. | 51 to <54 | 20+ |
| 115. | 54 to <57 | −5 |
| 116. | 54 to <57 | 6 |
| 117. | 54 to <57 | 7 |
| 118. | 54 to <57 | 8 |
| 119. | 54 to <57 | 9 |
| 120. | 54 to <57 | 10 |
| 121. | 54 to <57 | 11 |
| 122. | 54 to <57 | 12 |
| 123. | 54 to <57 | 13 |
| 124. | 54 to <57 | 14 |
| 125. | 54 to <57 | 15 |
| 126. | 54 to <57 | 16 |
| 127. | 54 to <57 | 17 |
| 128. | 54 to <57 | 18 |
| 129. | 54 to <57 | 19 |
| 130. | 54 to <57 | 20+ |
| 131. | 57 to <60 | −5 |
| 132. | 57 to <60 | 6 |
| 133. | 57 to <60 | 7 |
| 134. | 57 to <60 | 8 |
| 135. | 57 to <60 | 9 |
| 136. | 57 to <60 | 10 |
| 137. | 57 to <60 | 11 |
| 138. | 57 to <60 | 12 |
| 139. | 57 to <60 | 13 |
| 140. | 57 to <60 | 14 |
| 141. | 57 to <60 | 15 |
| 142. | 57 to <60 | 16 |
| 143. | 57 to <60 | 17 |
| 144. | 57 to <60 | 18 |
| 145. | 57 to <60 | 19 |
| 146. | 57 to <60 | 20+ |
| 147. | 60 to <63 | −5 |
| 148. | 60 to <63 | 6 |
| 149. | 60 to <63 | 7 |
| 150. | 60 to <63 | 8 |
| 151. | 60 to <63 | 9 |
| 152. | 60 to <63 | 10 |
| 153. | 60 to <63 | 11 |
| 154. | 60 to <63 | 12 |
| 155. | 60 to <63 | 13 |
| 156. | 60 to <63 | 14 |
| 157. | 60 to <63 | 15 |
| 158. | 60 to <63 | 16 |
| 159. | 60 to <63 | 17 |
| 160. | 60 to <63 | 18 |
| 161. | 60 to <63 | 19 |
| 162. | 60 to <63 | 20+ |
| 163. | 63 to <66 | −5 |
| 164. | 63 to <66 | 6 |
| 165. | 63 to <66 | 7 |
| 166. | 63 to <66 | 8 |
| 167. | 63 to <66 | 9 |
| 168. | 63 to <66 | 10 |
| 169. | 63 to <66 | 11 |
| 170. | 63 to <66 | 12 |
| 171. | 63 to <66 | 13 |
| 172. | 63 to <66 | 14 |
| 173. | 63 to <66 | 15 |
| 174. | 63 to <66 | 16 |
| 175. | 63 to <66 | 17 |
| 176. | 63 to <66 | 18 |
| 177. | 63 to <66 | 19 |
| 178. | 63 to <66 | 20+ |
| 179. | 66 to <69 | −5 |
| 180. | 66 to <69 | 6 |
| 181. | 66 to <69 | 7 |
| 182. | 66 to <69 | 8 |
| 183. | 66 to <69 | 9 |
| 184. | 66 to <69 | 10 |
| 185. | 66 to <69 | 11 |
| 186. | 66 to <69 | 12 |
| 187. | 66 to <69 | 13 |
| 188. | 66 to <69 | 14 |
| 189. | 66 to <69 | 15 |
| 190. | 66 to <69 | 16 |
| 191. | 66 to <69 | 17 |
| 192. | 66 to <69 | 18 |
| 193. | 66 to <69 | 19 |
| 194. | 66 to <69 | 20+ |
| 195. | ≧69 | −5 |
| 196. | ≧69 | 6 |
| 197. | ≧69 | 7 |
| 198. | ≧69 | 8 |
| 199. | ≧69 | 9 |
| 200. | ≧69 | 10 |
| 201. | ≧69 | 11 |
| 202. | ≧69 | 12 |
| 203. | ≧69 | 13 |
| 204. | ≧69 | 14 |
| 205. | ≧69 | 15 |
| 206. | ≧69 | 16 |
| 207. | ≧69 | 17 |
| 208. | ≧69 | 18 |
| 209. | ≧69 | 19 |
| 210. | ≧69 | 20+ |

Wherein the designation −5 means less than 5 but more than 4 and the designation 12+ means more than 12 but less than 13.

TABLE III

| If Hunter L values are: | Then Hunter a values are: |
|---|---|
| 24 (or less) to 44 | 4 to 16 |
| 45 to 54 | 4 to 18 |
| 55 to 59 | 5 to 25 |
| 60 to 71 (or more) | 6 to 30 |

Figure 2:
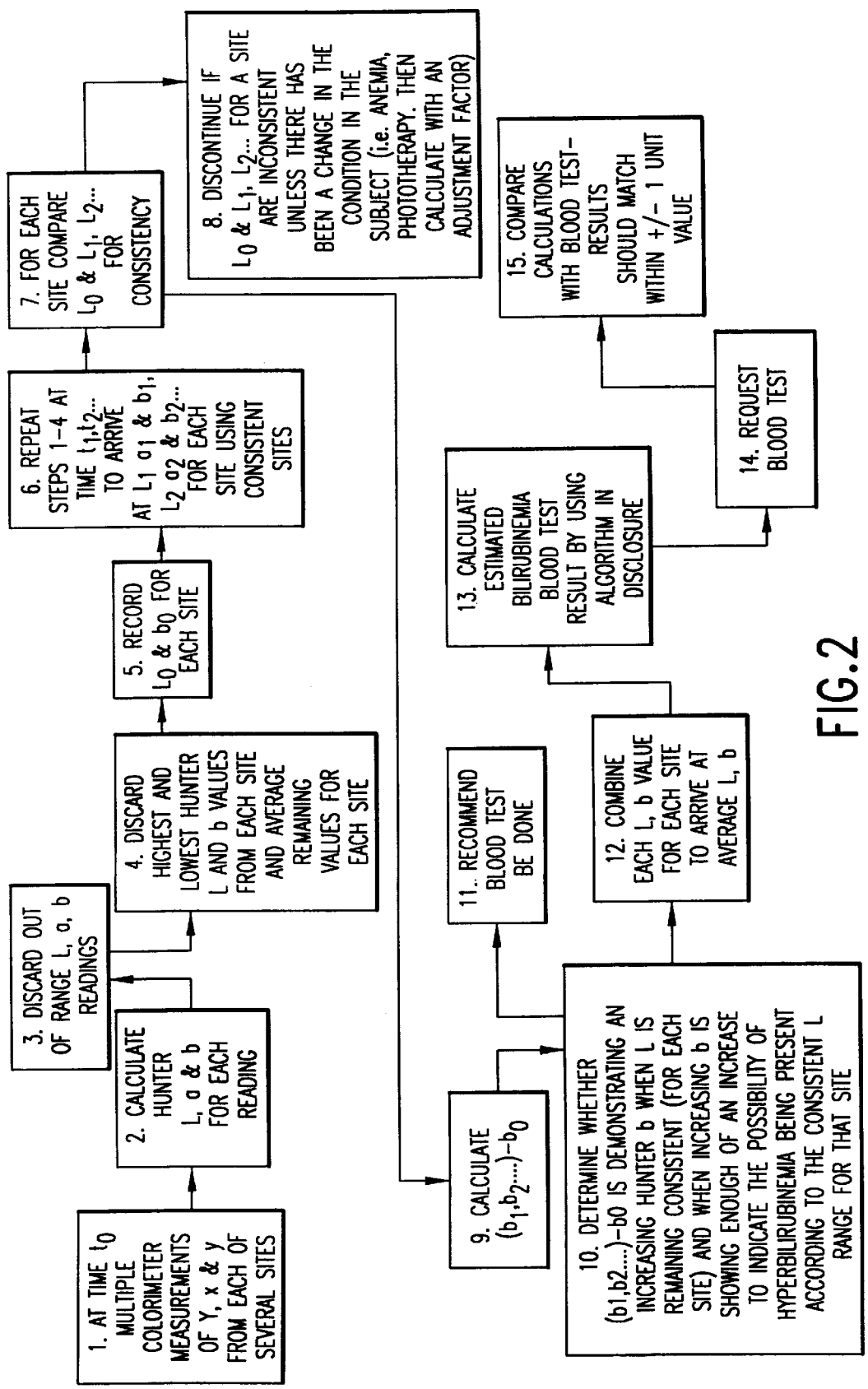
FIG. 2 is a schematic illustration in block diagram form illustrating the steps in the process of monitoring an infant for hyperbilirubinemia based upon changes in Hunter b in skin color and including measuring and reviewing Hunter b and L.

For greater accuracy, multiple Y, x and y readings are made with the colorimeter 10 at several different sites, for example at one or more locations on some or all of the subject's forehead, cheek, chest or back, as suggested in the steps of the method outlined in FIG. 2. In a preferred embodiment 5 or 6 readings at 5 different sites are made.

Hunter a, b and L values are calculated for each reading. The high and low values of a, b, and L from each site are discarded, the computer 15 then averages all of the remaining values of Hunter a, b and L for each site. The average a, b and L thus calculated for each site are then used as the Hunter b and L values in the previously described testing for bilirubinemia. If Hunter a is out of range for the site measured, this can also be an indicator of some disorder in the condition of a subject.

Some variation of b value occurs in dependence on the body location where readings are taken. Consistently averaging the values of Hunter a, b and L calculated from measurements taken at the same several locations on each individual can be used to eliminate any uncertainty resulting from such variations. The consistent measurement of consistent sites is essential throughout the entire procedure.

A hospital's measure of serum bilirubin typically uses a scale different from the measure of Hunter b detected by the above procedure. In extensive tests at one hospital, a linear relation was observed between serum bilirubin measured using the hospital's scale and the Hunter b measurement according to the invention. In that hospital 12 was the serum bilirubin value that signaled monitoring or treatment of hyperbilirubinemia. Steps 12–15 of FIG. 2 and 13–16 of FIG. 3 calculate the serum bilirubin level from the above procedures and compare it to the determination made by blood test.

Correlation between Hunter b and the hospital bilirubin count (BRC) was determined to be in accordance with the following equation:

$$BRC = 2.5([\{47/L\}^{1/2}b] - 6.8) \qquad (8)$$

where BRC equals the hospital bilirubin count, the number 47 is the average L for the entire database gathered over the course of research, and L and b are the average Hunter values determined as described above.

The term in braces modifies b according to the value L relative to its average, in this case 47, according to a square root (superscript ½) function. It may be easier to understand the above equation if it is written another way. If the modified b (in square brackets) is called MODB:

$$MODB = 6.8 + 0.4\ BRC \qquad (9)$$

The numbers 6.8 and 0.4 (=1/2.5) are, respectively, the intercept and slope of the straight line relation between modified b and BRC. The 6.8 is the value of MODB when BRC=0 and is related to the average baseline skin color. The 0.4 shows how rapidly MODB changes as BRC increases, an increase of 2.5 in BRC raises MODB by one point.

The equation is exemplary only and may vary in detail when applied to a larger database or to bilirubin count values from another hospital since hospitals do not have a standard scale used consistently from one hospital to the next. However, the linear relationship between MODB and BRC indicates relatively straightforward conversion of measured L and b to arrive at a particular hospital's bilirubin count value so that the medical practitioner can employ the optical measurement of jaundice in accordance with this invention in the same way she or he employed bilirubin count previously.

In the system of FIG. 1, following the routine of FIG. 2, from the initial measurement preferably within 2–5 hours of birth, the CPU calculates the initial Hunter values $L_0$, $a_0$ and $b_0$ and stores these in the Baseline Values addresses of the data portion or RAM of memory 17. The data RAM (or nonprogram) portion 18 of the memory 17 is indicated in FIG. 1A. A relatively permanent section 18a of RAM 18 stores the data of Table II (and Table III if Hunter a is to be checked) and data such as the ranges of L that establish categories of skin coloration for which varying Hunter b value changes are significant.

A more often revised memory segment stores the results of the measurements performed with the instrument. Based on a relatively straightforward program retained in the permanent ROM memory, from the measurements taken at intervals, the CPU calculates the new values of L, a, and b (or L and b to follow the procedure of FIG. 2), retrieves $L_0$, $a_0$ and $b_0$, and subtracts those from the new value $L_1$, $a_1$ and $b_1$. The change in Hunter L, a and b, $\Delta L$, $\Delta a$ and $\Delta b$, can be displayed, or preferably, the CPU determines if the change in L indicates an error by comparing the change in L to that value, stored in the RAM 18 of the memory 17, that raises the suspicion of test error. If there is no suspicion of error, then the CPU determines whether an increase in b is above the value, again stored in memory, that indicates monitoring or treatment of hyperbilirubinemia for the particular value of L that has been measured. Similarly, for an infant that has previously been diagnosed with hyperbilirubinemia and is undergoing phototherapy, the same order of decrease to within 2 or 3 points of baseline, depending on L, can indicate recovery and phototherapy may be ended. The CPU memory 17 can be provided with Table II, or another compilation of the categories of skin coloration, which the CPU then can use as a look-up table to determine if Hunter a has a value outside of previously observed ranges for the particular Hunter L and b. Also, if desired, the CPU can calculate and display the hospital's measure of serum bilirubin based upon changes in Hunter b, for example by applying equation 8 above.

Even in the absence of an initial reading, based on observed ranges of skin coloration, measurement of either Hunter L and b or L, a and b can warn of the likelihood of hyperbilirubinemia if a Hunter b value is measured that is in excess of Hunter b ordinarily observed for subjects with that value of L. Hunter b values exceeding those ordinarily observed for individuals in a particular range of Hunter L values can be determined by reference to Table II. For example, it will be apparent that no individual whose skin has a Hunter L value between 24 and 26 has measured above 13 in Hunter b. Such a measurement may be used to determine that a blood test is advisable. In all instances, however, even where there has not been a Hunter b baseline established, an increase over time of 2, 3 or more Hunter b points indicates the likelihood of hyperbilirubinemia, and if the change is a decrease, this is indicative of a recovering newborn.

Table IV is an actual set of measurements made on a three day old infant. Using the averaging technique described above, Hunter L of 48.0 and Hunter b of 11.1 is calculated. Converting to the hospital bilirubin count in the equation (9) above, a bilirubin count of 10.5 was calculated.

TABLE IV

|  | L | a | b | Y | x | y |
| --- | --- | --- | --- | --- | --- | --- |
| Forehead | 47.8 | 21.6 | 11.6 | 22.9 | 0.411 | 0.333 |
|  | 48.6 | 19.5 | 11.5 | 23.6 | 0.404 | 0.335 |
|  | 48.8 | 21.2 | 11.6 | 23.8 | 0.407 | 0.333 |
|  | 46.7 | 21.6 | 11.6 | 21.8 | 0.413 | 0.333 |
|  | 48.6 | 21.6 | 11.8 | 23.6 | 0.410 | 0.333 |
|  | 48.0 | 22.1 | 11.7 | 23.1 | 0.412 | 0.332 |
| Forehead | 46.4 | 20.5 | 11.2 | 21.5 | 0.409 | 0.333 |
|  | 46.0 | 20.3 | 11.1 | 21.1 | 0.409 | 0.333 |

TABLE IV-continued

|  | L | a | b | Y | x | y |
|---|---|---|---|---|---|---|
|  | 47.4 | 21.4 | 11.6 | 22.4 | 0.411 | 0.333 |
|  | 46.1 | 21.4 | 10.7 | 21.2 | 0.409 | 0.330 |
|  | 46.3 | 20.4 | 11.2 | 21.5 | 0.409 | 0.333 |
|  | 46.9 | 20.7 | 11.3 | 22.0 | 0.409 | 0.333 |
| Chest | 50.5 | 16.5 | 11.2 | 25.5 | 0.391 | 0.336 |
|  | 50.9 | 15.3 | 11.2 | 25.9 | 0.388 | 0.338 |
|  | 50.1 | 17.5 | 11.2 | 25.1 | 0.395 | 0.336 |
|  | 50.7 | 16.9 | 11.2 | 25.7 | 0.392 | 0.336 |
|  | 50.4 | 16.4 | 11.1 | 25.4 | 0.391 | 0.336 |
|  | 50.1 | 17.3 | 11.1 | 25.1 | 0.394 | 0.335 |
| Back | 49.0 | 17.1 | 11.1 | 24.0 | 0.395 | 0.336 |
|  | 48.7 | 16.3 | 11.0 | 23.7 | 0.394 | 0.337 |
|  | 48.3 | 16.6 | 10.6 | 23.3 | 0.393 | 0.335 |
|  | 49.2 | 16.6 | 10.9 | 24.2 | 0.393 | 0.336 |
|  | 49.1 | 18.3 | 11.3 | 24.1 | 0.399 | 0.335 |
|  | 50.0 | 18.0 | 11.4 | 25.0 | 0.397 | 0.336 |
| Back | 46.2 | 15.8 | 10.5 | 21.4 | 0.395 | 0.337 |
|  | 45.3 | 16.5 | 10.2 | 20.5 | 0.397 | 0.335 |
|  | 45.9 | 16.0 | 10.4 | 21.1 | 0.395 | 0.336 |
|  | 45.5 | 14.4 | 10.3 | 20.7 | 0.392 | 0.338 |
|  | 46.3 | 16.1 | 11.0 | 21.4 | 0.398 | 0.339 |
|  | 47.3 | 16.9 | 10.9 | 22.3 | 0.397 | 0.336 |

The invention can afford good evidence of jaundice resulting from medical conditions other than hyperbilirubinemia. Liver disorders in adults and children produce jaundice, for example. These and other skin color characteristics can be factors in diagnosing additional diseases that affect skin color. It has been observed, for example, that at least among dark skinned individuals, such as African Americans or others of African descent, skin color is affected by tuberculosis.

The application of the method and apparatus is not limited to the jaundice-related testing described above. Experiments with rhesus monkeys have shown a correlation between hormone levels and the coloration of the female monkey's very visible reddened hind end. An instrument like that described above was able to distinguish varying levels of reddening in an individual test subject's posterior using Hunter a and Hunter L in a similar fashion to that described above. The hormone level of the subject was thus indicated by the methods and apparatus of this invention.

Successful experimentation has begun on the evaluation of the condition of laboratory mice based upon the use of Hunter a and Hunter L in a similar fashion to that described above.

Table V is a broad categorization of human hair coloration.

TABLE V

| CATEGORY NAME | L Min | L Max | a Min | a Max | b Min | b Max |
|---|---|---|---|---|---|---|
| Black | 0.00 | 14.00 | −10.00 | 3.00 | −10.00 | 5.00 |
| Darkest Dark Brown | 14.00 | 16.00 | −10.00 | 3.00 | −10.00 | 1.00 |
| Darkest Dark Brown | 14.00 | 16.00 | −10.00 | 3.00 | 1.00 | 1.15 |
| Darkest Dark Brown | 14.00 | 16.00 | −10.00 | 3.00 | 1.15 | 1.25 |
| Darkest Dark Brown | 14.00 | 16.00 | −10.00 | 3.00 | 1.25 | 3.00 |
| Darker Dark Brown | 16.00 | 19.00 | −10.00 | 3.00 | −10.00 | 2.70 |
| Darker Dark Brown | 16.00 | 19.00 | −10.00 | 3.00 | 2.70 | 2.95 |
| Darker Dark Brown | 16.00 | 19.00 | −10.00 | 3.00 | 2.95 | 3.20 |
| Darker Dark Brown | 16.00 | 19.00 | −10.00 | 3.00 | 3.20 | 10.00 |
| Darker Dark Brown (Cool Auburn Tones) | 16.00 | 19.00 | 2.00 | 3.00 | −10.00 | 2.70 |
| Darker Dark Brown (Warm Auburn Tones) | 16.00 | 19.00 | 2.00 | 3.00 | 3.20 | 10.00 |
| Brown | 19.00 | 22.00 | 0.00 | 6.00 | −10.00 | 2.95 |
| Brown | 19.00 | 22.00 | 0.00 | 6.00 | 2.95 | 3.20 |
| Brown | 19.00 | 22.00 | 0.00 | 6.00 | 3.20 | 3.45 |
| Brown | 19.00 | 22.00 | 0.00 | 6.00 | 3.45 | 10.00 |
| Brown (Warm Auburn Tones) | 19.00 | 22.00 | 3.50 | 6.00 | 3.45 | 10.00 |
| Brown (Cool Auburn Tones) | 19.00 | 22.00 | 3.50 | 6.00 | −10.00 | 3.45 |
| Medium Brown | 22.00 | 27.00 | 1.00 | 6.00 | −10.00 | 3.75 |
| Medium Brown | 22.00 | 27.00 | 1.00 | 6.00 | 3.75 | 4.00 |
| Golden Med. Brown | 22.00 | 27.00 | 1.00 | 6.00 | 4.00 | 4.25 |
| Golden Med. Brown | 22.00 | 27.00 | 1.00 | 6.00 | 4.25 | 10.00 |
| Medium Brown (Warm Auburn Tones) | 22.00 | 27.00 | 3.50 | 6.00 | 4.25 | 10.00 |
| Medium Brown (Cool Auburn Tones) | 22.00 | 27.00 | 3.50 | 6.00 | −10.00 | 4.25 |
| Darkest Med. Blonde | 27.00 | 28.00 | 1.80 | 6.00 | −5.00 | 6.00 |
| Darkest Med. Blonde | 27.00 | 28.00 | 1.80 | 5.00 | 6.00 | 6.50 |
| Darkest Med. Blonde | 27.00 | 28.00 | 5.00 | 6.00 | 6.00 | 6.50 |
| Darkest Med. Blonde | 27.00 | 28.00 | 1.80 | 6.00 | 6.50 | 15.00 |
| Medium Blonde | 28.00 | 31.00 | 1.80 | 6.00 | −5.00 | 6.00 |
| Medium Blonde | 28.00 | 31.00 | 1.80 | 5.00 | 6.00 | 6.50 |
| Med. Golden Blonde | 28.00 | 31.00 | 5.00 | 6.00 | 6.00 | 6.50 |
| Med. Golden Blonde | 28.00 | 31.00 | 1.80 | 6.00 | 6.50 | 15.00 |
| Lightest Med. Blonde | 31.00 | 33.00 | 1.80 | 6.00 | −5.00 | 6.00 |
| Lightest Med. Blonde | 31.00 | 33.00 | 1.80 | 5.00 | 6.00 | 6.50 |
| Lightest Med. Blonde | 31.00 | 33.00 | 5.00 | 6.00 | 6.00 | 6.50 |
| Lightest Med. Blonde | 31.00 | 33.00 | 1.80 | 6.00 | 6.50 | 15.00 |
| Light Blonde | 33.00 | 36.00 | 1.80 | 6.00 | −5.00 | 7.00 |
| Light Blonde | 33.00 | 36.00 | 1.80 | 5.00 | 7.00 | 7.50 |
| Light Blonde | 33.00 | 36.00 | 5.00 | 6.00 | 7.00 | 7.50 |
| Light Blonde | 33.00 | 36.00 | 1.80 | 6.00 | 7.50 | 20.00 |
| Lighter Blonde | 36.00 | 40.00 | 1.80 | 6.00 | −5.00 | 8.00 |
| Lighter Blonde | 36.00 | 40.00 | 1.80 | 5.00 | 8.00 | 8.50 |
| Lighter Blonde | 36.00 | 40.00 | 5.00 | 6.00 | 8.00 | 8.50 |
| Lighter Blonde | 36.00 | 40.00 | 1.80 | 6.00 | 8.50 | 20.00 |
| Lightest Blonde | 40.00 | 80.00 | 1.80 | 7.00 | −5.00 | 9.00 |
| Lightest Blonde | 40.00 | 80.00 | 1.80 | 5.00 | 9.00 | 10.00 |
| Lightest Blonde | 40.00 | 80.00 | 5.00 | 7.00 | 9.00 | 10.00 |
| Lightest Blonde | 40.00 | 80.00 | 1.80 | 7.00 | 10.00 | 30.00 |
| Light Red | 22.00 | 28.00 | 6.00 | 30.00 | 5.00 | 3.50 |
| Light Red | 22.00 | 28.00 | 6.00 | 30.00 | 3.50 | 3.75 |
| Light Red | 22.00 | 28.00 | 6.00 | 30.00 | 3.75 | 4.00 |
| Light Red | 22.00 | 28.00 | 6.00 | 30.00 | 4.00 | 30.00 |
| Medium Red | 19.00 | 22.00 | 6.00 | 30.00 | 10.00 | 3.50 |
| Medium Red | 19.00 | 22.00 | 6.00 | 30.00 | 3.50 | 3.75 |
| Med. Golden Red | 19.00 | 22.00 | 6.00 | 30.00 | 3.75 | 4.00 |
| Med. Golden Red | 19.00 | 22.00 | 6.00 | 30.00 | 4.00 | 30.00 |
| Dark Red | 14.00 | 19.00 | 3.00 | 30.00 | −10.00 | 2.50 |
| Dark Red | 14.00 | 19.00 | 3.00 | 30.00 | 2.50 | 2.75 |
| Dark Red | 14.00 | 19.00 | 3.00 | 30.00 | 2.75 | 3.00 |
| Dark Red | 14.00 | 19.00 | 3.00 | 30.00 | 3.00 | 30.00 |
| Red Blonde | 27.00 | 40.00 | 6.00 | 30.00 | 6.00 | 30.00 |
| Red Blonde | 40.00 | 80.00 | 7.00 | 30.00 | 6.00 | 30.00 |
| Black/Dk Brown/ Med/Brown/Brown w/ 70%–90% Grey | 27.00 | 50.00 | −10.00 | 1.80 | −10.00 | 3.75 |

TABLE V-continued

| CATEGORY NAME | L Min | L Max | a Min | a Max | b Min | b Max |
|---|---|---|---|---|---|---|
| Black/Dk Brown/Med Brown/Brown w/ 70%–90% Grey | 27.00 | 50.00 | –10.00 | 1.80 | 3.75 | 4.00 |
| Black/Dk Brown/Med Brown/Brown w/ 70%–90% Grey | 27.00 | 50.00 | –10.00 | 1.80 | 4.00 | 4.25 |
| Black/Dk Brown/Med Brown/Brown w/ 70%–90% Grey | 27.00 | 50.00 | –10.00 | 1.80 | 4.25 | 10.00 |
| Black/Dk Brown/Med Brown/Brown w/ 40%–60% Grey | 23.00 | 27.00 | –10.00 | 1.00 | –10.00 | 3.75 |
| Black/Dk Brown/Med Brown/Brown w/40%–60% Grey | 23.00 | 27.00 | –10.00 | 1.00 | 3.75 | 4.00 |
| Black/Dk Brown/Med Brown/Brown w/40%–60% Grey | 23.00 | 27.00 | –10.00 | 1.00 | 4.00 | 4.25 |
| Black/Dk Brown/Med Brown/Brown w/ 40%–60% Grey | 23.00 | 27.00 | –10.00 | 1.00 | 4.25 | 10.00 |
| *For Grey Hair* | | | | | | |
| Light Brown/Darkest Blonde | | | | | | |
| 40%–60% Grey | 4.00 | 10.00 | –10.00 | –0.08 | | |
| 70%–90% Grey | 10.00 | To Maximum | –10.00 | –0.08 | | |
| Dark Red, Medium Red or Medium Light Red | | | | | | |
| 40%–60% Grey | 6.00 | 10.00 | –10.00 | –0.80 | | |
| 70%–90% Grey | 10.00 | To Maximum | –10.00 | –0.80 | | |
| Light Red or Red Blonde | | | | | | |
| 40%–60% Grey | 5.00 | 7.00 | –10.00 | –0.80 | | |
| 70%–90% Grey | 7.00 | To Maximum | –10.00 | –0.80 | | |
| Medium to Medium Dark Blonde | | | | | | |
| 40%–60% Grey | 1.70 | 4.00 | 0.00 | 0.00 | | |
| 70%–90% Grey | 4.00 | To Maximum | 0.00 | 0.00 | | |
| Light Blonde Hair | | | | | | |
| 40%–60% Grey | –99.99 | –0.25 | –1.75 | –1.25 | | |
| 70%–90% Grey | –99.99 | –0.25 | –99.99 | –1.75 | | |

*Wherein negative values denote values less than zero.

In addition to diagnostic use, test procedures and instruments according to this invention can be used to determine how to restore the hair to its natural color, or with reference to the categories of Table V or VI, hair that has changed in color by greying or by bleaching or dying can be restored to a more natural appearance, whether the test subject's original coloring or a chosen color consistent with the limitation of the categories identified in Table V or VI. In the particular arrangement of FIG. 4, wherein the colorimeter 10 produces the values Y, x and y, the computer 15 derives the Hunter values L, a and b. Following the procedure represented in FIG. 5, the colorimeter is calibrated as described above. The values of Y, x and y are measured for each of multiple sites on the subject's hair. Preferably the top, each side, the back of the subject's head, the color of the hair at the roots and at its ends, are measured. Three measurements are taken at each site and are averaged to arrive at an Y, x and y for each site and, from the average for each site, Hunter L, a and b for each site are calculated.

The following discussion references tables VI through XII. Due to their length, those tables are produced at the end of the specification for the sake of clarity.

The values of Hunter L, a and b are compared to the values of Hunter L, a and b of the color categories 1, 2, 3, 4, 5, 6 etc. of the Hair Categories table of Table VI. This, then, identifies the category of the subject's hair coloring at each of the measured sites. Each Hair Category in the table of Table VI has in association with it the hair color name, such as Black-Cool, Darkest Dark Brown-Cool, etc., an identification of one or more manufacturer's "Levels" which are commonly indicated upon a manufacturer's product to indicate products recommended for individuals with particular hair color. In other words, the identification of hair category or classification can also indicate to the subject or the subject's hair specialist the designation or level that the subject should seek out in a particular manufacturer's line of products. The Hair Categories illustrated in Table VI may further identify for the subject or his or her specialist the pigment designation given by the manufacturers to the particular color.

The hair color categories for the several measured sites, then, can be used by the subject or her or his hair specialist to allow for accurate assessment of the hair color to be dyed and to choose product for hair coloring. As will be appreciated, the category or classification may vary from site to site and this will inform the subject or specialist whether it will be necessary to use varying products or longer or shorter periods of application at varying sites to achieve a hair coloration desired. In other words, dark roots might be treated differently than light ends.

Figure 6:
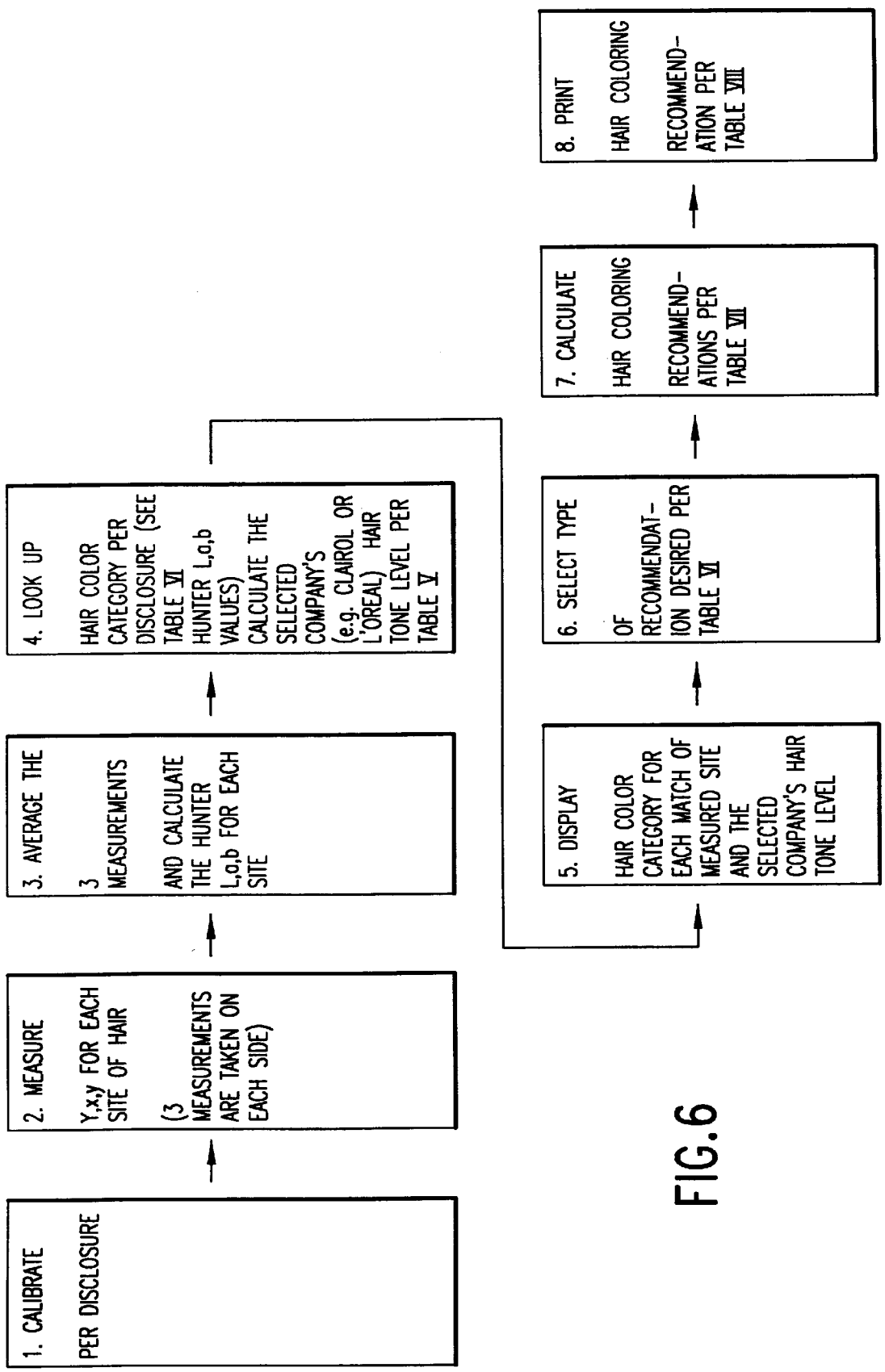
FIG. 6 is a schematic illustration in block diagram form illustrating the steps in the process of using hair color classification and a database to arrive at a coloring agent for making a selected alteration in hair color.

In accordance with the further method according to FIG. 6, a hair coloring agent recommendation is made to achieve a subject's desired coloration change. Once having determined the correct color categories for each measured site, a menu of possible actions (Table VII) affecting hair color is displayed and one such action in chosen by the subject or hair specialist. Using that selection and the hair color category, a database (Table VIII) is consulted as indicated at step 7 and at step 8 products are identified from Table IX of a given manufacturer that will accomplish the sought-after result.

The menu of hair color action choices available in step 6 is listed in Table VII.

The database used in step 7 to arrive at a particular product that will effect the chosen hair color option for the particular person's hair category is shown in Table VIII. Certain codes in this appendix that are used by this database require explanation. The same 75 hair color categories 1, 2, 3, 4, etc., and category names as appear in Table VI are listed under the heading "Category Name." Also under "Category Name" the Category Group, A, B, C, D, etc. is designated as in Table VI. Next, the ranges of Hunter L, a and b defining the category appear. Under the heading "CW Level" one of four levels of cool to warm is listed. In these the numeral "1" is coolest, "2" is a border color on the cool side of the cool-warm boundary, "3" is a warm color on the warm side of the cool-warm boundary, and "4" is a warm color. The "Level" column lists again the product manufacturer's "Level" designations like those listed in Table VI.

In the database illustrated in Table VIII, two manufacturers are listed for each category. Opposite each appears a series of numbers such as −1:01−2:01+1:02+2:02. In each of these numbers the first digit represents an action which may be chosen from the menu of hair color options. For example in −1:01, the number "−1" making hair color slightly darker. The number "−2" means "darker," which is somewhat more darkening than "slightly darker." The number "+1" means "slightly lighter" and the number "+2" means "lighter," e.g. somewhat more lightening than "slightly lighter." The number after the (:), "01," is a direction to go to category group A. In category Group A, then, are identified the manufacturer products of :011. An index, listed in Table IX, identifies products of each manufacturer. These are the products that will have the desired effect.

From the database of Table VIII it will be seen, then, that, for example, to darken hair of Categories 2, 3, 4 and S, "01" appears, making reference to Category Group A1.

The database appended as Table VIII was developed empirically by, first, measuring the Hunter L, a and b of an enormous number of sample hairs from the numerous Categories, then applying the colorants of the manufacturers to these hairs and again measuring the Hunter L, a and b to determine the color change effect of the hairs thus colored. This was done as well for the lighter ends of these hairs and for darker roots. This was also done for greying hair for use in the grey hair program described below. In this fashion the database of Table VIII was built.

Figure 7:
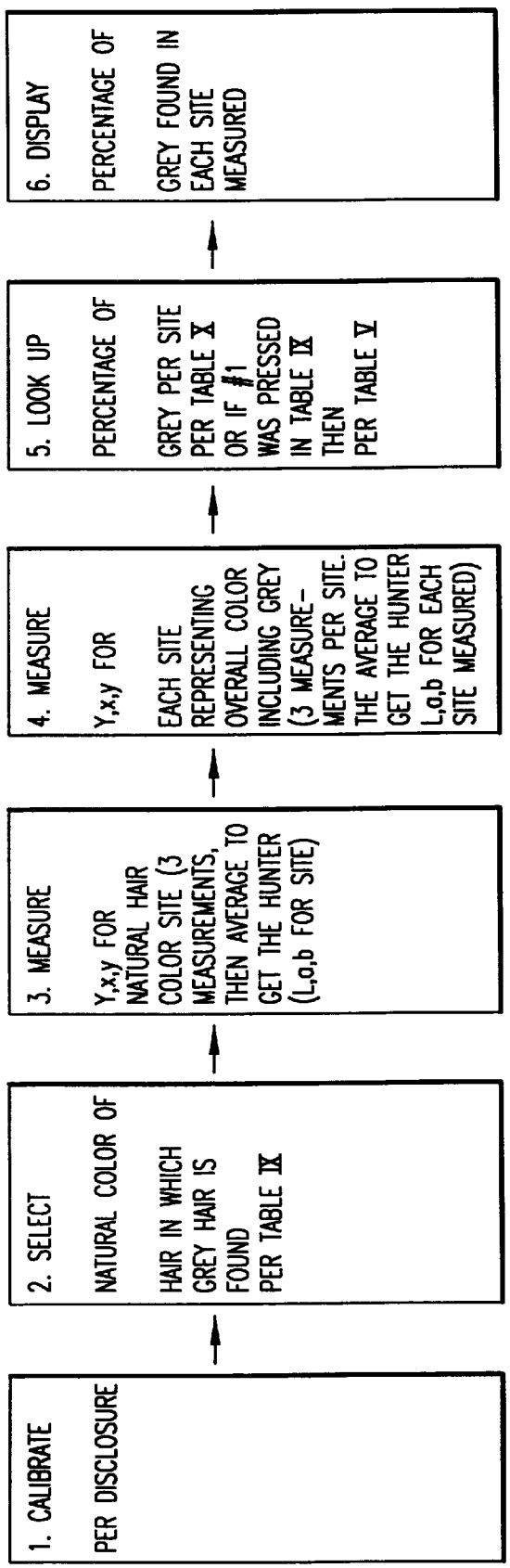
FIG. 7 is a schematic illustration in block diagram form illustrating the steps in the process of arriving at hair color classification of a greying individual.

Turning to the block diagram of FIG. 7, characterization of greying hair can be accomplished, following calibration of the instrument at step one, by selecting one's natural color from the following List Of Natural Hair Color Options. (Table X).

Again, at step three Y, x and y for the natural hair is identified, either by measurement at a natural hair color site on the individual or by the individual's identifying hair swatches considered to be his or her natural color. From Y, x and y, Hunter L, a and b—three measurements are taken and then averaged to reach average Hunter L, a and b, or in the case of the swatch this may already have been done so that Hunter L, a and b for the swatch is known.

Further sites containing grey are then measured at step 4 to arrive at Y, x and y for these additional sites, which again may be the sides, top, back of the head, roots and ends. The same procedure is followed with three measurements per site to reach average Y, x and y for each site and thereafter calculating average L, a and b for each site. With the Hunter L, a and b for natural hair and the Hunter L, a and b for the greying hair determined, the table entitled "Calculation of Percentage of Grey Hair." Table XI, is consulted, which defines the grey hair categories on the basis of percentage of grey.

The percentage grey thus identified is displayed and this represents the category for an individual with greying hair. This characterization is used similarly to the previously described characterization or category of the table of hair categories shown in Table V or VI.

Figure 8:
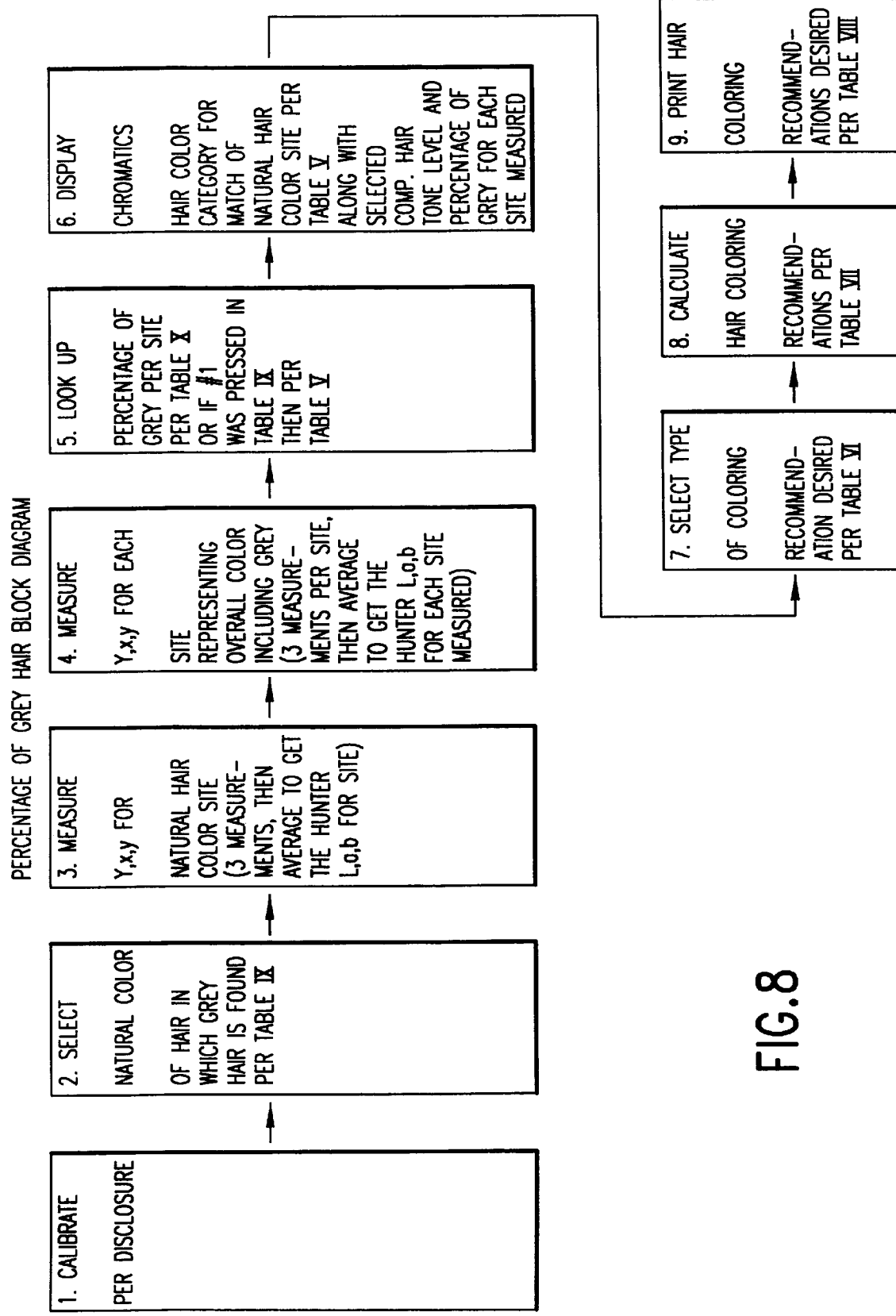
FIG. 8 is a schematic illustration in block diagram form illustrating the steps in the process of using hair color classification of a greying individual and a database to arrive at a coloring agent for making selected alteration in hair color.

In FIG. 8 the use of the grey hair identification as just described in a procedure for identifying colorants to achieve a desired result is indicated. After calibration of the instrument as described, the steps previously discussed in connection with FIG. 7 are followed to identify the category of greying hair. Then, at step 7 from the menu of options appearing in Table VII, a selection of one of the 35 choices is made. With that, now the database of Table VIII can be used in exactly the same manner as described previously. That is to say, the category of hair is found, the option selected is chosen as −1, −2, +1 or +2. The Category Group designator, 01, 02, 03, etc. is used to identify the appropriate category family to go to and in that category family is found the identifier of manufacturer's hair colorants that will produce the desired result which is found in Table IX.

Figure 9:
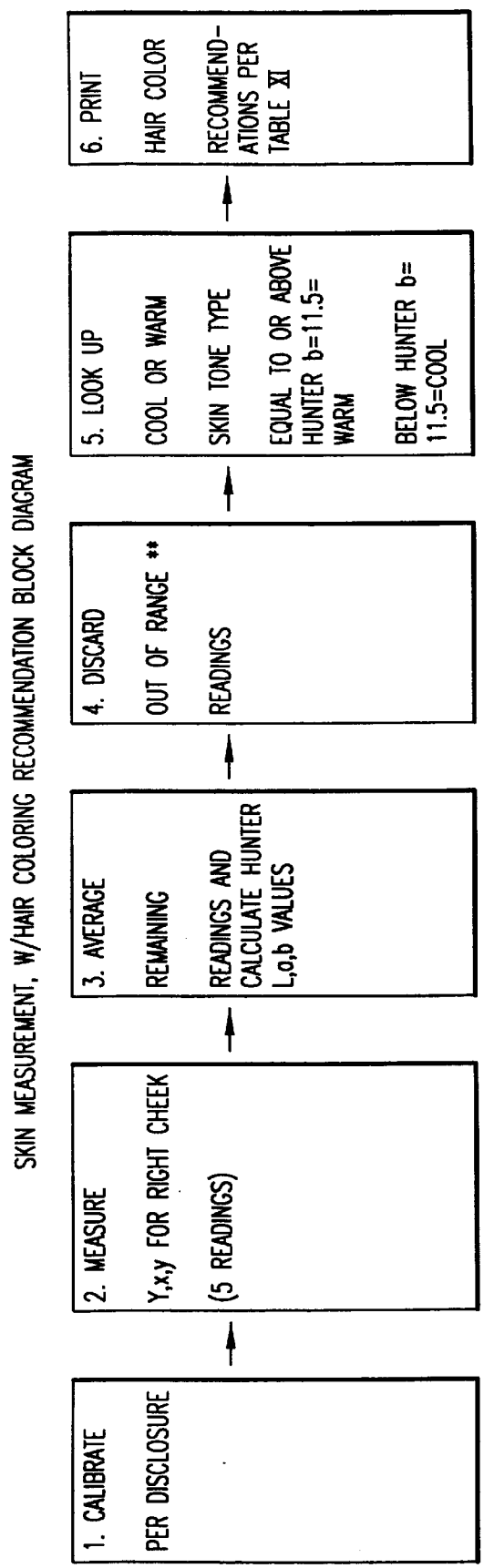
FIG. 9 is a schematic illustration in block diagram form illustrating the steps in the process of arriving at hair color treatment agents based upon a database of agents and individual skin color characteristics.

In FIG. 9 a method of using an indicator table to choose hair coloring agents for compatibility with skin coloration entails taking 5 measurements for the subjects right cheek and calculating Y, x and y, following calibration of the instrument. Out of range readings are discarded prior to calculation of Hunter L, a and b based on the remaining three averaged Y, x and y readings. Using the value of Hunter b at step 5 it is determined whether the skin tone type is less than 11.5 and consequently cool or equal to or higher than 11.5 and therefore warm. Using this cool or warm designation, Table XI is consulted to arrive at hair color recommendations.

Table XI is developed by assessment of Hunter b in the products listed to assess the warmness or coolness of those products and products are recommended that have the same proportion of yellow to blue as does the measured skin color.

In FIG. 4 the colorimeter 10 provides Y, x and y to the computer 15. The computer's memory 17 is divided into RAM and ROM.

Figure 4A:
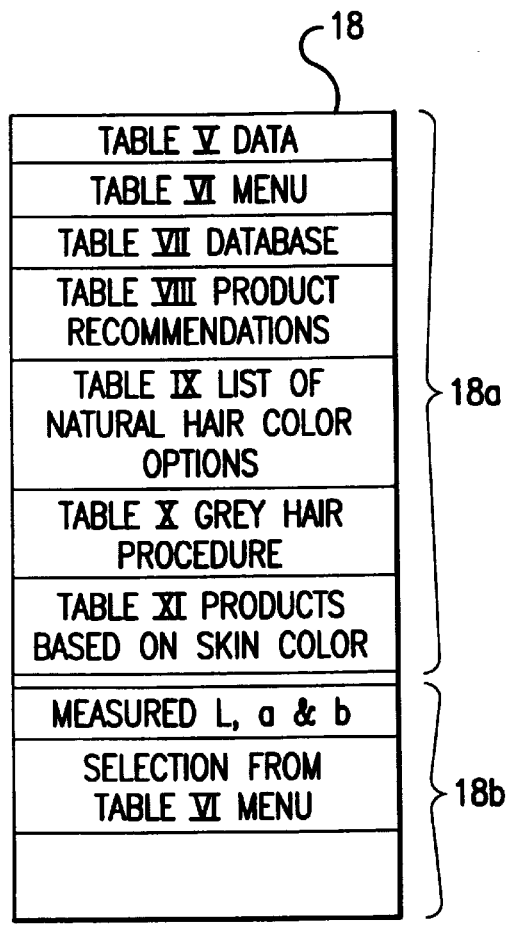
FIG. 4A is a diagrammatic illustration of exemplary memory content in an instrument like that of FIG. 4.
Figure 5:
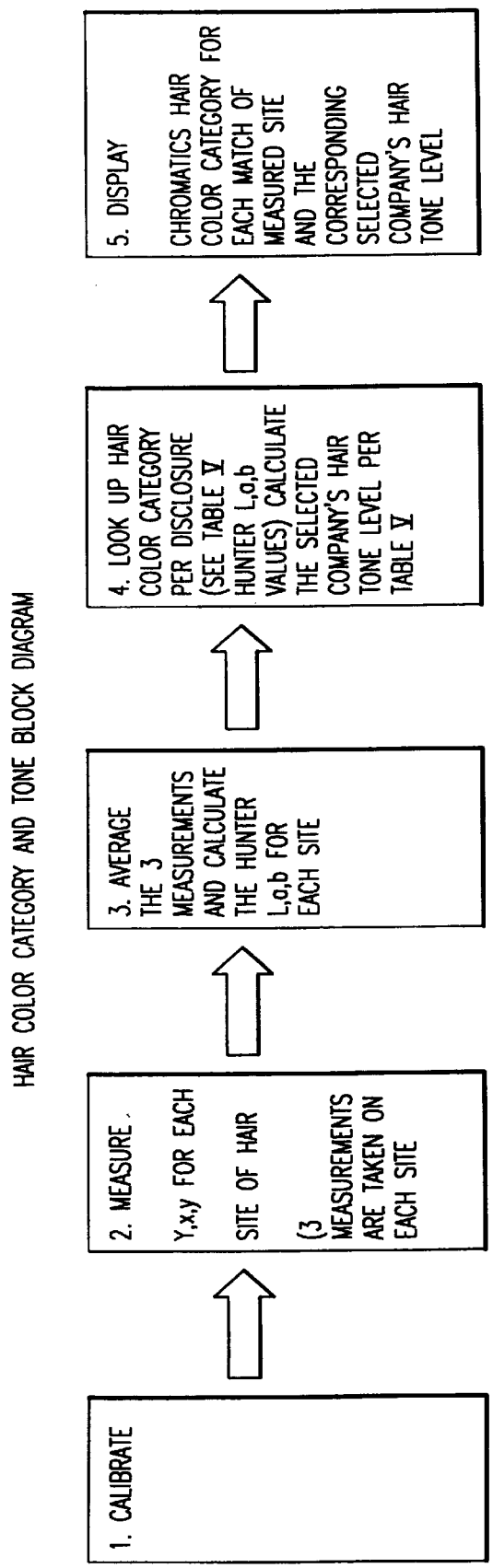
FIG. 5 is a schematic illustration in block diagram form illustrating the steps in the process of arriving at hair color classification of an individual.

In the system of FIG. 4, following the routine of FIG. 5, the CPU or central processing unit of the computer calculates the Hunter values L, a and b and stores these at selected addresses of the data portion or RAM state of memory 17. The data RAM (or nonprogram) portion 18 of the memory 17 is indicated in FIG. 4A. A relatively permanent section 18a of RAM 18 stores the data of Table VI. A more often revised memory segment stores the results of the measurements performed with the instrument. Based on a relatively straightforward program retained in the permanent ROM memory, from the measurements taken at intervals, the CPU calculates new values of L, a and b. The CPU compares these to the L, a and b values in Table VI and indicates the appropriate hair color category from Table VI, for example on the display 20.

To perform the procedure according to FIG. 6, the RAM memory 18 also contains the information of the menu of options in Table VII. These are called up and displayed at display 20 and, using an input device such as a keyboard 22 or a mouse, a selection is made. The selection in retained in the more temporary portion 18b of the RAM 18.

The CPU consults the Table VIII database, in the more permanent RAM section 18a and pulls up the appropriate manufacturer's product identifications in Table IX, for the choice of menu items and the hair color category. These are displayed on the display 20.

To accomplish the procedure of FIG. 7 the RAM 18 retains the Table VI information which includes the greying hair categories 61 to 68 and the Table XI information giving the manner of arriving at percentage of grey hair. The CPU inquires of the user via the display or measurement and is given the natural hair color via the input. The CPU uses the Hunter L, a and b values and Table VI to determine Color Category or if Table VI does not yield a category the Table XI information is employed with L to arrive at a Category using Table XI. The category is displayed.

To perform the procedures of FIG. 8, the CPU determines the category-percentage of grey hair as above, from either Table VI or Table XI. The menu of selections, Table VII, is displayed and a choice is indicated. Using the choice and the category identified, the Table VIII database is used to indicate a group or "file" of manufacturer's products in Table IX, which are then displayed on the display 20.

For the choice of hair coloring agent based on skin color the CPU determines if Hunter b is above or below 11.5 and based on this available selections from Table XII are chosen and displayed.

In much the same way as described for hair and skin coloration, tooth coloration can be assessed by this invention and the techniques described can be used to arrive at a natural coloring of replacement dental work consistent with existing or replacement teeth.

Plant and crop specimens are good candidates for the application of the procedures and apparatus of the invention. For example, conditions leading to the degradation of grain stored in silos are observable based upon color change. Determination of these conditions by instrument is made possible by the techniques of the present invention, and this opens the way to automated monitoring for this purpose. Soil samples from oil spills when measured by these procedures and apparatus indicate the degree of soil contamination by oil or gasoline. Testing of such soil contamination has been successfully conducted. Biological test subjects of a great variety can be tested by means of the present invention. Such test subjects include, for example, hair, teeth, tissue, excretions, foods, soils, animals and plants.

From the foregoing it should be apparent that the methods and apparatus described are exemplary and not intended to limit the scope of protection of the invention as set forth in the appended claims.

TABLE VI

HAIR CATEGORIES

| | | CATEGORY NAME | L Min | L Max | a Min | a Max | b Min | b Max | Level | Clairol Pigmt | Level | L'Oreal Pigmt |
|---|---|---|---|---|---|---|---|---|---|---|---|---|
| 1 | A | Black-Cool | 0.00 | 14.00 | −10.00 | 3.00 | −10.00 | 5.00 | 1 | Red Brown | M1 | None |
| 2 | B | Darkest Dark Brown-Cool | 14.00 | 16.00 | −10.00 | 3.00 | −10.00 | 1.00 | 2 | Red Brown | M3 | None |
| 3 | B | Darkest Dark Brown-Border C/W-C | 14.00 | 16.00 | −10.00 | 3.00 | 1.00 | 1.15 | 2 | Red Brown | M3 | None |
| 4 | B | Darkest Dark Brown-Border C/W-W | 14.00 | 16.00 | −10.00 | 3.00 | 1.15 | 1.25 | 2 | Red Brown | M3 | None |
| 5 | B | Darkest Dark Brown-Warm | 14.00 | 16.00 | −10.00 | 3.00 | 1.25 | 3.00 | 2 | Red Brown | M3 | None |
| 6 | C | Darker Dark Brown-Cool | 16.00 | 19.00 | −10.00 | 3.00 | −10.00 | 2.70 | 2 | Red Orange | M4 | Red |
| 7 | C | Darker Dark Brown-Border C/W C | 16.00 | 19.00 | −10.00 | 3.00 | 2.70 | 2.95 | 3 | Red Orange | M4 | Red |
| 8 | C | Darker Dark Brown-Border C/W W | 16.00 | 19.00 | −10.00 | 3.00 | 2.95 | 3.20 | 3 | Red Orange | M4 | Red |
| 9 | C | Darker Dark Brown-Warm | 16.00 | 19.00 | −10.00 | 3.00 | 3.20 | 10.00 | 3 | Red Orange | M4 | Red |
| | | FLAG: Darker Dark Brown (Auburn Tones-Cool) | 16.00 | 19.00 | 2.00 | 3.00 | −10.00 | 2.70 | 3 | Red Orange | M4 | Red |
| | | Darker Dark Brown (Auburn Tones-Warm) | 16.00 | 19.00 | 2.00 | 3.00 | 3.20 | 10.00 | 3 | Red Orange | M4 | Red |
| 10 | D | Brown-Cool | 19.00 | 22.00 | 0.00 | 6.00 | −10.00 | 2.95 | 4 | Red Orange | M5 | Red Orange |
| 11 | D | Brown-Border C/W-C | 19.00 | 22.00 | 0.00 | 6.00 | 2.95 | 3.20 | 4 | Red Orange | M5 | Red Orange |
| 12 | D | Brown-Border C/W-W | 19.00 | 22.00 | 0.00 | 6.00 | 3.20 | 3.45 | 4 | Red Orange | M5 | Red Orange |
| 13 | D | Brown-Warm | 19.00 | 22.00 | 0.00 | 6.00 | 3.45 | 10.00 | 4 | Red Orange | M5 | Red Orange |
| | | FLAG: Brown (Auburn Tones-Warm) | 19.00 | 22.00 | 3.50 | 6.00 | 3.45 | 10.00 | 4 | Red Orange | M5 | Red Orange |
| | | Brown (Auburn Tones-Cool) | 19.00 | 22.00 | 3.50 | 6.00 | −10.00 | 3.45 | 4 | Red Orange | M5 | Red Orange |
| 14 | E | Medium Brown-Cool | 22.00 | 27.00 | 1.00 | 6.00 | −10.00 | 3.75 | 5 | Orange | M6 | Orange |
| 15 | E | Medium Brown-Border C/W C | 22.00 | 27.00 | 1.00 | 6.00 | 3.75 | 4.00 | 5 | Orange | M6 | Orange |
| 16 | E | Golden Med. Brown-Border C/W W | 22.00 | 27.00 | 1.00 | 6.00 | 4.00 | 4.25 | 5 | Orange | M6 | Orange |
| 17 | E | Golden Med. Brown-Warm | 22.00 | 27.00 | 1.00 | 6.00 | 4.25 | 10.00 | 5 | Orange | M6 | Orange |
| | | FLAG: Medium Brown (Auburn Tones-Warm) | 22.00 | 27.00 | 3.50 | 6.00 | 4.25 | 10.00 | 5 | Orange | M6 | Orange |
| | | Medium Brown (Auburn Tones-Cool) | 22.00 | 27.00 | 3.50 | 6.00 | −10.00 | 4.25 | 5 | Orange | M6 | Orange |
| 18 | F | Darkest Med Blonde-Cool | 27.00 | 28.00 | 1.80 | 6.00 | −5.00 | 6.00 | 6 | Gold Orange | M7 | Yellow Orange |
| 19 | F | Darkest Med. Blonde-Border C/W C | 27.00 | 28.00 | 1.80 | 5.00 | 6.00 | 6.50 | 6 | Gold Orange | M7 | Yellow Orange |
| 20 | F | Darkest Med. Blonde-Border C/W W | 27.00 | 28.00 | 5.00 | 6.00 | 6.00 | 6.50 | 6 | Gold Orange | M7 | Yellow Orange |
| 21 | F | Darkest Med. Blonde-Warm | 27.00 | 28.00 | 1.80 | 6.00 | 6.50 | 15.00 | 6 | Gold Orange | M7 | Yellow Orange |
| 22 | G | Medium Blonde-Cool | 28.00 | 31.00 | 1.80 | 6.00 | −5.00 | 6.00 | 6 | Gold Orange | M8 | Yellow |
| 23 | G | Medium Blonde-Border C/W C | 28.00 | 31.00 | 1.80 | 5.00 | 6.00 | 6.50 | 6 | Gold Orange | M8 | Yellow |
| 24 | G | Med. Golden Blonde-Border C/W W | 28.00 | 31.00 | 5.00 | 6.00 | 6.00 | 6.50 | 6 | Gold Orange | M8 | Yellow |

TABLE VI-continued

HAIR CATEGORIES

| | CATEGORY NAME | L Min | L Max | a Min | a Max | b Min | b Max | Clairol Level | Clairol Pigmt | L'Oreal Level | L'Oreal Pigmt |
|---|---|---|---|---|---|---|---|---|---|---|---|
| 25 G | Med. Golden Blonde-Warm | 28.00 | 31.00 | 1.80 | 6.00 | 6.50 | 15.00 | 6 | Gold Orange | M8 | Yellow |
| 26 H | Lightest Med. Blonde-Cool | 31.00 | 33.00 | 1.80 | 6.00 | −5.00 | 6.00 | 7 | Gold | M8 | Yellow |
| 27 H | Lightest Med. Blonde-Border C/W C | 31.00 | 33.00 | 1.80 | 5.00 | 6.00 | 6.50 | 7 | Gold | M8 | Yellow |
| 28 H | Lightest Med. Blonde-Border C/W W | 31.00 | 33.00 | 5.00 | 6.00 | 6.00 | 6.50 | 7 | Gold | M8 | Yellow |
| 29 H | Lightest Med. Blonde-Warm | 31.00 | 33.00 | 1.80 | 6.00 | 6.50 | 15.00 | 7 | Gold | M8 | Yellow |
| 30 I | Light Blonde-Cool | 33.00 | 36.00 | 1.80 | 6.00 | −5.00 | 7.00 | 7 | Gold | M9 | Pale Yellow |
| 31 I | Light Blonde-Border C/W C | 33.00 | 36.00 | 1.80 | 5.00 | 7.00 | 7.50 | 7 | Gold | M9 | Pale Yellow |
| 32 I | Light Blonde-Border C/W W | 33.00 | 36.00 | 5.00 | 6.00 | 7.00 | 7.50 | 7 | Gold | M9 | Pale Yellow |
| 33 I | Light Blonde-Warm | 33.00 | 36.00 | 1.80 | 6.00 | 7.50 | 20.00 | 7 | Gold | M9 | Pale Yellow |
| 34 J | Lighter Blonde-Cool | 36.00 | 40.00 | 1.80 | 6.00 | −5.00 | 8.00 | 8 | Deep Yellow | M9 | Pale Yellow |
| 35 J | Lighter Blonde-Border C/W C | 36.00 | 40.00 | 1.80 | 5.00 | 8.00 | 8.50 | 8 | Deep Yellow | M9 | Pale Yellow |
| 36 J | Lighter Blonde-Border C/W W | 36.00 | 40.00 | 5.00 | 6.00 | 8.00 | 8.50 | 8 | Deep Yellow | M9 | Pale Yellow |
| 37 J | Lighter Blonde-Warm | 36.00 | 40.00 | 1.80 | 6.00 | 8.50 | 20.00 | 8 | Deep Yellow | M9 | Pale Yellow |
| 38 K | Lightest Blonde-Cool | 40.00 | 80.00 | 1.80 | 7.00 | −5.00 | 9.00 | 9 | Pale Yellow | M10 | Pale Yellow |
| 39 K | Lightest Blonde-Border C/W C | 40.00 | 80.00 | 1.80 | 5.00 | 9.00 | 10.00 | 9 | Pale Yellow | M10 | Pale Yellow |
| 40 K | Lightest Blonde-Border C/W-W | 40.00 | 80.00 | 5.00 | 7.00 | 9.00 | 10.00 | 9 | Pale Yellow | M10 | Pale Yellow |
| 41 K | Lightest Blonde-Warm | 40.00 | 80.00 | 1.80 | 7.00 | 10.00 | 30.00 | 9 | Pale Yellow | M10 | Pale Yellow |
| 42 L | Lightest Blonde-Cool | 50.00 | 80.00 | 1.80 | 7.00 | −5.00 | 9.00 | 10 | Pale Yellow | M10 | Pale Yellow |
| 43 L | Lightest Blonde-Border C/W C | 50.00 | 80.00 | 1.80 | 5.00 | 9.00 | 10.00 | 10 | Pale Yellow | M10 | Pale Yellow |
| 44 L | Lightest Blonde-Border C/W W | 50.00 | 80.00 | 5.00 | 7.00 | 9.00 | 10.00 | 10 | Pale Yellow | M10 | Pale Yellow |
| 45 L | Lightest Blonde-Warm | 50.00 | 80.00 | 1.80 | 7.00 | 10.00 | 30.00 | 10 | Pale Yellow | M10 | Pale Yellow |
| 46 M | Light Red-Cool | 22.00 | 28.00 | 6.00 | 30.00 | −5.00 | 3.50 | 5 (with Red Violet, Neutral or Blue Violet tones) | Orange | M6 (with Ash, Irridescent or Auburn tones) | Orange |
| 47 M | Light Red-Border C/W C | 22.00 | 28.00 | 6.00 | 30.00 | 3.50 | 3.75 | 5 (with Red Violet, Neutral or Blue Violet tones) | Orange | M6 (with Ash, Irridescent or Auburn tones) | Orange |
| 48 M | Light Red-Border C/W W | 22.00 | 28.00 | 6.00 | 30.00 | 3.75 | 4.00 | 5 (with Red, Gold or Red Orange tones) | Orange | M6 (with Gold or Copper tones) | Orange |
| 49 M | Light Red-Warm | 22.00 | 28.00 | 6.00 | 30.00 | 4.00 | 30.00 | 5 (with Red, Gold or Red Orange tones) | Orange | M6 (with Gold or Copper tones) | Orange |
| 50 N | Medium Red-Cool | 19.00 | 22.00 | 6.00 | 30.00 | −10.00 | 3.50 | 4 (with Red, Violet, Neutral or Blue | Red Orange | M5 (with Ash, Irridescent or Auburn tones) | Red Orange |

TABLE VI-continued

HAIR CATEGORIES

| | CATEGORY NAME | L Min | L Max | a Min | a Max | b Min | b Max | Clairol Level | Clairol Pigmt | L'Oreal Level | L'Oreal Pigmt |
|---|---|---|---|---|---|---|---|---|---|---|---|
| 51 N | Medium Red-Border C/W C | 19.00 | 22.00 | 6.00 | 30.00 | 3.50 | 3.75 | 4 (with Red Violet, Neutral or Blue Violet tones) | Red Orange | M5 (with Ash, Irridescent or Auburn tones) | Red Orange |
| 52 N | Med. Golden Red-Border C/W W | 19.00 | 22.00 | 6.00 | 30.00 | 3.75 | 4.00 | 4 (with Red, Gold or Red Orange tones) | Red Orange | M5 (with Gold or Copper tones) | Red Orange |
| 53 N | Med. Golden Red-Warm | 19.00 | 22.00 | 6.00 | 30.00 | 4.00 | 30.00 | 4 (with Red, Gold or Red Orange tones) | Red Orange | M5 (with Gold or Copper tones) | Red Orange |
| 54 O | Dark Red-Cool | 14.00 | 19.00 | 3.00 | 30.00 | −10.00 | 2.50 | ⅔ (with Red Violet, Neutral or Blue tones) | Red | M4 (with Orange Irridescent or Auburn tones) | Red Orange Ash, |
| 55 O | Dark Red-Border C/W C | 14.00 | 19.00 | 3.00 | 30.00 | 2.50 | 2.75 | ⅔ (with Red Violet, Neutral or Blue Violet tones) | Red Orange | M4 (with Ash, Irridescent or Auburn tones) | Red Orange |
| 56 O | Dark Red-Border C/W W | 14.00 | 19.00 | 3.00 | 30.00 | 2.75 | 3.00 | ⅔ (with Red, Gold or Red Orange tones) | Red Orange | M4 (with Gold or Copper tones) | Red Orange |
| 57 O | Dark Red Warm | 14.00 | 19.00 | 3.00 | 30.00 | 3.00 | 30.00 | ⅔ (with Red, Gold or Red Orange tones) | Red Orange | M4 (with Gold or Copper tones) | Red Orange |
| 58 P | Red Blonde | 27.00 | 40.00 | 6.00 | 30.00 | 6.00 | 30.00 | 6/7/8 (with Red, Gold or Red Orange tones) | Yellow | M7/M8 (with Gold or Copper tones) | Yellow |
| 59 Q | Red Blonde | 40.00 | 80.00 | 7.00 | 30.00 | 6.00 | 30.00 | 9/10 (with Red, Gold or Red Orange tones) | Pale Yellow | M9 (with Gold or Copper tones) | Pale Yellov |
| 60 R | Red Blond | 50.00 | 80.00 | 7.00 | 30.00 | 6.00 | 30.00 | 9/10 (with Red, Gold or Red Orange tones) | Pale Yellow | M9 (with Gold or Copper tones) | Pale Yellow |
| 61 S | Black/Dk Brown/Med Brown/Brown w/70%–90% Grey-Cool | 27.00 | 50.00 | −10.00 | 1.80 | −10.00 | 3.75 | | | | |
| 62 S | Black/Dk Brown/Med Brown/Brown | 27.00 | 50.00 | −10.00 | 1.80 | 3.75 | 4.00 | | | | |

TABLE VI-continued

HAIR CATEGORIES

| | CATEGORY NAME | L Min | L Max | a Min | a Max | b Min | b Max | Clairol Level | Clairol Pigmt | L'Oreal Level | L'Oreal Pigmt |
|---|---|---|---|---|---|---|---|---|---|---|---|
| | w/70%–90% Grey-Border C/W-C | | | | | | | | | | |
| 63 S | Black/Dk Brown/Med Brown/Brown w/70%–90% Grey-Border C/W-W | 27.00 | 50.00 | −10.00 | 1.80 | 4.00 | 4.25 | | | | |
| 64 S | Black/Dk Brown/Med Brown/Brown w/70%–90% Grey-Warm | 27.00 | 50.00 | −10.00 | 1.80 | 4.25 | 10.00 | | | | |
| 65 T | Black/Dk Brown/Med Brown/Brown w/40%–60% Grey-Cool | 23.00 | 27.00 | −10.00 | 1.00 | −10.00 | 3.75 | | | | |
| 66 T | Black/Dk Brown/Med Brown/Brown w/40%-60% Grey-Border C/W-C | 23.00 | 27.00 | −10.00 | 1.00 | 3.75 | 4.00 | | | | |
| 67 T | Black/Dk Brown/Med Brown/Brown w/40%–60% Grey-Border C/W-W | 23.00 | 27.00 | −10.00 | 1.00 | 4.00 | 4.25 | | | | |
| 68 T | Black.Dk Brown/Med Brown/Brown w/40%–60% Grey-Warm | 23.00 | 27.00 | −10.00 | 1.00 | 4.25 | 10.00 | | | | |
| | For Grey Hair | | | | | | | | | | |
| | Light Brown/Darkest Blonde | | | | | | | | | | |
| | 40%–60% Grey | 4.00 | 10.00 | −10.00 | −0.08 | | | | | | |
| | 70%–90% Grey | 10.00 | To Maximum | −10.00 | −0.08 | | | | | | |
| | Dark Red, Medium Red or Medium Light Red | | | | | | | | | | |
| | 40%–60% Grey | 6.00 | 10.00 | −10.00 | −0.80 | | | | | | |
| | 70%–90% Grey | 10.00 | To Maximum | −10.00 | −0.80 | | | | | | |
| | Light Red or Red Blonde | | | | | | | | | | |
| | 40%–60% Grey | 5.00 | 7.00 | −10.00 | −0.80 | | | | | | |
| | 70%–90% Grey | 7.00 | To Maximum | −10.00 | −0.80 | | | | | | |
| | Medium to Medium Dark Blonde | | | | | | | | | | |
| | 40%–60% Grey | 1.70 | 4.00 | 0.00 | 0.00 | | | | | | |
| | 70%–90% Grey | 4.00 | To Maximum | 0.00 | 0.00 | | | | | | |
| | Light Blonde Hair | | | | | | | | | | |
| | 40%–60% Grey | −9.99 | −0.25 | −1.75 | −1.25 | | | | | | |
| | 70%–90% Grey | −9.99 | −0.25 | −9.99 | −1.75 | | | | | | |

*Wherein negative values denote values less than zero.

TABLE VII

MENU OF HAIR COLOR OPTIONS

1. Match Natural Hair Color
2. Make Natural Hair Color Warmer
3. Make Natural Hair Color Cooler
4. Highlight Natural Hair Color
5. Make Natural Hair Color Slightly Darker
6. Make Natural Hair Color Slightly Lighter
7. Make Natural Hair Color Darker
8. Make Natural Hair Color Lighter
9. Make Natural Hair Color Warmer and Slightly Darker
10. Make Natural Hair Color Warmer and Slightly Lighter
11. Make Natural Hair Color Warmer and Darker
12. Make Natural Hair Color Warmer and Lighter
13. Make Natural Hair Color Cooler and Slightly Darker
14. Make Natural Hair Color Cooler and Slightly Lighter
15. Make Natural Hair Color Cooler and Darker
16. Make Natural Hair Color Cooler and Lighter
17. Make Natural Hair Color Warmer with Highlights
18. Make Natural Hair Color Cooler with Highlights
19. Make Tinted Hair Color Warmer
20. Make Tinted Hair Color Cooler
21. Highlight Tinted Hair Color
22. Make Tinted Hair Color Slightly Darker
23. Make Tinted Hair Color Slightly Lighter
24. Make Tinted Hair Color Darker
25. Make Tinted Hair Color Lighter
26. Make Tinted Hair Color Warmer and Slightly Darker
27. Make Tinted Hair Color Warmer and Slightly Lighter
28. Make Tinted Hair Color Warmer and Darker
29. Make Tinted Hair Color Warmer and Lighter
30. Make Tinted Hair Color Cooler and Slightly Darker
31. Make Tinted Hair Color Cooler and Slightly Lighter

TABLE VII-continued

MENU OF HAIR COLOR OPTIONS

| | |
|---|---|
| 32. | Make Tinted Hair Color Cooler and Darker |
| 33. | Make Tinted Hair Color Cooler and Lighter |
| 34. | Make Tinted Hair Color Warmer with Highlights |
| 35. | Make Tinted Hair Color Cooler with Highlights |

TABLE VIII

DATABASE

| Category Name | LMin | LMax | aMin | aMax | bMin | bMax | CW | Level | | | | | | |
|---|---|---|---|---|---|---|---|---|---|---|---|---|---|---|
| 1.A BLACK-COOL | 0.00 | 14.00 | −10.00 | 3.00 | −10.00 | 5.00 | 1 | 1 | | | | | | |
| Clairol: #1 | | | | | | | | | −1:01 | −2:01 | +1:02 | +2:02 | Pig.:1 | File:011 |
| L'Oreal: M1 | | | | | | | | | −1:01 | −2:01 | +1:02 | +2:02 | Pig.:0 | File:011 |
| 2.B. DARKEST DARK BROWN - COOL | 14.00 | 16.00 | −10.00 | 3.00 | −10.00 | 1.00 | 1 | 2 | | | | | | |
| Clairol: #2 | | | | | | | | | −1:01 | −2:01 | +1:03 | +2:03 | Pig.:1 | File:021 |
| L'Oreal: M3 | | | | | | | | | −1:01 | −2:01 | +1:03 | +2:03 | Pig.:0 | File:021 |
| 3.B. DARKEST DARK BROWN - BORDER C/W - COOL | 14.00 | 16.00 | −10.00 | 3.00 | 1.00 | 1.15 | 2 | 2 | | | | | | |
| Clairol: #2 | | | | | | | | | −1:01 | −2:01 | +1:03 | +2:03 | Pig.:1 | File:021 |
| L'Oreal: M3 | | | | | | | | | −1:01 | −2:01 | +1:03 | +2:03 | Pig.:0 | File:021 |
| 4.B. DARKEST DARK BROWN - BORDER C/W - WARM | 14.00 | 16.00 | −10.00 | 3.00 | 1.15 | 1.25 | 3 | 2 | | | | | | |
| Clairol: #2 | | | | | | | | | −1:01 | −2:01 | +1:03 | +2:03 | Pig.:1 | File:000 |
| L'Oreal: M3 | | | | | | | | | −1:01 | −2:01 | +1:03 | +2:03 | Pig.:0 | File:024 |
| 5.B. DARKEST DARK BROWN - WARM | 14.00 | 16.00 | −10.00 | 3.00 | 1.25 | 3.00 | 4 | 2 | | | | | | |
| Clairol: #2 | | | | | | | | | −1:01 | −2:01 | +1:03 | +2:03 | Pig.:1 | File:000 |
| L'Oreal: M3 | | | | | | | | | −1:01 | −2:01 | +1:03 | +2:03 | Pig.:0 | File:024 |
| 6.C. DARKER DARK BROWN - COOL | 16.00 | 15.00 | −10.00 | 2.00 | −10.00 | 2.70 | 1 | 3 | | | | | | |
| Clairol: #3 | | | | | | | | | −1:02 | −2:02 | +1:04 | +2:04 | Pig.:2 | File:031 |
| L'Oreal: M4 | | | | | | | | | −1:02 | −2:02 | +1:04 | +2:04 | Pig.:1 | File:031 |
| 7.C. DARKER DARK BROWN - BORDER C/W - COOL | 16.00 | 19.00 | −10.00 | 2.00 | 2.70 | 2.95 | 2 | 3 | | | | | | |
| Clairol: #3 | | | | | | | | | −1:02 | −2:02 | +1:04 | +2:04 | Pig.:2 | File:031 |
| L'Oreal: M4 | | | | | | | | | −1:02 | −2:02 | +1:04 | °2:04 | Pig:1 | File:031 |
| 8.C. DARKER DARK BROWN - BORDER C/W - WARM | 16.00 | 19.00 | −10.00 | 2.00 | 2.95 | 3.20 | 3 | 3 | | | | | | |
| Clairol: #3 | | | | | | | | | −1:02 | −2:02 | +1:04 | +2:04 | Pig.:2 | File:034 |
| L'Oreal: M4 | | | | | | | | | −1:02 | −2:02 | +1:04 | +2:04 | Pig.:1 | File:034 |
| 9.C. DARKER DARK BROWN - WARM | 16.00 | 19.00 | −10.00 | 2.00 | 3.20 | 10.00 | 4 | 3 | | | | | | |
| Clairol: #3 | | | | | | | | | −1:02 | −2:02 | +1:04 | +2:04 | Pig.:2 | File:034 |
| L'Oreal: M4 | | | | | | | | | −1:02 | −2:02 | +1:04 | +2:04 | Pig.:1 | File:034 |
| 10.C. DARKER DARK BROWN (AUBURN TONES) - COOL | 16.00 | 19.00 | 2.00 | 3.00 | −10.00 | 3.20 | 1 | 3 | | | | | | |
| Clairol: #3 | | | | | | | | | −1:02 | −2:02 | +1:04 | +2:04 | Pig.:2 | File:031 |
| L'Oreal: M4 | | | | | | | | | −1:02 | −2:02 | +1:04 | +2:04 | Pig.:1 | File:031 |
| 11.C. DARKER DARK BROWN (AUBURN TONES) - WARM | 16.00 | 19.00 | 2.00 | 3.00 | 3.20 | 10.00 | 4 | 3 | | | | | | |
| Clairol: #3 | | | | | | | | | −1:02 | −2:02 | +1:04 | +2:04 | Pig.:2 | File:034 |
| L'Oreal: M4 | | | | | | | | | −1:02 | −2:02 | +1:04 | +2:04 | Pig.:1 | File:034 |
| 13.D. BROWN-COOL | 19.00 | 22.00 | 0.00 | 3.50 | −10.00 | 2.95 | 1 | 4 | | | | | | |
| Clairol: #4 | | | | | | | | | −1:03 | −2:03 | +1:05 | +2:05 | Pig.:2 | File:041 |
| L'Oreal: M5 | | | | | | | | | −1:03 | −2:03 | +1:05 | +2:05 | Pig.:2 | File:041 |
| 14.D. BROWN- BORDER C/W - COOL | 19.00 | 22.00 | 0.00 | 3.50 | 2.95 | 3.20 | 2 | 4 | | | | | | |
| Clairol: #3 | | | | | | | | | −1:03 | −2:03 | +1:05 | +2:05 | Pig.:2 | File:041 |
| L'Oreal: M5 | | | | | | | | | −1:03 | −2:03 | +1:05 | +2:05 | Pig.:2 | File:041 |
| 15.D. BROWN- BORDER C/W - WARM | 19.00 | 22.00 | 0.00 | 3.50 | 3.20 | 3.45 | 3 | 4 | | | | | | |
| Clairol: #4 | | | | | | | | | −1:03 | −2:03 | +1:05 | +2:05 | Pig.:2 | File:044 |
| L'Oreal: M5 | | | | | | | | | −1:03 | −2:03 | +1:05 | +2:05 | Pig.:2 | File:044 |
| 16.D. BROWN - WARM | 19.00 | 22.00 | 0.00 | 3.50 | 3.45 | 10.00 | 4 | 4 | | | | | | |
| Clairol: #4 | | | | | | | | | −1:03 | −2:03 | +1:05 | +2:05 | Pig.:2 | File:044 |

TABLE VIII-continued

DATABASE

| Category Name | LMin | LMax | aMin | aMax | bMin | bMax | CW | Level | | | | | | |
|---|---|---|---|---|---|---|---|---|---|---|---|---|---|---|
| L'Oreal: M5 | | | | | | | | | −1:03 | −2:03 | +1:05 | +2:05 | Pig.:2 | File:044 |
| 17.D. BROWN (AUBURN TONES) - COOL | 19.00 | 22.00 | 3.50 | 6.00 | −10.00 | 3.45 | 1 | 4 | | | | | | |
| Clairol: #4 | | | | | | | | | −1:03 | −2:03 | +1:05 | +2:05 | Pig.:2 | File:041 |
| L'Oreal: M5 | | | | | | | | | −1:03 | −2:03 | +1:05 | +2:05 | Pig.:2 | File:041 |
| 18.D. BROWN (AUBURN TONES) - WARM | 19.00 | 22.00 | 3.50 | 6.00 | 3.45 | 10.00 | 4 | 4 | | | | | | |
| Clairol:#4 | | | | | | | | | −1:03 | −2:03 | +1:05 | +2:05 | Pig.:2 | File:044 |
| L'Oreal: M5 | | | | | | | | | −1:03 | −2:03 | +1:05 | +2:05 | Pig.:2 | File:044 |
| 19.E. MEDIUM BROWN - COOL | 22.00 | 27.00 | 1.00 | 3.50 | −10.00 | 3.75 | 1 | 5 | | | | | | |
| Clairol: #5 | | | | | | | | | −1:04 | −2:04 | +1:06 | +2:06 | Pig.:3 | File:051 |
| L'Oreal: M6 | | | | | | | | | −1:04 | −2:04 | +1:06 | +2:06 | Pig.:3 | File:051 |
| 20.E. MEDIUM BROWN BORDER C/W - COOL | 22.00 | 27.00 | 1.00 | 3.50 | 3.75 | 4.00 | 2 | 5 | | | | | | |
| Clairol: #5 | | | | | | | | | −1:04 | −2:04 | +1:06 | +2:06 | Pig.:3 | File:051 |
| L'Oreal: M6 | | | | | | | | | −1:04 | −2:04 | +1:06 | +2:06 | Pig.:3 | File:051 |
| 21.E. MEDIUM BROWN (G) BORDER C/W - WARM | 22.00 | 27.00 | 1.00 | 3.50 | 4.00 | 4.25 | 3 | 5 | | | | | | |
| Clairol: #5 | | | | | | | | | −1:04 | −2:04 | +1:06 | +2:06 | Pig.:3 | File:054 |
| L'Oreal: M6 | | | | | | | | | −1:04 | −2:04 | +1:06 | +2:06 | Pig.:3 | File:054 |
| 22.E. MEDIUM BROWN(G) - WARM | 22.00 | 27.00 | 1.00 | 3.50 | 4.25 | 10.00 | 4 | 5 | | | | | | |
| Clairol: #5 | | | | | | | | | −1:04 | −2:04 | +1:06 | +2:06 | Pig.:3 | File:054 |
| L'Oreal: M6 | | | | | | | | | −1:04 | −2:04 | +1:06 | +2:06 | Pig.:3 | File:054 |
| 23.E. MEDIUM BROWN (AUBURN TONES) - COOL | 22.00 | 27.00 | 3.50 | 6.00 | −10.00 | 4.25 | 1 | 5 | | | | | | |
| Clairol: #5 | | | | | | | | | −1:04 | −2:04 | +1:06 | +2:06 | Pig.:3 | File:051 |
| L'Oreal: M6 | | | | | | | | | −1:04 | −2:04 | +1:06 | +2:06 | Pig.:3 | File:051 |
| 24.E. MEDIUM BROWN (AUBURN TONES) - WARM | 22.00 | 27.00 | 3.50 | 6.00 | 4.25 | 10.00 | 4 | 5 | | | | | | |
| Clairol: #5 | | | | | | | | | −1:04 | −2:04 | +1:06 | +2:06 | Pig.:3 | File:054 |
| L'Oreal: M6 | | | | | | | | | −1:04 | −2:04 | +1:06 | +2:06 | Pig.:3 | File:054 |
| 25.F. DARKEST MEDIUM BLONDE - COOL | 27.00 | 28.00 | 1.80 | 6.00 | −5.00 | 6.00 | 1 | 6 | | | | | | |
| Clairol: #6 | | | | | | | | | −1:05 | −2:05 | +1:07 | +2:07 | Pig.:4 | File:061 |
| L'Oreal: M7 | | | | | | | | | −1:05 | −2:05 | +1:07 | +2:07 | Pig.:4 | File:061 |
| 26.F. DARKEST MEDIUM BLONDE - BORDER C/W - COOL | 27.00 | 28.00 | 1.80 | 5.00 | 6.00 | 6.50 | 2 | 6 | | | | | | |
| Clairol: #6 | | | | | | | | | −1:05 | −2:05 | +1:07 | +2:07 | Pig.:4 | File:061 |
| L'Oreal: M7 | | | | | | | | | −1:05 | −2:05 | +1:07 | +2:07 | Pig.:4 | File:061 |
| 27.F. DARKEST MEDIUM BLONDE - BORDER C/W - WARM | 27.00 | 28.00 | 5.00 | 6.00 | 6.00 | 6.50 | 3 | 6 | | | | | | |
| Clairol: #6 | | | | | | | | | −1:05 | −2:05 | +1:07 | +2:07 | Pig.:4 | File:064 |
| L'Oreal: M7 | | | | | | | | | −1:05 | −2:05 | +1:07 | +2:07 | Pig.:4 | File:064 |
| 28.F. DARKEST MEDIUM BLONDE - WARM | 27.00 | 28.00 | 1.80 | 6.00 | 6.50 | 15.00 | 4 | 6 | | | | | | |
| Clairol: #6 | | | | | | | | | −1:05 | −2:05 | +1:07 | +2:07 | Pig.:4 | File:064 |
| L'Oreal: M7 | | | | | | | | | −1:05 | −2:05 | +1:07 | +2:07 | Pig.:4 | File:064 |
| 29 G. MEDIUM BLONDE - COOL | 28.00 | 31.00 | 1.80 | 6.00 | −5.00 | 6.00 | 1 | 7 | | | | | | |
| Clairol: #6 | | | | | | | | | −1:06 | −2:06 | +1:08 | +2:08 | Pig.:4 | File:071 |
| L'Oreal: M8 | | | | | | | | | −1:06 | −2:06 | +1:08 | +2:08 | Pig.:5 | File:071 |
| 30 G. MEDIUM BLONDE - BORDER C/W - COOL | 28.00 | 31.00 | 1.80 | 5.00 | 6.00 | 6.50 | 2 | 7 | | | | | | |
| Clairol: #6 | | | | | | | | | −1:06 | −2:06 | +1:08 | +2:08 | Pig.:4 | File:071 |
| L'Oreal: M8 | | | | | | | | | −1:06 | −2:06 | +1:08 | +2:08 | Pig.:5 | File:071 |
| 31G. MEDIUM BLONDE - (G) BORDER C/W - WARM | 28.00 | 31.00 | 5.00 | 6.00 | 6.00 | 6.50 | 3 | 7 | | | | | | |
| Clairol: #6 | | | | | | | | | −1:06 | −2:06 | +1:08 | +2:08 | Pig.:4 | File:074 |
| L'Oreal: M8 | | | | | | | | | −1:06 | −2:06 | +1:08 | +2:08 | Pig.:5 | File:074 |
| 32G. MEDIUM BLONDE (G) - WARM | 28.00 | 31.00 | 1.80 | 6.00 | 6.50 | 15.00 | 4 | 7 | | | | | | |
| Clairol: #6 | | | | | | | | | −1:06 | −2:06 | +1:08 | +2:08 | Pig.:4 | File:074 |
| L'Oreal: M8 | | | | | | | | | −1:06 | −2:06 | +1:08 | +2:08 | Pig.:5 | File:074 |
| 33R. LIGHTEST MEDIUM BLONDE - COOL | 31.00 | 33.00 | 1.80 | 6.00 | −5.00 | 6.00 | 1 | 8 | | | | | | |
| Clairol: #7 | | | | | | | | | −1:07 | −2:07 | +1:09 | +2:09 | Pig.:5 | File:081 |
| L'Oreal: M8 | | | | | | | | | −1:07 | −2:07 | +1:09 | +2:09 | Pig.:5 | File:081 |
| 34H. LIGHTEST MEDIUM BLONDE - BORDER C/W - COOL | 31.00 | 33.00 | 1.80 | 5.00 | 6.00 | 6.50 | 2 | 8 | | | | | | |
| Clairol: #7 | | | | | | | | | −1:07 | −2:07 | +1:09 | +2:09 | Pig.:5 | File:081 |

TABLE VIII-continued

DATABASE

| Category Name | LMin | LMax | aMin | aMax | bMin | bMax | CW | Level | | | | | | |
|---|---|---|---|---|---|---|---|---|---|---|---|---|---|---|
| L'Oreal: M8 | | | | | | | | | −1:07 | −2:07 | +1:09 | +2:09 | Pig.:5 | File:081 |
| 35H. LIGHTEST MEDIUM BLONDE - BORDER C/W - WARM | 31.00 | 33.00 | 5.00 | 6.00 | 6.00 | 6.50 | 3 | 8 | | | | | | |
| Clairol: #7 | | | | | | | | | −1:07 | −2:07 | +1:09 | +2:09 | Pig.:5 | File:084 |
| L'Oreal: M8 | | | | | | | | | −1:07 | −2:07 | +1:09 | +2:09 | Pig.:5 | File:084 |
| 36H. LIGHTEST MEDIUM BLONDE - WARM | 31.00 | 33.00 | 1.80 | 6.00 | 6.50 | 15.00 | 4 | 8 | | | | | | |
| Clairol: #7 | | | | | | | | | −1:07 | −2:07 | +1:09 | +2:09 | Pig.:5 | File:084 |
| L'Oreal: M8 | | | | | | | | | −1:07 | −2:07 | +1:09 | +2:09 | Pig.:5 | File:084 |
| 37I. LIGHT BLONDE - COOL | 33.00 | 36.00 | 1.80 | 6.00 | −5.00 | 7.00 | 1 | 9 | | | | | | |
| Clairol: #7 | | | | | | | | | −1:08 | −2:08 | +1:10 | +2:10 | Pig.:5 | File:091 |
| L'Oreal: M9 | | | | | | | | | −1:08 | −2:08 | +1:10 | +2:10 | Pig.:6 | File:091 |
| 38I. LIGHT BLONDE - BORDER C/W - COOL | 33.00 | 36.00 | 1.80 | 5.00 | 7.00 | 7.50 | 2 | 9 | | | | | | |
| Clairol: #7 | | | | | | | | | −1:08 | −2:08 | +1:10 | +2:10 | Pig.:5 | File:091 |
| L'Oreal: M9 | | | | | | | | | −1:08 | −2:08 | +1:10 | +2:10 | Pig.:6 | File:091 |
| 39I. LIGHT BLONDE - BORDER C/W - WARM | 33.00 | 36.00 | 5.00 | 6.00 | 7.00 | 7.50 | 3 | 9 | | | | | | |
| Clairol: #7 | | | | | | | | | −1:08 | −2:08 | +1:10 | +2:10 | Pig.:5 | File:094 |
| L'Oreal: M9 | | | | | | | | | −1:08 | −2:08 | +1:10 | +2:10 | Pig.:6 | File:094 |
| 40I. LIGHT BLONDE - WARM | 33.00 | 36.00 | 1.80 | 6.00 | 7.50 | 20.00 | 4 | 9 | | | | | | |
| Clairol: #7 | | | | | | | | | −1:08 | −2:08 | +1:10 | +2:10 | Pig.:5 | File:094 |
| L'Oreal: M9 | | | | | | | | | −1:08 | −2:08 | +1:10 | +2:10 | Pig.:6 | File:094 |
| 41J. LIGHTER BLONDE - COOL | 36.00 | 40.00 | 1.80 | 6.00 | −5.00 | 8.00 | 1 | 10 | | | | | | |
| Clairol: #8 | | | | | | | | | −1:09 | −2:09 | +1:11 | +2:11 | Pig.:6 | File:101 |
| L'Oreal: M9 | | | | | | | | | −1:09 | −2:09 | +1:11 | +2:11 | Pig.:6 | File:101 |
| 42J. LIGHTER BLONDE - BORDER C/W - COOL | 36.00 | 40.00 | 1.80 | 5.00 | 8.00 | 8.50 | 2 | 10 | | | | | | |
| Clairol: #8 | | | | | | | | | −1:09 | −2:09 | +1:11 | +2:11 | Pig.:6 | File:101 |
| L'Oreal: M9 | | | | | | | | | −1:09 | −2:09 | +1:11 | +2:11 | Pig.:6 | File:101 |
| 43J. LIGHTER BLONDE - BORDER C/W - WARM | 36.00 | 40.00 | 5.00 | 6.00 | 8.00 | 8.50 | 3 | 10 | | | | | | |
| Clairol: #8 | | | | | | | | | −1:09 | −2:09 | +1:11 | +2:11 | Pig.:6 | File:104 |
| L'Oreal: M9 | | | | | | | | | −1:09 | −2:09 | +1:11 | +2:11 | Pig.:6 | File:104 |
| 44J. LIGHTER BLONDE - WARM | 36.00 | 40.00 | 1.80 | 6.00 | 8.50 | 20.00 | 4 | 10 | | | | | | |
| Clairol: #8 | | | | | | | | | −1:09 | −2:09 | +1:11 | +2:11 | Pig.:6 | File:104 |
| L'Oreal: M9 | | | | | | | | | −1:09 | −2:09 | +1:11 | +2:11 | Pig.:6 | File:104 |
| 45K. LIGHTEST BLONDE - COOL | 40.00 | 50.00 | 1.80 | 7.00 | −5.00 | 9.00 | 1 | 11 | | | | | | |
| Clairol: #9 | | | | | | | | | −1:10 | −2:10 | +1:11 | +2:11 | Pig.:8 | File:111 |
| L'Oreal: M10 | | | | | | | | | −1:10 | −2:10 | +1:11 | +2:11 | Pig.:6 | File:111 |
| 46K. LIGHTEST BLONDE - BORDER C/W COOL | 40.00 | 50.00 | 1.80 | 5.00 | 9.00 | 10.00 | 2 | 11 | | | | | | |
| Clairol: #9 | | | | | | | | | −1:10 | −2:10 | +1:11 | +2:11 | Pig.:8 | File:111 |
| L'Oreal: M10 | | | | | | | | | −1:10 | −2:10 | +1:11 | +2:11 | Pig.:6 | File:111 |
| 47K. LIGHTEST BLONDE - BORDER C/W WARM | 40.00 | 50.00 | 5.00 | 7.00 | 9.00 | 10.00 | 3 | 11 | | | | | | |
| Clairol: #9 | | | | | | | | | −1:10 | −2:10 | +1:11 | +2:11 | Pig.:8 | File:114 |
| L'Oreal: M10 | | | | | | | | | −1:10 | −2:10 | +1:11 | +2:11 | Pig.:6 | File:114 |
| 48K. LIGHTEST BLONDE - WARM | 40.00 | 50.00 | 1.80 | 7.00 | 10.00 | 30.00 | 4 | 11 | | | | | | |
| Clairol: #9 | | | | | | | | | −1:10 | −2:10 | +1:11 | +2:11 | Pig.:8 | File:114 |
| L'Oreal: M10 | | | | | | | | | −1:10 | −2:10 | +1:11 | +2:11 | Pig.:6 | File:114 |
| 49L. LIGHTEST BLONDE - COOL | 50.00 | 80.00 | 1.80 | 7.00 | −5.00 | 9.00 | 1 | 12 | | | | | | |
| Clairol: #10 | | | | | | | | | −1:10 | −2:10 | +1:12 | +2:12 | Pig.:8 | File:111 |
| L'Oreal: M10 | | | | | | | | | −1:10 | −2:10 | +1:12 | +2:12 | Pig.:6 | File:111 |
| 50L. LIGHTEST BLONDE - BORDER C/W COOL | 50.00 | 80.00 | 1.80 | 5.00 | 9.00 | 10.00 | 2 | 12 | | | | | | |
| Clairol: #10 | | | | | | | | | −1:10 | −2:10 | +1:12 | +2:12 | Pig.:8 | File:111 |
| L'Oreal: M10 | | | | | | | | | −1:10 | −2:10 | +1:12 | +2:12 | Pig.:6 | File:111 |
| 51L. LIGHTEST BLONDE - BORDER C/W WARM | 50.00 | 80.00 | 5.00 | 7.00 | 9.00 | 10.00 | 3 | 12 | | | | | | |
| Clairol: #10 | | | | | | | | | −1:10 | −2:10 | +1:12 | +2:12 | Pig.:8 | File:114 |
| L'Oreal: M10 | | | | | | | | | −1:10 | −2:10 | +1:12 | +2:12 | Pig.:6 | File:114 |
| 52L. LIGHTEST BLONDE - WARM | 50.00 | 80.00 | 1.80 | 7.00 | 10.00 | 30.00 | 4 | 12 | | | | | | |
| Clairol: #10 | | | | | | | | | −1:10 | −2:10 | +1:12 | +2:12 | Pig.:8 | File:114 |
| L'Oreal: M10 | | | | | | | | | −1:10 | −2:10 | +1:12 | +2:12 | Pig.:6 | File:114 |
| 53.M. LIGHT RED - COOL | 22.00 | 28.00 | 6.00 | 30.00 | −5.00 | 3.50 | 1 | 13 | | | | | | |
| Clairol: #5 (with Red Violet, Neutral or Blue Violet tones) | | | | | | | | | −1:14 | −2:14 | +1:07 | +2:07 | Pig.:3 | File:131 |

TABLE VIII-continued

DATABASE

| Category Name | LMin | LMax | aMin | aMax | bMin | bMax | CW | Level | | | | | | |
|---|---|---|---|---|---|---|---|---|---|---|---|---|---|---|
| L'Oreal: M6 (with Ash, Iridescent or Auburn tones) | | | | | | | | | −1:14 | −2:14 | +1:07 | +2:07 | Pig.:3 | File:131 |
| 54.M. LIGHT RED BORDER C/W - COOL | 22.00 | 28.00 | 6.00 | 30.00 | 3.50 | 3.75 | 2 | 13 | | | | | | |
| Clairol: #5 (with Red Violet, Neutral or Blue Violet tones) | | | | | | | | | −1:14 | −2:14 | +1:07 | +2:07 | Pig.:3 | File:131 |
| L'Oreal: M6 (with Ash, Iridescent or Auburn tones) | | | | | | | | | −1:14 | −2:14 | +1:07 | +2:07 | Pig.:3 | File:131 |
| 55.M. LIGHT RED BORDER C/W - WARM | 22.00 | 28.00 | 6.00 | 30.00 | 3.75 | 4.00 | 3 | 13 | | | | | | |
| Clairol: #5 (with Red Gold or Red Orange tones) | | | | | | | | | −1:14 | −2:14 | +1:07 | +2:07 | Pig.:3 | File:134 |
| L'Oreal: M6 (with Gold or Copper tones) | | | | | | | | | −1:14 | −2:14 | +1:07 | +2:07 | Pig.:3 | File:134 |
| 56. M. LIGHT RED-WARM | 22.00 | 28.00 | 6.00 | 30.00 | 4.00 | 30.00 | 4 | 13 | | | | | | |
| Clairol: #5 (with Red, Gold or Red Orange tones) | | | | | | | | | −1:14 | −2:14 | +1:07 | +2:07 | Pig.:3 | File:134 |
| L'Oreal: M6 (with Gold or Copper tones) | | | | | | | | | −1:14 | −2:14 | +1:07 | +2:07 | Pig.:3 | File:134 |
| 57.N. MEDIUM RED-COOL | 19.00 | 22.00 | 6.00 | 30.00 | −10.00 | 3.50* | 1 | 14 | | | | | | |
| Clairol: #4 (with Red Violet, Neutral or Blue Violet tones) | | | | | | | | | −1:15 | −2:15 | +1:13 | +2:13 | Pig.:2 | File:141 |
| L'Oreal: M5 (with Ash, Iridescent or Auburn tones) | | | | | | | | | −1:15 | −2:15 | +1:13 | +2:13 | Pig.:2 | File:141 |
| 58.N. MEDIUM RED BORDER C/W - COOL | 19.00 | 22.00 | 6.00 | 30.00 | 3.50 | 3.75 | 2 | 14 | | | | | | |
| Clairol: #4 (with Red Violet, Neutral or Blue Violet tones) | | | | | | | | | −1:15 | −2:15 | +1:13 | +2:13 | Pig.:2 | File:141 |
| L'Oreal: M5 (with Ash, Iridescent or Auburn tones) | | | | | | | | | −1:15 | −2:15 | +1:13 | +2:13 | Pig.:2 | File:141 |
| 59.N. MEDIUM RED (G) BORDER C/W WARM | 19.00 | 22.00 | 6.00 | 30.00 | 3.75 | 4.00 | 3 | 14 | | | | | | |
| Clairol: #4 (with Red, Gold or Red Orange tones) | | | | | | | | | −1:15 | −2:15 | +1:13 | +2:13 | Pig.:2 | File:144 |
| L'Oreal: M5 (with Gold or Copper tones) | | | | | | | | | −1:15 | −2:15 | +1:13 | +2:13 | Pig.:2 | File:144 |
| 60.N. MEDIUM RED (G) WARM | 19.00 | 22.00 | 6.00 | 30.00 | 4.00 | 30.00 | 4 | 14 | | | | | | |
| Clairol: #4 (with Red, Gold or Red Orange tones) | | | | | | | | | −1:15 | −2:15 | +1:13 | +2:13 | Pig.:2 | File:144 |
| L'Oreal: M5 (with Gold or Copper tones) | | | | | | | | | −1:15 | −2:15 | +1:13 | +2:13 | Pig.:2 | File:144 |
| 61.O. DARK RED COOL | 14.00 | 19.00 | 3.00 | 30.00 | −10.00 | 2.50 | 1 | 15 | | | | | | |
| Clairol: #2/#3 (with Red Violet or Blue Violet tones) | | | | | | | | | −1:03 | −2:03 | +1:14 | +2:14 | Pig.:2 | File:151 |
| L'Oreal: M4 (with Ash, Iridescent or Auburn tones) | | | | | | | | | −1:03 | −2:03 | +1:14 | +2:14 | Pig.:2 | File:151 |
| 62.O. DARK RED BORDER C/W- COOL | 14.00 | 19.00 | 3.00 | 30.00 | 2.50 | 2.75 | 2 | 15 | | | | | | |
| Clairol: #2/#3 (with Red Violet, Neutral or Blue Violet tones) | | | | | | | | | −1:03 | −2:03 | +1:14 | +2:14 | Pig.:2 | File:151 |
| L'Oreal: M4 (with Ash, Iridescent or Auburn tones) | | | | | | | | | −1:03 | −2:03 | +1:14 | +2:14 | Pig.:2 | File:151 |
| 63.0. DARK RED BORDER C/W - WARM | 14.00 | 19.00 | 3.00 | 30.00 | 2.75 | 3.00 | 3 | 15 | | | | | | |
| Clairol: #2/#3 (with Red, Gold or Red Orange tones) | | | | | | | | | −1:03 | −2:03 | +1:14 | +2:14 | Pig.:2 | File:000 |
| L'Oreal: M4 (with Gold or Copper tones) | | | | | | | | | −1:03 | −2:03 | +1:14 | +2:14 | Pig.:2 | File:151 |
| 64.O. DARK RED - WARM | 14.00 | 19.00 | 3.00 | 30.00 | 3.00 | 30.00 | 4 | 15 | | | | | | |
| Clairol: #2/#3 (with Red, Gold or Red Orange tones) | | | | | | | | | −1:03 | −2:03 | +1:14 | +2:14 | Pig.:2 | File:000 |
| L'Oreal: M4 (with Gold or Copper tones) | | | | | | | | | −1:03 | −2:03 | +1:14 | +2:14 | Pig.:2 | File:151 |
| 65.P. RED BLONDE | 27.00 | 40.00 | 6.00 | 30.00 | 6.00 | 30.00 | 4 | 16 | | | | | | |
| Clairol: #6/#7/#8 (with Red, Gold or Red Orange tones) | | | | | | | | | −1:13 | −2:13 | +1:18 | +2:18 | Pig.:7 | File:164 |
| L'Oreal: M7/M8 (with Gold or Copper tones) | | | | | | | | | −1:13 | −2:13 | +1:18 | +2:18 | Pig.:5 | File:164 |
| 66.Q. RED BLONDE | 40.00 | 50.00 | 7.00 | 30.00 | 6.00 | 30.00 | 4 | 17 | | | | | | |
| Clairol: #9/#10 (with Red, Gold or Red Orange tones) | | | | | | | | | −1:16 | −2:16 | +1:11 | +2:11 | Pig.:7 | File:164 |
| L'Oreal: M9 (with Gold or Copper tones) | | | | | | | | | −1:16 | −2:16 | +1:11 | +2:11 | Pig.:6 | File:164 |
| 67.R. RED BLONDE | 50.00 | 80.00 | 7.00 | 30.00 | 6.00 | 30.00 | 4 | 18 | | | | | | |

TABLE VIII-continued

DATABASE

| Category Name | LMin | LMax | aMin | aMax | bMin | bMax | CW | Level | | | | | |
|---|---|---|---|---|---|---|---|---|---|---|---|---|---|
| Clairol: #9/#10 (with Red, Gold or Red Orange tones) | | | | | | | | | −1:16 | −2:16 | +1:12 | +2:12 | Pig.:8 File:164 |
| L'Oreal: M9 (with Gold or Copper tones) | | | | | | | | | −1:16 | −2:16 | +1:12 | +2:12 | Pig.:6 File:164 |
| 68.S. BLACK/DARK BROWN/MEDIUM BROWN/BROWN WITH 7%–90% GREY HAIR - WARM | 27.00 | 50.00 | −10.00 | 1.80 | 4.25 | 10.00 | 4 | 19 | | | | | |
| Clairol: | | | | | | | | | −1:01 | −2:01 | +1:03 | +2:03 | Pig.:0 File:000 |
| L'Oreal: | | | | | | | | | −1:01 | −2:01 | +1:03 | +2:03 | Pig.:0 File:024 |
| 69.S. BLACK/DARK BROWN/MEDIUM BROWN/BROWN WITH 7%–90% GREY HAIR - BORDER C/W - WARM | 27.00 | 50.00 | −10.00 | 1.80 | 4.00 | 4.25 | 3 | 19 | | | | | |
| Clairol: | | | | | | | | | −1:01 | −2:01 | +1:03 | +2:03 | Pig.:0 File:000 |
| L'Oreal: | | | | | | | | | −1:01 | −2:01 | +1:03 | +2:03 | Pig.:0 File:024 |
| 70.S. BLACK/DARK BROWN/MEDIUM BROWN/BROWN WITH 7%–90% GREY HAIR - BORDER C/W - COOL | 27.00 | 50.00 | −10.00 | 1.80 | 3.75 | 4.00 | 2 | 19 | | | | | |
| Clairol: | | | | | | | | | −1:01 | −2:01 | +1:03 | +2:03 | Pig.:0 File:021 |
| L'Oreal: | | | | | | | | | −1:01 | −2:01 | +1:03 | +2:03 | Pig.:0 File:021 |
| 71.S. BLACK/DARK BROWN/MEDIUM BROWN/BROWN WITH 7%–90% GREY HAIR - COOL | 27.00 | 50.00 | −10.00 | 1.80 | −10.00 | 3.75 | 1 | 19 | | | | | |
| Clairol: | | | | | | | | | −1:01 | −2:01 | +1:03 | +2:03 | Pig.:0 File:021 |
| L'Oreal: | | | | | | | | | −1:01 | −2:01 | +1:03 | +2:03 | Pig.:0 File:021 |
| 72.T. BLACK/DARK BROWN/MEDIUM BROWN/BROWN WITH 40%–60% GREY HAIR - WARM | 23.00 | 27.00 | −10.00 | 1.00 | 4.25 | 10.00 | 4 | 20 | | | | | |
| Clairol: | | | | | | | | | −1:01 | −2:01 | +1:03 | +2:03 | Pig.:0 File:000 |
| L'Oreal: | | | | | | | | | −1:01 | −2:01 | +1:03 | +2:03 | Pig.:0 File:024 |
| 73.T. BLACK/DARK BROWN/MEDIUM BROWN/BROWN WITH 40%–60% GREY HAIR - BORDER C/W - WARM | 23.00 | 27.00 | −10.00 | 1.00 | 4.00 | 4.25 | 3 | 20 | | | | | |
| Clairol: | | | | | | | | | −1:01 | −2:01 | +1:03 | +2:03 | Pig.:0 File:000 |
| L'Oreal: | | | | | | | | | −1:01 | −2:01 | +1:03 | +2:03 | Pig.:0 File:024 |
| 74.T. BLACK/DARK BROWN/MEDIUM BROWN/BROWN WITH 40%–60% GREY HAIR - BORDER C/W - COOL | 23.00 | 27.00 | −10.00 | 1.00 | 3.75 | 4.25 | 2 | 20 | | | | | |
| Clairol: | | | | | | | | | −1:01 | −2:01 | +1:03 | +2:03 | Pig.:0 File:021 |
| L'Oreal: | | | | | | | | | −1:01 | −2:01 | +1:03 | +2:03 | Pig.:0 File:021 |
| 75.T. BLACK/DARK BROWN/MEDIUM BROWN/BROWN WITH 40%–60% GREY HAIR - COOL | 23.00 | 27.00 | −10.00 | 1.00 | −10.00 | 3.75 | 1 | 20 | | | | | |
| Clairol: | | | | | | | | | −1:01 | −2:01 | +1:03 | +2:03 | Pig.:0 File:021 |
| L'Oreal: | | | | | | | | | −1:01 | −2:01 | +1:03 | +2:03 | Pig.:0 File:021 |

TABLE IX

MANUFACTURERS PRODUCTS CLAIROL FILES

011:

| | |
|---|---|
| Logics Violet | -1V Black |
| Miss Clairol | -82N Dk. Neutral Brown |
| Miss Clairol | -52D Black Azure |
| Miss Clairol | -51D Black Velvet |

014:

| | |
|---|---|
| Logics Blue | -3B Medium Brown |
| Miss Clairol | -84N Lt. Neutral Brown |
| Logics Violet | -3V Medium Brown |
| Miss Clairol | -39G Sunset Brown |
| Miss Clairol | -95D-N Nightfall Brown |
| Miss Clairol | -46D Chestnut Brown |
| Loving Care | -80 Auburn |

TABLE IX-continued

MANUFACTURERS PRODUCTS CLAIROL FILES

| | |
|---|---|
| Miss Clairol | -56R Cinnamon |
| Miss Clairol | -37D Iced Brown |
| 021: | |
| | |
| Logics Violet | -2V Dark Brown |
| Logics Neutral | -2N Dark Brown |
| Logics Red Violet | -2RV Deep |
| Miss Clairol | -57D Coffee Brown |
| Miss Clairol | -48D Sable Brown |
| 031: | |
| | |
| Logics Blue | -3B Medium Brown |
| Logics Neutral | -3N Medium Brown |
| Logics Red Violet | -3RV Medium |
| Logics Violet | -3V Medium Brown |
| Loving Care | -79 Dark Brown |
| 034: | |
| | |
| Logics Gold | -3G Medium Brown |
| 044: | |
| | |
| Logics Blue | -4B Light Brown |
| Logics Violet | -4V Light Brown |
| Logics Red Violet | -4RV Light |
| Logics Neutral | -4N Light Brown |
| Miss Clairol | -84N Lt. Neutral Brown |
| Miss Clairol | -39G Sunset Brown |
| Miss Clairol | -95D-N Nightfall Brown |
| Miss Clairol | -46D Chestnut Brown |
| Loving Care | -80 Auburn |
| Miss Clairol | -56R Cinnamon |
| Miss Clairol | -37D Iced Brown |
| 044: | |
| | |
| Logics Gold | -4G Light Brown |
| Logics Red Orange | -4RO Deep Bright |
| Loving Care | -77 Medium Ash Brown |
| Miss Clairol | -75R Sunsparked Brown |
| Miss Clairol | -47R Red Ginger |
| Loving Care | -83 Natural Black |
| Miss Clairol | -46D Chestnut Brown |
| Loving Care | -80 Auburn |
| Miss Clairol | -56R Cinnamon |
| Loving Care | -82 Dark Warm Brown |
| Miss Clairol | -37 D Iced Brown |
| 051: | |
| | |
| Logics Neutral | -5N Lightest Brown |
| Logics Violet | -5V Lightest Brown |
| Miss Clairol | -94D-N Twilight Brown |
| Miss Clairol | -86N Dk. Neutral Brown |
| Born Blonde Toner | -360 Moonlight Mink |
| Miss Clairol | -36D Moonlit Brown |
| Beautiful Browns | -18D Darkest Brown |
| Beautiful Browns | -20D Black |
| Beautiful Browns | -15W Dark Warm Brown |
| Miss Clairol | -32D Moon Haze |
| 054: | |
| | |
| Beautiful Browns | -12D Medium Ash Brown |
| Loving Care | -76 Lt. Golden Brown |
| Creme Toner | -345D True Camel Beige |
| Creme Toner | -346D True Taupe Beige |
| Loving Care | -78 Med Golden Brown |
| Loving Care | -75 Light Ash Brown |
| Loving Care | -74 Reddish Blonde |
| Miss Clairol | -42D Moongold |
| Loving Care | -775 Smokey Ash Brown |
| Miss Clairol | -35G Sunlit Brown |
| Beautiful Browns | -20D Black |
| Beautiful Browns | -15W Dark Warm Brown |
| Miss Clairol | -32D Moon Haze |
| 061: | |
| | |
| Beautiful Browns | -11W Med Golden Brown |
| Jazzing | -78 Creme Soda |
| Born Blonde Toner | -354 Baby Blush |
| Creme Toner | -343D True Ash Blonde |
| Born Blonde Toner | -357 Beautitul Beige |
| Beautiful Browns | -131D Med Smokey Brown |
| Miss Clairol | -28D Autumn Mist |
| Miss Clairol | -25G Sunblonde Brown |
| Beautiful Browns | -13W Med Warm Brown |
| Miss Clairol | -74G Sunwashed Blonde |
| Beautiful Browns | -121W Med Honey Brown |
| 064: | |
| | |
| Beautiful Browns | -10W Bronzed Brown |
| Miss Clairol | -28D Autumn Mist |
| Miss Clairol | -25G Sunblonde Brown |
| Beautiful Browns | -13W Med Warm Brown |
| Miss Clairol | -74G Sunwashed Blonde |
| Beautiful Browns | -121W Med Honey Brown |
| Beautiful Browns | -131D Med Smokey Brown |
| 071: | |
| | |
| Born Blonde Toner | -356 Innocent Ivory |
| Logics Blue | -6V Dark Blonde |
| Born Blonde Toner | -358 Winsome Wheat |
| Beautiful Browns | -8D Light Ash Brown |
| Born Blonde Toner | -355 Blisstully Blonde |
| Jazzing | -76 Sandstorm |
| Born Blonde Toner | -359 Fair Fawn |
| Miss Clairol | -93D-N Dusk Blonde |
| Miss Clairol | -34D Hazy Mist |
| Miss Clairol | -88N Lt. Neutral Blnde |
| Miss Clairol | -34D Hazy Mist |
| Creme Toner | -342D True Brown Blonde |
| Creme Toner | -10B Sandy Blonde |
| Creme Toner | -341 True Tan Blonde |
| 074: | |
| | |
| Beautiful Blondes | -6D Blonde Brown |
| Miss Clairol | -41G Golden Apricot |
| Beautiful Reds | -9W Lt. Reddish Brown |
| Creme Toner | -344R True Tawny Beige |
| Loving Care | -73 Ash Blonde |
| Miss Clairol | -88N Lt. Neutral Blnde |
| Miss Clairol | -34D Hazy Mist |
| Creme Toner | -342 True Brown Blnd |
| Creme Toner | -10B Sandy Blonde |
| Creme Toner | -341D True Tan Blonde |
| 081: | |
| | |
| Born Blonde Toner | -352 precious Platnm |
| Born Blonde Toner | -353 Sweet Silver |
| Born Blonde Toner | -361 Happy Honey |
| Jazzing | -72 Icicle |
| Creme Toner | -311D 9A Towhead |
| Creme Toner | -309D Chapgn Parfait |
| Creme Toner | -331G Tan Pearl |
| Miss Clairol | -92D-N Daybreak Blonde |
| Logics Violet | -7V Medium Blonde |
| 084: | |
| | |
| Beautiful Blondes | -4W Med Golden Blonde |
| Creme Toner | -307D Champagne Ice |
| Logics Gold | -8G Light Blonde |
| Creme Toner | -303G Champgn Beige |
| Loving Care | -72 Golden Blonde |
| Beautiful Brights | -30W 14K Gold |
| Miss Clairol | -27G Spring Honey |
| Beautiful Blondes | -5D Light Ash Blonde |
| Creme Toner | -311D 9A Towhead |
| Creme Toner | -309D Champgn Parfait |
| Creme Toner | -331G Tan Pearl |
| Logics Violet | -7V Medium Blonde |
| Miss Clairol | -92DN Daybreak Blonde |
| Miss Clairol | -71R-G Sunrise Gold |

TABLE IX-continued

MANUFACTURERS PRODUCTS
CLAIROL FILES

091:

| | |
|---|---|
| Jazzing | -10 Clear Hairglosser |
| Logics Blue | -8B Light Blonde |
| Born Blonde Toner | -351 Silent Snow |
| Creme Toner | -310D Champgn Toast |

094:

| | |
|---|---|
| Beautiful Blondes | -2W Lt. Golden Blonde |

101:

| | |
|---|---|
| Logics Violet | -12V Ultra Lt. Blonde |
| Miss Clairol | -20D Arctic Blonde |
| Creme Toner | -302D Platinum Beige |
| Creme Toner | -319G Ivory Chiffon |
| Creme Toner | -315G X-Lite B |
| Logics Blue | -12B Ultra Lt. Blonde |
| Logics Violet | -8V Light Blonde |
| Miss Clairol | -91D-N Starlit Blonde |
| Creme Toner | -314G X-Lite A |
| Creme Toner | -332R Strawberry Blnde |
| Miss Clairol | -40D Topaz |
| Miss Clairol | -26D Winter Wheat |
| Logics Gold | -10G Lightest Blonde |

104:

| | |
|---|---|
| Creme Toner | -340G True Golden Blonde |
| Creme Toner | -332R Strawberry Blonde |
| Miss Clairol | -40D Topaz |
| Miss Clairol | -26D Winter Wheat |
| Logics Gold | -10G Lighest Blonde |

111:

| | |
|---|---|
| Creme Toner | -301D White Beige |
| Logics Blue | -10B Lighest Blonde |
| Creme Toner | -323D X-Lite Platinum |
| Miss Clairol | -30D Flaxen Blonde |
| Logics Violet | -10V Lightest Blonde |
| Logics Gold | -12G Ultra Lt. Blonde |

114:

| | |
|---|---|
| Miss Clairol | -12G Blondest Blonde |
| Jazzing | -20 Bold Gold |
| Logics Violet | -10V Lightest Blonde |
| Logics Gold | -12G Ultra Lt Blonde |

131:

| | |
|---|---|
| Beautiful Reds | -175W Wine Brown |
| Beautiful Brights | -17W Rosewood Brown |
| Beautiful Brights | -40W Amethyst |

134:

| | |
|---|---|
| Beautiful Reds | -14W Cedar Red Brown |
| Miss Clairol | -33F Flame |
| Miss Clairol | -45R Sparkling Sherry |
| Beautiful Brights | -38W Ruby |
| Logics Red Orange | -4RO Deep Bright |
| Miss Clairol | -44R Coppertone |
| Beautiful Reds | -17W Rosewood Brown |

141:

| | |
|---|---|
| Logics Red Violet | -3RV Medium |
| Logics Red Violet | -4RV Light |

144:

| | |
|---|---|
| Logics Red Violet | -4RV Light |
| Miss Clairol | -64R Red Oak |

151:

| | |
|---|---|
| Miss Clairol | -68R Berrywood |
| Miss Clairol | -70R Plum Brown |
| Logics Red Violet | -2RV Deep |

164:

| | |
|---|---|
| Logics Red Orange | -10RO Ltst Bright |
| Logics Red Orange | -8RO Light Bright |

TABLE IX-continued

MANUFACTURERS PRODUCTS
CLAIROL FILES

| | |
|---|---|
| Miss Clairol | -29R Honey Red |
| Miss Clairol | -43R Sun Bronze |
| Miss Clairol | -72R Sunberry |
| Beautiful Reds | -91W Copper Red |
| Jazzing | -40 Red Hot |
| Beautiful Brights | -34W Spiced Topaz |
| Beautiful Brights | -32W Amber |
| Jazzing | -30 Spiced Cognac |
| Logics Red Orange | -6RO Med Bright |
| Miss Clairol | -31R Sunny Auburn |
| Miss Clairol | -73R-G Apricot Glaze |

TABLE IX

L'OREAL FILES

011:

| | |
|---|---|
| Majirel | -M1 Black |
| Crescendo | -1 Black |
| Diacolor | -Darkest Brown |
| Diacolor | -Plum |

021:

| | |
|---|---|
| Crescendo | -3 Darkest Brown |
| Majirel | -M3 Darkest Brown |
| Majirel | -M5-12 Medium Ash Iridescent Brown |
| Majirel | -M4 Dark Brown |

024:

| | |
|---|---|
| Diacolor | -Dark Brown |
| Diacolor | -Medium Natural Ash Brown |

031:

| | |
|---|---|
| Crescendo | -4 Dark Brown |
| Crescendo | -5.1 Ash Brown |
| Crescendo | -5 Brown |
| Diacolor | -Medium Brown |
| Majirel | -M6.12 Light Ash Iridescent Brown |
| Majirel | -M6.1 Light Ash Brown |
| Majirel | -M5.1 Ash Brown |
| Majirel | -M5 Brown |

034:

| | |
|---|---|
| Diacolor | -Light Brown |
| Diacolor | -Light Natural Ash Blonde |
| Majirel | -M5 Brown |

041:

| | |
|---|---|
| Crescendo | -5 Brown |
| Majirel | -6.2 Light Iridescent Brown |
| Majirel | -M4.51 Ash Mahogany Brown |
| Crescendo | -6 Light Brown |
| Crescendo | -6.01 Light Natural Ash Brown |
| Crescendo | -6.12 Light Ash Iridescent Brown |
| Majirel | -M6.23 Light Iridescent Golden Brown |
| Majirel | -M5.15 Mahogany Ash Light Brown |
| Crescendo | -5.3 Golden Brown |

044:

| | |
|---|---|
| Diacolor | -Dark Blonde |
| Majirel | -M5.3 Golden Brown |
| Majirel | -M7.01 Dark Natural Ash Blonde |
| Crescendo | -6.52 Lt. Mahogany Irid Brown |
| Majirel | -M6 Light Brown |
| Majirel | -M7.1 Dark Ash Blonde |
| Majirel | -M6.01 Light Natural Amber Brown |
| Majirel | -M6.23 Light Iridescent Golden Brown |
| Majirel | -M5.15 Mahogany Ash Light Brown |
| Crescendo | -5.3 Golden Brown |

TABLE IX-continued

L'OREAL FILES

051:

| | |
|---|---|
| Majirel | -M7.23 Dark Iridescent Golden Blonde |
| Crescendo | -7.01 Dark Natural Ash Blonde |
| Crescendo | -7.1 Dark Ash Blonde |
| Diacolor | -Natural Ash |

054:

| | |
|---|---|
| Majirel | -Color Mixer Dark Ash |
| Crescendo | -8.31 Golden Ash Blonde |
| Crescendo | -7.31 Dk Golden Ash Blonde |
| Majirel | -M6.52 Light Mahogany Irid Brown |
| Majirel | -M7 Dark Blonde |
| Crescendo | -7 Dark Blonde |
| Crescendo | -8.52 Mahogany Irid Blonde |
| Crescendo | -8.42 Copper Irid Blonde |

061:

| | |
|---|---|
| Majirel | -Color Mixer Light Ash |
| Majirel | -M9.01 Natural Ash Blonde |
| Crescendo | -8.13 Ash Beige Blonde |
| Crescendo | -8.01 Natural Ash Blonde |
| Crescendo | -10.01 Very Light Ash Blonde |
| Crescendo | -10.01 Very Light Natural Blonde |
| Crescendo | -9.1 Light Ash Blonde |
| Diacolor | -Dark Natural Ash Blonde |
| Crescendo | -9.12 Light Ash Indescent Blonde |
| Crescendo | -9.13 Light Ash Beige Blonde |

064:

| | |
|---|---|
| Majirel | -M7.3 Dark Golden Blonde |
| Majirel | -M8.3 Golden Blonde |
| Majirel | -M8 Blonde |

071:

| | |
|---|---|
| Majirel | -M9.12 Light Ash Iridescent Blonde |
| Crescendo | -9.01 Lt Natural Ash Blonde |
| Majirel | -Color Mixer Light Ash |
| Majirel | -M8.1 Ash Blonde |
| Crescendo | -8 Blonde |

074:

| | |
|---|---|
| Crescendo | -9.04 Lt. Natural Copper Blonde |
| Crescendo | -8.3 Golden Blonde |
| Majirel | -M8.1 Ash Blonde |
| Crescendo | -8 Blonde |

081:

| | |
|---|---|
| Crescendo | -10.1 Very Light Ash Blonde |
| Crescendo | -10.01 Very Light Natural Blonde |
| Crescendo | -9.1 Light Ash Blonde |
| Crescendo | -9.12 Light Ash Iridescent Blonde |
| Crescendo | -9.13 Light Ash Beige Blonde |

084:

| | |
|---|---|
| Crescendo | -9.31 Lt Golden Ash Blonde |
| Crescendo | -9 Light Blonde |
| Crescendo | -9.12 Lt Ash Irid Blonde |
| Crescendo | -9.13 Lt Ash Beige Blonde |

091:

| | |
|---|---|
| Majirel | -M10.1 Very Lt Ash Blonde |
| Crescendo | -P10A Pearl Ash |
| Majirel | -M9.01 Lt. Natural Ash Blonde |
| Crescendo | -10.21 Very Light Iridescent Ash Blonde |
| Diacolor | -Light Beige |
| Majirel | -M0.01 Very Light Natural Ash Blonde |
| Crescendo | -P10A Shimmer Beige |
| Diacolor | -Light Ash Blonde |
| Crescendo | -10 Very Light Blonde |

094:

| | |
|---|---|
| Crescendo | -9.3 Light Golden Blonde |
| Majirel | -M9 Light Blonde |
| Majirel | -M9.3 Light Golden Blonde |
| Majiblond | -901X Extra Lt Ash Blonde |
| Diacolor | -Light Beige |
| Majirel | -M10.01 Very Light Natural Ash Blonde |
| Crescendo | -P10A Shimmer Beige |
| Diacolor | -Light Ash Blonde |
| Crescendo | -10 Very Light Blonde |

101:

| | |
|---|---|
| Majiblond | -901 Light Light Natural Ash Blonde |
| Majiblond | -Lightest Light Ash kid Blonde |

104:

| | |
|---|---|
| Majirel | -M10 Very Light Blonde |
| Majirel | -M9.13 Lt. Ash Beige Blonde |
| Majiblond | -900 Lt. Lt Natural Blonde |
| Majiblond | -911 Lightest Light Int Ash Blonde |

111:

| | |
|---|---|
| Crescendo | -P10E Iridescent Ivory |
| Diacolor | -Clear |

114:

| | |
|---|---|
| Majiblond | -913X Lightest Lt Natural Beige Blonde |
| Majiblond | 900X Extra Light Platinum Blonde |
| Diacolor | -Clear |

131:

| | |
|---|---|
| Majirel | -M6.6 Light Auburn Brown |

134:

| | |
|---|---|
| Majirel | -M6.64 Light Auburn Copper Brown |
| Diacolor | -Copper |
| Majirel | -M6.6 Light Auburn Brown |
| Crescendo | -7.43 Dk Copper Golden Blonde |
| Diacolor | -Golden Copper |
| Crescendo | -6.46 Light Copper Auburn Brown |

141:

| | |
|---|---|
| Diacolor | -Red Mahogany |
| Diacolor | -Dark Auburn |
| Majirel | -M7.62 Dark Auburn Iridescent Blonde |
| Diacolor | -Auburn |
| Diacolor | -Light Auburn |

144:

| | |
|---|---|
| Crescendo | -4.56 Dark Mahogany Auburn Brown |
| Majirel | -M7.62 Dark Auburn Irid Blonde |
| Diacolor | -Auburn |
| Diacolor | -Light Auburn |
| Crescendo | -4.45 Dark Copper Mahogany Brown |

151:

| | |
|---|---|
| Majirel | -M5.62 Auburn Iridescent Brown |
| Majirel | -M5.20 Int Iridescent Brown |

164:

| | |
|---|---|
| Majirel | -M8.34 Golden Copper Blonde |
| Majirel | -M9.04 Light Natural Copper Blonde |
| Majirel | -M7.4 Dark Copper Blonde |
| Majiblond | -903 Light Light Natural Golden Blonde |
| Majirel | -M7.40 Dark Int Copper Blonde |
| Diacolor | -Gold |
| Crescendo | -7.44 Dark Tp Copper Blonde |
| Crescendo | -8.34 Golden Copper Blonde |
| Crescendo | -4.56 Dark Mahogany Auburn Blonde |

TABLE X

LIST OF NATURAL HAIR COLOR OPTIONS
FOR GREY HAIR PROGRAM

1. If Grey is present in Black, Dark Brown, Medium Brown or Brown Hair, please press #1.
2. If Grey is present in Light Brown/Darkest Blonde Hair, please press #2.

TABLE X-continued

LIST OF NATURAL HAIR COLOR OPTIONS FOR GREY HAIR PROGRAM

3. If Grey is present in Dark Red, Medium Red, or Medium Light Red Hair, please press #3.
4. If Grey is present in Light Red or Red Blonde hair, please press #4.
5. If Grey is present in Medium to medium Dark Blonde Hair, please press #5.
6. If Grey is present in Light Blonde Hair, please press #6.

TABLE XI

CALCULATION OF PERCENTAGE OF GREY HAIR

For Color Categories in Table IX having grey (e.g. 61–68):
The "L" value of the natural hair (site #1) and the value of the "L" from another site. If the other site's "L" value is from 1 to 2 points higher than the "L" of the natural hair, the category is: 40% to 60% Grey Hair.
If the other site's "L" value is above 2 points higher than the "L" of the natural hair, the category is: 70% to 90% Grey Hair.
If the "L" value is under 1 point increase from the most natural site (Site #1), then the category is: Low percentage of Grey Hair.
For Color Categories containing grey, not listed in Table I:

LIGHT BROWN/DARKEST BLOND HAIR:

If "L" = +4 to + and     hair is 40%–60% Grey
"a" = 10.00 to −.80
If "L" = + 10 or higher and     hair is 70%–90% Grey
"a" = −10.00 to −.80

DARK RED MEDIUM RED OR MEDIUM LIGHT RED HAIR:

If "L" = +6 to +11 and     hair is 40%–60% Grey
"a" = −10.00 to −.80
If "L" = +11 or higher and     hair is 70%–90% Grey
"a" = −10.00 to −.80

LIGHT RED OR RED BLONDE HAIR:

If "L" = +5 to +7 and     hair is 40%–60% Grey
"a" = −10.00 to −.80
If "L" = +7 or higher and     hair is 70%–90% Grey
"a" = −10.00 to −.80

MEDIUM TO MEDIUM DARK BLONDE HAIR:

If "L" = +2 to +4     hair is 40%–60% Grey
If "L" = +4 or higher     hair is 70%–90% Grey

LIGHT BLONDE HAIR:

If "L" = −.25 or less and     hair is 40%–60% Grey
"a" is −1.5 to −2.00
If "L" = −.25 or less and     hair is 70%–90% Grey
"a" is −2.00 or higher

TABLE XII

CLAIROL PRODUCT RECOMMENDATIONS FOR COOL SKIN

BLACK
Miss Clairol     -82N Dk Neutral Brown
Miss Clairol     -52D Black Azure
Logics Violet     -1V Black
Miss Clairol     -51D Black Velvet
GRAY
Glorious Grays     -G07 Glorious Silver
Glorious Grays     -G05 Glorious Platinum
Glorious Grays     -G11 Glorious Smoke
Glorious Grays     -G09 Glorious Slate
DARKEST DARK BROWN
Miss Clairol     -57D Coffee Brown
Miss Clairol     -48D Sable Brown
Logics Violet     -2V Dark Brown
DARK BROWN
Logics Neutral     -3N Medium Brown
Loving Care     -79 Dark Brown

TABLE XII-continued

LIGHTEST DARK BROWN
Logics Blue     -3B Medium Brown
Miss Clairol     -84N Lt Neutrl Brown
Logics Violet     -3V Medium Brown
Miss Clairol     -39G Sunset Brown
Miss Clairol     -95D-N Nightfall Brown
LIGHTEST DARK BROWN COOL/WARM BORDERLINE SHADES
Miss Clairol     -46D Chestnut Brown
Loving Care     -80 Auburn
Miss Clairol     -56R Cinnamon
Miss Clairol     -37D Iced Brown
DARK MEDIUM BROWN
Miss Clairol     -94D-N Twilight Brown
Miss Clairol     -86N Dk Neutral Brown
Logics Neutral     -4N Light Brown
MEDIUM BROWN
Born Blonde Toner     -360 Moonlight Mink
Logics Blue     -4B Light Brown
Logics Neutral     -5N Lightest Brown
Miss Clairol     -36D Moonlit Brown
Beautiful Browns     -18D Darkest Brown
MEDIUM BROWN COOL/WARM BORDERLINE SHADES
Beautiful Browns     -20D Black
Beautiful Browns     -15 W Dark Warm Brown
Miss Clairol     -32D Moon Haze
DARK RED
Miss Clairol     -68R Berrywood
Miss Clairol     -70R Plum Brown
Logics Red Violet     -2RV Deep
MEDIUM RED
Logics Red Violet     -3RV Medium
MEDIUM RED COOL/WARM BORDERLINE SHADE
Logics Red Violet     -4RV Light
LIGHT RED/LIGHT AUBURN
Beautitul Reds     -175W Wine Brown
LIGHT RED/LIGHT AUBURN COOL/WARM BORDERLINE SHADE
Beautiful Brights     -17W Rosewood Brown
DARK AUBURN COOL/WARM BORDERLINE SHADES
Beautiful Brights     -40W Amethyst
Miss Clairol     -64R Red Oak
LIGHTEST LIGHT BLONDE
Creme Toner     -301D White Beige
Logics Blue     -10B Lightest Blonde
Creme Toner     -323D X-Lite Platinum
Miss Clairol     -30D Flaxen Blonde
LIGHTEST LIGHT BLONDE COOL/WARM BORDERLINE SHADES
Logics Violet     -10V Lightest Blonde
Logics Gold     -12G Ultra Lt. Blonde
LIGHT BLONDE
Logics Violet     -12V Ultra Lt Blonde
Miss Clairol     -20D Arctic Blonde
Creme Toner     -302 D Platinum Beige
Creme Toner     -319D Ivory Chiffon
Creme Toner     -315G X-Lite B
Logics Blue     -12B Ultra Lt Blonde
Logics Violet     -8V Light Blonde
Miss Clairol     -91D-N Starlit Blonde
Creme Toner     -314G X-Lite A
LIGHT BLONDE COOL/WARM BORDERLINE SHADE
Creme Toner     -332R Strawberry Blnde
Miss Clairol     -40D Topaz
Miss Clairol     -26D Winter Wheat
Logics Gold     -10G Lightest Blonde
DARKEST LIGHT BLONDE
Jazzing     -10 Clear Hairglosser
Logics Blue     -8B Light Blonde
Born Blonde Toner     -351 Silent Snow
Creme Toner     -310D Champgn Toast
LIGHTEST MEDIUM BLONDE
Born Blonde Toner     -352 Precious Platnm
Born Blonde Toner     -353 Sweet Silver
Born Blonde Toner     -361 Happy Honey
Jazzing     -72 Icicle
LIGHTEST MEDIUM BLONDE COOL/WARM BORDERLINE SHADES
Creme Toner     -311D 9A Towhead
Creme Toner     -309D Champgn Parfait
Creme Toner     -331G Tan Pearl
Miss Clairol     -92D-N Daybreak Blonde TABLE XII-continued

| | |
|---|---|
| Logics Violet | -7V Medium Blonde |
| MEDIUM BLONDE | |
| Born Blonde Toner | -356 Innocent Ivory |
| Logics Blue | -6V Dark Blonde |
| Born Blonde Toner | 358 Winsome Wheat |
| Beautitul Browns | -8D Light Ash Brown |
| Born Blonde Toner | -355 Blissfully Blonde |
| Jazzing | -76 Sandstorm |
| Born Blonde Toner | -359 Fair Fawn |
| Miss Clairol | -93D-N Dusk Blonde |
| Miss Clairol | -34D Hazy Mist |
| MEDIUM BLONDE COOL/WARM BORDERLINE SHADES | |
| Miss Clairol | -89N Lt Neutral Blonde |
| Miss Clairol | -34D Hazy Mist |
| Creme Toner | -342D True Brown Blnde |
| Creme Toner | -10B Sandy Blonde |
| Crerne Toner | -341D True Tan Blonde |
| DARKEST MEDIUM BLONDE & LIGHTEST BROWN | |
| Beautiful Browns | -11W Med Golden Brown |
| Jazzing | -78 Creme Soda |
| Born Blonde Toner | -354 Baby Blush |
| Creme Toner | -343D True Ash Blonde |
| Born Blonde Toner | -357 Beautiful Beige |
| Beautiful Browns | -131D Med Smokey Brown |
| DARKEST MEDIUM BLONDE & LIGHTEST BROWN COOL/WARM BORDERLINE SHADES | |
| Miss Clairol | -28D Autumn Mist |
| Miss Clairol | -25G Sunblonde Brown |
| Beautiful Browns | -13W Med Warm Brown |
| Miss Clairol | -74G Sunwashed Blonde |
| Beautiful Browns | -121W Med Honey Brown |
| BLACK | |
| Majirel | -M1 Black |
| Crescendo | -1 Black |
| Diacolor | -Plum |
| BLACK BORDERLINE SHADE | |
| Diacolor | -Darkest Brown |
| DARKEST DARK BROWN | |
| Crescendo | -3 Darkest Brown |
| Majirel | -M3 Darkest Brown |
| Majirel | -M5.12 Medium Ash Iridescent Brown |
| Majirel | -M4 Dark Brown |
| MEDIUM DARK BROWN | |
| Crescendo | -4 Dark Brown |
| Crescendo | -5.1 Ash Brown |
| Crescendo | -5 Brown |
| Diacolor | -Medium Brown |
| Majirel | -M6.12 Light Ash Iridescent Brown |
| Majirel | -M6.1 Light Ash Brown |
| Majirel | -M5.1 Ash Brown |
| MEDIUM DARK BROWN COOL/WARM BORDERLINE SHADE | |
| Majirel | -M5 Brown |
| LIGHTEST DARK BROWN | |
| Crescendo | -5 Brown |
| Majirel | -6.2 Light Iridescent Brown |
| Majirel | -M4.51 Ash Mahogany Brown |
| Crescendo | -6 Light Brown |
| Crescendo | -6.01 Light Natural Ash Brown |
| Crescendo | -6.12 Light Ash Iridescent Brown |
| LIGHTEST DARK BROWN COOL/WARM BORDERLINE SHADE | |
| Majirel | -M6.23 Light Iridescent Golden Brown |
| Majirel | -M5.15 Mahogany Ash Light Brown |
| Crescendo | -5.3 Golden Brown |
| MEDIUM BROWN | |
| Majirel | -M7.23 Dark Iridescent Golden Blonde |
| Crescendo | -7.01 Dark Natural Ash Blonde |
| Crescendo | -7.1 Dark Ash Blonde |
| Diacolor | -Natural Ash |
| DARK RED | |
| Majirel | -M.562 Auburn Iridescent Brown |
| Majirel | -M5.20 Int Iridescent Brown |
| MEDIUM RED | |
| Diacolor | -Red Mahogany |
| Diacolor | -Dark Auburn |
| MEDIUM RED COOL/WARM BORDERLINE SHADE | |
| Majirel | -M7.62 Dark Auburn Iridescent Blonde |
| Diacolor | -Auburn |
| Diacolor | -Light Auburn |
| LIGHT RED COOL/WARM BORDERLINE SHADE | |

TABLE XII-continued

| | |
|---|---|
| Majirel | -M6.6 Light Auburn Brown |
| LIGHTEST LIGHT BLONDE | |
| Crescendo | -P10E Iridescent Ivory |
| LIGHTEST LIGHT BLONDE COOL/WARM BORDERLINE SHADE | |
| Diacolor | -Clear |
| MEDIUM LIGHT BLONDE | |
| Majiblond | -901 Light Light Natural Ash Blonde |
| Majiblond | -Lightest Light Ash Irid Blonde |
| DARKEST LIGHT BLONDE | |
| Majirel | -M10.1 Very Lt Ash Blonde |
| Crescendo | -P10A Pearl Ash |
| Majirel | -M9.01 Lt Natural Ash Blonde |
| Crescendo | -10.21 Very Light Iridescent Ash Blonde |
| DARKEST LIGHT BLONDE COOL/WARM BORDERLINE SHADE | |
| Diacolor | -Light Beige |
| Majirel | -M10.01 Very Light Natural Ash Blonde |
| Crescendo | -P10A Shimmer Beige |
| Diacolor | -Light Ash Blonde |
| Crescendo | -10 Very Light Blonde |
| LIGHTEST MEDIUM BLONDE | |
| Crescendo | -10.1 Very Light Ash Blonde |
| Crescendo | -10.01 Very Light Natural Blonde |
| Crescendo | -9.1 Light Ash Blonde |
| LIGHTEST MEDIUM BLONDE COOL/WARM BORDERLINE SHADE | |
| Crescendo | -9.12 Light Ash Iridescent Blonde |
| Crescendo | -9.13 Light Ash Beige Blonde |
| MEDIUM BLONDE | |
| Majirel | -M9.12 Light Ash Iridescent Blonde |
| Crescendo | -9.01 Lt Natural Ash Blonde |
| Majirel | -Color Mixer Light Ash |
| MEDIUM BLONDE COOL/WARM BORDERLINE SHADE | |
| Majirel | -M8.1 Ash Blonde |
| Crescendo | -8 Blonde |
| DARKEST MEDIUM BLONDE | |
| Majirel | -Color Mixer Light Ash |
| Majirel | -M9.01 Natural Ash Blonde |
| Crescendo | -8.13 Ash Beige Blonde |
| Crescendo | -8.01 Natural Ash Blonde |
| Diacolor | -Dark Natural Ash Blonde |
| REDDISH BLONDE | |
| Crescendo | -4.56 Dark Mahogany Auburn Blonde |

| CLAIROL PRODUCT RECOMMENDATIONS FOR WARM SKIN | |
|---|---|
| DARK BROWN | |
| Logics Gold | -3G Medium Brown |
| BROWN WITH AUBURN TONES | |
| Miss Clairol | -75R Sunsparked Brown |
| Miss Clairol | -47R Red Ginger |
| LIGHTEST DARK BROWN | |
| Logics Gold | -4G Light Brown |
| LIGHTEST DARK BROWN WARM/COOL BORDERLINE SHADES | |
| Loving Care | -83 Natural Black |
| Miss Clairol | -46D Chestnut Brown |
| Loving Care | -80 Auburn |
| Miss Clairol | -56R Cinnamon |
| Loving Care | -82 Dark Warm Brown |
| Miss Clairol | -37D Iced Brown |
| DARK MEDIUM BROWN | |
| Loving Care | -77 Medium Ash Brown |
| MEDIUM BROWN | |
| Loving Care | -76 Lt Golden Brown |
| Loving Care | -78 Med Golden Brown |
| Creme Toner | -346D True Taupe Beige |
| Logics Gold | -6G Dark Blonde |
| Loving Care | -75 Light Ash Brown |
| Logics Violet | -6V Dark Blonde |
| Logics Violet | -4V Light Brown |
| Loving Care | -74 Reddish Blonde |
| Miss Clairol | -42D Moongold |
| Miss Clairol | -35G Sunlit Brown |
| Beautiful Browns | -12D Medium Ash Brown |
| Creme Toner | -345D True Camel Beige |
| Logics Violet | -5V Lightest Brown |
| Loving Care | -775 Smokey Ash Brown |
| MEDIUM BROWN WARM/COOL BORDERLINE SHADES | |
| Beautiful Browns | -20D Black |
| Beautiful Browns | -15W Dark Warm Brown |
| Miss Clairol | -32D Moon Haze |

TABLE XII-continued

| | |
|---|---|
| MEDIUM RED WARM/COOL BORDERLINE SHADE | |
| Logics Red Violet | -4RV Light |
| LIGHT RED/LIGHT AUBURN | |
| Miss Clairol | -33R Flame |
| Miss Clairol | -45R Sparkling Sherry |
| Beautiful Brights | -38W Ruby |
| Logics Red Orange | -4R0 Deep Bright |
| Miss Clairol | -44R Coppertone |
| Beautiful Reds | -14W Cedar Red Brown |
| LIGHT RED/LIGHT AUBURN WARM/COOL BORDERLINE SHADE | |
| Beautiful Reds | -17W Rosewood Brown |
| DARK AUBURN WARM/COOL BORDERLINE SHADE | |
| Beautiful Brights | -40W Amethyst |
| Miss Clairol | -64R Red Oak |
| LIGHTEST LIGHT BLONDE | |
| Miss Clairol | -12G Blondest Blonde |
| Jazzing | -20 Bold Gold |
| LIGHTEST LIGHT BLONDE WARM/COOL BORDERLINE SHADES | |
| Logics Violet | -10V Lightest Blonde |
| Logics Gold | -12G Ultra Lt Blonde |
| LIGHT BLONDE | |
| Creme Toner | -340G True Golden Blonde |
| LIGHT BLONDE WARM/COOL BORDERLINE SHADES | |
| Creme Toner | -432R Strawberry Blnde |
| Miss Clairol | -40D Topaz |
| Miss Clairol | -26D Winter Wheat |
| Logics Gold | -10G Lightest Blonde |
| DARKEST LIGHT BLONDE | |
| Beautiful Blondes | -2W Lt Golden Blonde |
| LIGHTEST MEDIUM BLONDE | |
| Beautiful Blondes | -4W Med Golden Blonde |
| Creme Toner | -307D Champagne Ice |
| Logics Gold | -8G Light Blonde |
| Loving Care | -72 Golden Blonde |
| Beautiful Brights | -30W 14K Gold |
| Miss Clairol | -27G Spring Honey |
| Beautiful Blondes | -5D Light Ash Blonde |
| Creme Toner | -303G Champgn Beige |
| LIGHTEST MEDIUM BLONDE WARM/COOL BORDERLINE SHADES | |
| Creme Toner | -311D 9A Towhead |
| Creme Toner | -309D Champgn Parfait |
| Creme Toner | -331G Tan Pearl |
| Logics Violet | -7V Medium Blonde |
| Miss Clairol | -92DN Daybreak Blonde |
| LIGHTEST MEDIUM BLONDE W/REDDISH TONES | |
| Miss Clairol | -71R-G Sunrise Gold |
| MEDIUM BLONDE | |
| Beautiful Blondes | -6D Blonde Brown |
| Miss Clairol | -41G Golden Apricot |
| Beautiful Reds | -9W Lt Reddish Brown |
| Loving Care | -73 Ash Bionde |
| Creme Toner | -344R True Tawny Beige |
| MEDIUM BLONDE WARM/COOL BORDERLINE SHADES | |
| Miss Clairol | -88N Lt Neutral Blnde |
| Miss Clairol | -34D Hazy Mist |
| Creme Toner | -342D True Brown Blnd |
| Creme Toner | -10B Sandy Blonde |
| Creme Toner | -341D True Tan Blonde |
| DARKEST MEDIUM BLONDE & LIGHTEST BROWN | |
| Beautiful Browns | - 10W Bronzed Brown |
| DARKEST MEDIUM BLONDE & LIGHTEST BROWN WARM/COOL BORDERLINE SHADES | |
| Miss Clairol | -28D Autumn Mist |
| Miss Clairol | -25G Sunblonde Brown |
| Beautiful Browns | -13W Med Warm Brown |
| Miss Clairol | -74G Sunwashed Blonde |
| Beautiful Browns | -121W Med Honey Brown |
| Beautiful Browns | -131D Med Smokey Brown |
| REDDISH BLONDE | |
| Logics Red Orange | -10RO Ltst Bright |
| Logics Red Orange | -8R0 Light Bright |
| Miss Clairol | -29R Honey Red |
| Miss Clairol | -43R Sun Bronze |
| Miss Clairol | -72R Sunberry |
| Beautiful Reds | -91W Copper Red |
| Jazzing | -40 Red Hot |
| Beautiful Brights | -34W Spiced Topaz |
| Beautiful Brights | -32W Amber |
| Jazzing | -30 Spiced Cognac |
| Logies Red Orange | -6R0 Med Bright |
| Miss Clairol | -31R Sunny Auburn |
| Miss Clairol | -73R-G Apricot Glaze |
| BLACK WARM/COOL BORDERLINE SHADE | |
| Diacolor | -Darkest Brown |
| DARKEST DARK BROWN | |
| Diacolor | -Dark Brown |
| Diacolor | -Medium Natural Ash Brown |
| MEDIUM DARK BROWN | |
| Diacolor | -Light Brown |
| Diacolor | -Light Natural Ash Blonde |
| MEDIUM DARK BROWN WARM/COOL BORDERLINE SHADE | |
| Majirel | -M5 Brown |
| LIGHTEST DARK BROWN | |
| Diacolor | -Dark Blonde |
| Majirel | -M7.01 Dark Natural Ash Blonde |
| Crescendo | -6.52 Light Mahogany Irid Brown |
| Majirel | -M6 Light Brown |
| Majirel | -M5.3 Golden Brown |
| Majirel | -M7.1 Dark Ash Blonde |
| Majirel | -M6.01 Light Natural Amber Brown |
| LIGHTEST DARK BROWN WARM/COOL BORDERLINE SHADE | |
| Majirel | -M6.23 Light Iridescent Golden Brown |
| Majirel | -M5.15 Mahogany Ash Light Brown |
| Crescendo | -5.3 Golden Brown |
| MEDIUM BROWN | |
| Crescendo | -8.31 Golden Ash Blonde |
| Crescendo | -7.31 Dk Golden Ash Blonde |
| Majirel | -M6.52 Light Mahogany Irid Brown |
| Majirel | -M7 Dark Blonde |
| Crescendo | -7 Dark Blonde |
| Crescendo | -8.52 Mahogany Irid Blonde |
| Crescendo | -8.42 Copper kid Blonde |
| Majirel | -Color Mixer Dark Ash |
| MEDIUM RED | |
| Crescendo | -4.56 Dark Mahogany Auburn Brown |
| MEDIUM RED WARM/COOL BORDERLINE SHADE | |
| Majirel | -M7.62 Dark Auburn Irid Blonde |
| Diacolor | -Auburn |
| Diacolor | -Light Auburn |
| LIGHT RED | |
| Majirel | -M6.64 Light Auburn Copper Brown |
| Diacolor | -Copper |
| LIGHT RED WARM/COOL BORDERLINE SRADE | |
| Majirel | -M6.6 Light Auburn Brown |
| DARK AUBURN | |
| Crescendo | -4.45 Dark Copper Mahogany Brown |
| LIGHT AUBURN | |
| Crescendo | -7.43 Dk Copper Golden Blonde |
| Diacolor | -Golden Copper |
| Crescendo | -6.46 Light Copper Auburn Brown |
| LIGHTEST LIGHT BLONDE | |
| Majiblond | -913X Lightest Lt Natural Beige Blonde |
| Majiblond | -900X Extra Light Platinum Blonde |
| LIGHTEST LIGHT BLONDE WARM/COOL BORDERLINE SHADE | |
| Diacolor | -Clear |
| MEDIUM LIGHT BLONDE | |
| Majirel | -M10 Very Light Blonde |
| Majirel | -M9.13 Lt Ash Beige Blonde |
| Majiblond | -900 Lt Lt Natural Blonde |
| Majiblond | -911 Lightest Light Int Ash Blonde |
| DARKEST LIGHT BLONDE | |
| Crescendo | -9.3 Light Golden Blonde |
| Majirel | -M9 Light Blonde |
| Majirel | -M9.3 Light Golden Blonde |
| Majiblond | -901X Extra Lt Ash Blonde |
| DARKEST LIGHT BLONDE WARM/COOL BORDERLINE SHADE | |
| Diacolor | -Light Beige |
| Majirel | -M10.01 Very Light Natural Ash Blonde |
| Crescendo | -P10A Shimmer Beige |
| Diacolor | -Light Ash Blonde |
| Crescendo | -10 Very Light Blonde |
| LIGHTEST MEDIUM BLONDE | |
| Crescendo | -9.31 Lt Golden Ash Blonde |
| Crescendo | -9 Light Blonde |
| LIGHTEST MEDIUM BLONDE WARM/COOL BORDERLINE SHADE | |
| Crescendo | -9.12 Lt Ash Irid Blonde |
| Crescendo | -9.13 Lt Ash Beige Blonde |

TABLE XII-continued

MEDIUM BLONDE
Crescendo         -9.04 Lt Natural Copper Blonde
Crescendo         -8.3 Golden Blonde
MEDIUM BLONDE WARM/COOL BORDERLINE SHADE
Majirel           -M8.1 Ash Blonde
Crescendo         -8 Blonde
DARKEST MEDIUM BLONDE
Majirel           -M7.3 Dark Golden Blonde
Majirel           -M8.3 Golden Blonde
Majirel           -M8.18 Ash Beige Blonde
Majirel           -M8 Blonde
REDDISH BLONDE
Majirel           -M8.34 Golden Copper Blonde
Majirel           -M9.04 Light Natural Copper Blonde
Majirel           -M7.4 Dark Copper Blonde
Majiblond         -9.03 Light Light Natural Golden Blonde
Majirel           -M7.40 Dark Int Copper Blonde
Diacolor          -Gold
Crescendo         -7.44 Dark Tp Copper Blonde

What is claimed is:

1. A calibration standard for calibrating a skin color measuring instrument to allow measurements of skin coloration varying over a range of coloration, said calibration standard being made of non-skin material and being characterized by CIE (1931), standard illuminant C, color coordinates Y, x and y, wherein the value of said coordinates are Y=31.5–35, x=approximately 0.37–0.38 and y=approximately 0.34–0.35.

2. The calibration standard of claim 1, wherein the coordinates are approximately Y=34.66, x=0.3703 and y=0.3456.

3. The calibration standard of claim 1, wherein the coordinates are approximately Y=34.89, x=0.3702 and y=0.3464.

4. The calibration standard of claim 1, wherein said calibration standard is substantially free of metamerism.

* * * * *